(12) United States Patent
Arai et al.

(10) Patent No.: US 9,075,304 B2
(45) Date of Patent: *Jul. 7, 2015

(54) METHOD OF PRODUCING AMMONIUM SALT COMPOUND, METHOD OF PRODUCING COMPOUND, AND COMPOUND, POLYMERIC COMPOUND, ACID GENERATOR, RESIST COMPOSITION AND METHOD OF FORMING RESIST PATTERN

(71) Applicant: Tokyo Ohka Kogyo Co., Ltd., Kawasaki-shi (JP)

(72) Inventors: Masatoshi Arai, Kawasaki (JP); Yoshiyuki Utsumi, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 47 days.

This patent is subject to a terminal disclaimer.

(21) Appl. No.: 13/936,895

(22) Filed: Jul. 8, 2013

(65) Prior Publication Data

US 2014/0017617 A1 Jan. 16, 2014

(30) Foreign Application Priority Data

Jul. 10, 2012 (JP) ................................. 2012-155039

(51) Int. Cl.
| | |
|---|---|
| G03F 7/004 | (2006.01) |
| C08F 220/24 | (2006.01) |
| G03F 7/039 | (2006.01) |
| C07C 209/68 | (2006.01) |
| C07C 381/12 | (2006.01) |
| C08F 220/22 | (2006.01) |

(52) U.S. Cl.
CPC ............ *G03F 7/0045* (2013.01); *C08F 220/24* (2013.01); *G03F 7/0046* (2013.01); *G03F 7/0397* (2013.01); *C07C 209/68* (2013.01); *C07C 381/12* (2013.01); *C08F 220/22* (2013.01)

(58) Field of Classification Search
CPC ....... G03F 7/004; C08F 220/24; C08F 220/34
USPC ....................... 430/270.1; 526/243
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,949,325 B2 | 9/2005 | Li et al. | |
| 8,048,610 B2 * | 11/2011 | Ohsawa et al. | 430/270.1 |
| 2001/0049073 A1 | 12/2001 | Hada et al. | |
| 2004/0110085 A1 | 6/2004 | Iwai et al. | |
| 2009/0069521 A1 | 3/2009 | Nagai et al. | |
| 2009/0069595 A1 * | 3/2009 | Komata et al. | 562/512 |
| 2009/0162788 A1 | 6/2009 | Hada et al. | |
| 2009/0197204 A1 | 8/2009 | Shiono et al. | |
| 2009/0317743 A1 | 12/2009 | Shiono et al. | |
| 2010/0075256 A1 | 3/2010 | Joo et al. | |
| 2010/0310985 A1 | 12/2010 | Mori et al. | |
| 2011/0117499 A1 | 5/2011 | Matsumiya et al. | |
| 2011/0177453 A1 | 7/2011 | Masubuchi et al. | |
| 2012/0100487 A1 * | 4/2012 | Hirano et al. | 430/325 |
| 2012/0172555 A1 * | 7/2012 | Coley et al. | 526/243 |
| 2012/0282551 A1 | 11/2012 | Matsuzawa et al. | |
| 2012/0288128 A1 * | 11/2012 | Jost et al. | 381/315 |
| 2012/0328993 A1 * | 12/2012 | Utsumi et al. | 430/325 |
| 2013/0089819 A1 * | 4/2013 | Kawaue et al. | 430/285.1 |
| 2013/0224659 A1 * | 8/2013 | Ohashi et al. | 430/285.1 |
| 2013/0224660 A1 * | 8/2013 | Ohashi et al. | 430/285.1 |
| 2013/0260319 A1 * | 10/2013 | Arai et al. | 430/325 |
| 2013/0337387 A1 | 12/2013 | Yahagi et al. | |
| 2014/0162189 A1 * | 6/2014 | Ohashi et al. | 430/270.1 |
| 2014/0272707 A1 * | 9/2014 | Fukushima et al. | 430/270.1 |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2005-336452 | 12/2005 |
| JP | A-2006-259582 | 9/2006 |
| JP | A-2006-317803 | 11/2006 |
| JP | A-2009-025707 | 2/2009 |
| JP | A-2009-025723 | 2/2009 |
| JP | A-2009-149588 | 7/2009 |
| JP | A-2010-002870 | 1/2010 |
| JP | A-2010-032994 | 2/2010 |
| JP | A-2010-277043 | 12/2010 |
| JP | A-2011-013569 | 1/2011 |
| JP | A-2011-128226 | 6/2011 |
| WO | WO 2004/074242 A2 | 9/2004 |
| WO | WO 2006/121096 A1 | 11/2006 |
| WO | WO 2010/044372 | 4/2010 |

OTHER PUBLICATIONS

Office Action in U.S. Appl. No. 13/851,880, mailed Nov. 17, 2014.

* cited by examiner

*Primary Examiner* — Amanda C Walke
(74) *Attorney, Agent, or Firm* — Knobbe Martens Olson & Bear LLP

(57) ABSTRACT

A method of producing an ammonium salt compound, including reacting a first ammonium salt compound containing a first ammonium cation which is a primary, secondary or tertiary ammonium cation with a nitrogen-containing compound having a lone pair to obtain a second ammonium salt compound which contains a conjugated acid of the nitrogen-containing compound, the conjugated acid of the nitrogen-containing compound having a larger pKa than the pKa of the first ammonium cation; and a method of producing a compound, including a step of salt exchange between the ammonium salt compound obtained by the aforementioned production method and a sulfonium cation or iodonium cation which has a higher hydrophobicity than the hydrophobicity of the conjugated acid of the nitrogen-containing compound.

19 Claims, No Drawings

METHOD OF PRODUCING AMMONIUM SALT COMPOUND, METHOD OF PRODUCING COMPOUND, AND COMPOUND, POLYMERIC COMPOUND, ACID GENERATOR, RESIST COMPOSITION AND METHOD OF FORMING RESIST PATTERN

TECHNICAL FIELD

The present invention relates to a compound useful as an acid generator for a resist composition, a method of producing the compound, a method of producing an ammonium salt compound as a raw material for the compound, an acid generator including the compound, a resist composition including the acid generator, and a method of forming a resist pattern using the resist composition.

Priority is claimed on Japanese Patent Application No. 2012-155039, filed on Jul. 10, 2012, the content of which is incorporated herein by reference.

BACKGROUND ART

In lithography techniques, for example, a resist film composed of a resist material is formed on a substrate, and the resist film is subjected to selective exposure, followed by development, thereby forming a resist pattern having a predetermined shape on the resist film. A resist material in which the exposed portions of the resist film become soluble in a developing solution is called a positive-type, and a resist material in which the exposed portions of the resist film become insoluble in a developing solution is called a negative-type.

In recent years, in the production of semiconductor elements and liquid crystal display elements, advances in lithography techniques have lead to rapid progress in the field of pattern miniaturization. Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production of the semiconductor elements. Furthermore, research is also being conducted into lithography techniques that use an exposure light source having a wavelength shorter (energy higher) than these excimer lasers, such as electron beam (EB), extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator component is typically used.

If the resist film formed using the resist composition is selectively exposed during formation of a resist pattern, then within the exposed portions, acid is generated from the acid generator component, and the action of this acid causes an increase in the polarity of the base resin, making the exposed portions soluble in the alkali developing solution. Thus, by conducting alkali developing, the unexposed portions remain to form a positive resist pattern.

On the other hand, in the case where such a chemically amplified resist composition is applied to a solvent developing process using a developing solution containing an organic solvent (organic developing solution), the porarity of the base resin at exposed portions is increased, whereas the solubility at exposed portions in an organic developing solution is relatively decreased. As a result, the unexposed portions of the resist film are dissolved and removed by the organic developing solution, and a negative resist pattern in which the exposed portions are remaining is formed. Such a solvent developing process for forming a negative-tone resist composition is sometimes referred to as "negative-tone developing process" (for example, see Patent Document 1).

In general, the base resin for a chemically amplified resist composition contains a plurality of structural units for improving lithography properties and the like. For example, in the case of a resin composition which exhibits increased solubility in an alkali developing solution by the action of acid, a structural unit containing an acid decomposable group which is decomposed by the action of acid generated from an acid generator component or the like and exhibits increased polarity. Further, a structural unit containing a lactone-containing cyclic group or a structural unit containing a polar group such as a hydroxy group is used (for example, see Patent Document 2).

On the other hand, as acid generators usable in a chemically amplified resist composition, various types have been proposed including, for example, onium salt acid generators; oxime sulfonate acid generators; diazomethane acid generators; nitrobenzylsulfonate acid generators; iminosulfonate acid generators; and disulfone acid generators.

In recently, as the miniaturization of patterns proceeds, a compound useful as an acid generator for a resist composition is demanded.

Patent Document 3 discloses an invention related to an ammonium salt compound or a method of producing the same, which has an anion moiety having a high polarity and a sterically bulky structure and which is useful as an intermediate used in the synthesis of an acid generator for a resist composition. The ammonium salt compound is produced by reacting a halide, a nitrogen-containing compound (amine or ammonium salt) and either an alkali metal or ammonium salt.

Further, as an acid generator for a resist composition, a resin having an acid generator group which is decomposed upon exposure and then generates acid can be used. For example, as a base resin, a resin obtained by copolymerizing a monomer having an acid generator group which generates acid upon exposure and a monomer having an acid decomposable group which is decomposed by the action of acid and then exhibits increased polarity is used.

Such a resin composition has both the function as an acid generator and the function as a base component, and hence, can compose a chemically amplified resist composition by itself.

Patent Document 4 discloses a polymerizable fluorine-containing sulfonate as a monomer having an acid generator group, which is produced by esterification between a specific carboxylic acid derivative and 1,1-difluoro-2-hydroxy-ethanesulfonate, and discloses a method of producing the polymerizable fluorine-containing sulfonate.

DOCUMENTS OF RELATED ART

Patent Document

[Patent Document 1] Japanese Unexamined Patent Application, First Publication No. 2009-025723
[Patent Document 2] Japanese Unexamined Patent Application, First Publication No. 2003-241385
[Patent Document 3] Japanese Unexamined Patent Application, First Publication No. 2009-149588
[Patent Document 4] WO2010/044372

SUMMARY OF THE INVENTION

As further progress is made in lithography techniques and the application field for lithography techniques expands, further improvement in various lithography properties is demanded in the formation of a resist pattern.

To meet this requirement, in the production of the acid generator for the resist compositions, in addition to high yield, to reduce impurities is important. By virtue of reducing impurities, lithography properties are improved in the formation of a resist pattern. However, the methods disclosed in Patent Documents 3 and 4, further improvement in yield and reduction of impurities are required.

The present invention takes the above circumstances into consideration, with an object of providing a method of producing an acid generator, which can provide an acid generator having hardly any impurities with a high yield.

A first aspect of the present invention for solving the aforementioned problems is a method of producing an ammonium salt compound, including reacting a first ammonium salt compound containing a first ammonium cation which is a primary, secondary or tertiary ammonium cation with a nitrogen-containing compound having a lone pair to obtain a second ammonium salt compound which contains a conjugated acid of the nitrogen-containing compound, the conjugated acid of the nitrogen-containing compound having a larger pKa than the pKa of the first ammonium cation.

A second aspect of the present invention is a method of producing a compound, including: a step of reacting a first ammonium salt compound containing a first ammonium cation which is a primary, secondary or tertiary ammonium cation with a nitrogen-containing compound having a lone pair to obtain a second ammonium salt compound which contains a conjugated acid of the nitrogen-containing compound, the conjugated acid of the nitrogen-containing compound having a larger pKa than the pKa of the first ammonium cation; and a step of conducting salt exchange between the second ammonium salt compound and a sulfonium cation or iodonium cation which has a higher hydrophobicity than the hydrophobicity of the conjugated acid of the nitrogen-containing compound.

A third aspect of the present invention is a compound produced by the method of producing a compound according to the second aspect.

A fourth aspect of the present invention is a polymeric compound having a structural unit derived from a compound of the third aspect of the present invention, which has a polymerizable group.

A fifth aspect of the present invention is an acid generator including a compound of the third aspect of the present invention.

A sixth aspect of the present invention is a resist composition including a polymeric compound of the fourth aspect of the present invention or an acid generator of the fifth aspect of the present invention.

A seventh aspect of the present invention is a method of forming a resist pattern, including forming a resist film on a substrate using a resist composition according to the sixth aspect, subjecting the resist film to exposure, and subjecting the resist film to developing to form a resist pattern.

According to the present invention, there is provided a method of producing an acid generator which can provide an acid generator having hardly any impurities with a high yield.

According to the present invention, there are provided a compound useful as an acid generator for a resist composition, a method of producing the compound, a method of producing an ammonium salt compound as a raw material for the compound, an acid generator including the compound, a resist composition including the acid generator, and a method of forming a resist pattern using the resist composition.

MODE FOR CARRYING OUT THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atom(s).

The term "structural unit" refers to a monomer unit that contributes to the formation of a polymeric compound (resin, polymer, and copolymer).

The expression "may have a substituent" means that a case where a hydrogen atom (—H) is substituted with a monovalent group, or a case where a methylene (—CH$_2$—) group is substituted with a divalent group.

The term "exposure" is used as a general concept that includes irradiation with any form of radiation.

An "organic group" refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid (CH$_2$=CH—COOH) has been substituted with an organic group.

The acrylate ester may have the hydrogen atom bonded to the carbon atom on the α-position substituted with a substituent. The substituent (e) that substitutes the hydrogen atom bonded to the carbon atom on the α-position is an atom other than hydrogen or a group, and examples thereof include an alkyl group of 1 to 5 carbon atoms and a halogenated alkyl group of 1 to 5 carbon atoms. Further, an acrylate ester having the hydrogen atom bonded to the carbon atom on the α-position substituted with a substituent ($R^{\alpha 0}$) which has been substituted with a substituent containing an ester bond (e.g., an itaconic acid diester), or an acrylic acid having the hydrogen atom bonded to the carbon atom on the α-position substituted with a substituent ($R^{\alpha 0}$) which has been substituted with a hydroxyalkylgroup or a group in which the hydroxy group within a hydroxyalkyl group has been modified (e.g., α-hydroxyalkyl acrylate) can be mentioned as an acrylate ester having the hydrogen atom bonded to the carbon atom on the α-position substituted with a substituent. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from acrylamide" refers to a structural unit that is formed by the cleavage of the ethylenic double bond of acrylamide.

The acrylamide may have the hydrogen atom bonded to the carbon atom on the α-position substituted with a substituent, and may have either or both terminal hydrogen atoms on the amino group of acrylamide substituted with a substituent. A carbon atom on the α-position of an acrylamide refers to the carbon atom bonded to the carbonyl group, unless specified otherwise.

As the substituent which substitutes the hydrogen atom on the α-position of acrylamide, the same substituents as those described above for the substituent ($R^{\alpha 0}$) on the α-position of the aforementioned α-substituted acrylate ester can be mentioned.

A "structural unit derived from hydroxystyrene or a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and which may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and which may have the hydrogen atom on the α-position substituted with a substituent; and benzoic acid which has a substituent other than a hydroxy group or a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

The term "styrene" includes styrene itself and compounds in which the hydrogen atom at the α-position of styrene has been substituted with another substituent such as an alkyl group or a halogenated alkyl group.

A "structural unit derived from styrene or a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

《Production Method of Ammonium Salt Compound》

The method of producing an ammonium salt compound of the first aspect of the present invention is a method of producing an ammonium salt compound, including reacting a first ammonium salt compound with a nitrogen-containing compound having a lone pair to obtain a second ammonium salt compound. The first ammonium salt compound contains a first ammonium cation which is a primary, secondary or tertiary ammonium cation.

In the case where a first ammonium salt compound reacts with a nitrogen-containing compound, when the nitrogen atom within the nitrogen-containing compound has a lone pair, the nitrogen-containing compound accepts a proton ($H^+$) from the first ammonium salt compound, thereby producing a conjugated acid (i.e., second ammonium cation). That is, the nitrogen-containing compound acts as a proton acceptor, and the first ammonium salt compound acts as a proton donor. The cation moiety of the first ammonium salt compound is replaced by the conjugated acid (i.e., second ammonium cation), thereby producing a second ammonium salt compound.

The second ammonium salt compound produced by the production method is useful as an intermediate used in the synthesis of an acid generator for a resist composition.

In the production method of the present invention, taking into consideration the pKa value of the cation moiety of the second ammonium salt compound to be obtained, the nitrogen-containing compound and the first ammonium salt compound are selected and used in combination.

(Nitrogen-Containing Compound)

The nitrogen-containing compound used in the reaction with the first ammonium salt compound has a lone pair, and a conjugated acid thereof has a larger pKa value than that of the first ammonium cation of the first ammonium salt compound.

As a result, the first ammonium cation as a cation moiety of the first ammonium salt compound can be easily replaced by the conjugated acid (i.e., second ammonium cation).

In the present invention, "pKa" refers to an acid dissociation constant which is generally used as a parameter which shows the acid strength of an objective substance. The pKa value of the cation (e.g., ammonium cation, conjugated acid of a nitrogen-containing compound) can be determined by a conventional method. Alternatively, the pKa value can be estimated by calculation using a conventional software such as "ACD/Labs" (trade name; manufactured by Advanced Chemistry Development, Inc.).

For example, it is preferable that the pKa value of the conjugated acid of the nitrogen-containing compound (i.e., second ammonium cation) is relatively 2 or more larger than the pKa value of the first ammonium cation, and it is more preferable that the pKa value of the conjugated acid of the nitrogen-containing compound is relatively 3 or more larger than the pKa value of the first ammonium cation. Here, the pKa value is calculated by simulation using the aforementioned software such as ACD/Labs, Software V11.02.

When the pKa value of the conjugated acid of the nitrogen-containing compound is relatively 2 or more larger than the pKa value of the first ammonium cation, the reaction between the nitrogen-containing compound and first ammonium salt compound satisfactorily proceeds. On the other hand, the upper limit of difference in pKa value between a conjugated acid of a nitrogen-containing compound and a first ammonium cation is not particularly limited, and taking into consideration selectivity of preferable materials, the difference is preferably 10 or less.

With respect to the nitrogen-containing compound, it is preferable that a pKa value of the conjugated acid thereof is no less than 6 and the upper limit of the pKa value is no more than 20. pKa is preferably 7 to 18, more preferably 7 to 15, and particularly preferably 8 to 14.

When the pKa value is at least as large as the lower limit of the above-mentioned range, the reaction between the nitrogen-containing compound and first ammonium salt compound satisfactorily proceeds. On the other hand, when the pKa value is no more than the upper limit of the above-mentioned range, the stability of the first ammonium salt compound, and the stability of production process of the ammonium salt compound are improved.

Further, it is preferable that the hydrophobicity of the conjugated acid of the nitrogen-containing compound is lower than that of the first ammonium cation moiety. As a result, the cation moiety of the second ammonium salt compound can be easily replaced by another cation moiety.

In the present invention, the "hydrophobicity of cation moiety" can be compared based on each retention time in the case where two or more target cation moieties are analyzed under the same condition by using High-performance liquid chromatography (HPLC) method (e.g., reversed-phase high-performance liquid chromatography) to determine the retention time of each cation moiety. In the present invention, with respect to the measurement results of HPLC method, a cation moiety having a relatively short retention time refers "cation having a low hydrophobicity (cation having a high hydrophilicity)", and a cation moiety having a relatively long retention time refers "cation having a high hydrophobicity (cation having a low hydrophilicity)".

The apparatus and condition for HPLC method is not particularly limited, as long as they are generally used in the analysis of a compound and can analyze the target cation moieties. More specifically, the retention time can be measured under the following conditions.

Eluent (developing solvent): acetonitrile/buffer solution (Volume ratio: 50/50)

Buffer solution: trifluoroacetic acid aqueous solution of 0.1% by weight

Apparatus: Dionex U3000 (manufactured by Dionex Corporation)

Column: Speriorex ODS (manufactured by Shiseido Co., Ltd.); Length of the column: 25 cm Detector: Corona CAD (manufactured by ESA Biosciences, Inc.)

Flow rate: 1 mL/min

Column temperature: 30° C.

Sample concentration: acetonitrile solution having a solid content of 0.1% by weight Injection volume: 2 µL Here, the sample concentration is a solid content of a compound in which an anion moiety is Br⁻ and a cation moiety has a various objective structure.

It is preferable that the retention time of the conjugated acid of the nitrogen-containing compound (i.e., second ammonium cation) is 1 to 3.5 minutes, and more preferably 1.5 to 3 minutes, and still more preferably 1.5 to 2.5 minutes, wherein the retention time is measured under the specific condition in accordance with the aforementioned HPLC method.

When the retention time is at least as large as the lower limit of the above-mentioned range, the solubility of the second ammonium cation in an organic solvent is improved. On the other hand, when the retention time is no more than the upper limit of the above-mentioned range, the cation moiety of the second ammonium salt compound can be easily replaced by another cation moiety (e.g., a sulfonium cation or an iodonium cation).

When the second ammonium salt compound is subjected to salt exchange with a sulfonium cation or an iodonium cation, it is preferable that the retention time of the conjugated acid of the nitrogen-containing compound is relatively at least 0.2 minutes shorter than that of a sulfonium cation or an iodonium cation, and at least 0.3 minutes shorter is more preferable (i.e., it is preferable that the retention time of the conjugated acid of the nitrogen-containing compound is relatively at least 0.2 minutes faster than that of a sulfonium cation or an iodonium cation and at least 0.3 minutes faster is more preferable).

When the retention time of the conjugated acid of the nitrogen-containing compound is relatively at least 0.2 minutes shorter than that of a sulfonium cation or an iodonium cation, the cation moiety of the second ammonium salt compound can be easily replaced by a sulfonium cation or an iodonium cation.

Examples of such a nitrogen-containing compound include an amine represented by general formula (ca2-1) shown below, a cyclic amine (cyclic amidine, cyclic tert-alkylamine) and the like.

[Chemical Formula 1]

(ca2-1)

In the formula, $R^1$, $R^2$ and $R^3$ each independently represents a hydrogen atom, an alkyl group or 1 to 15 carbon atoms which may have a substituent, an aralkyl group which may have a substituent or a nitrogen-containing heterocyclic group which may have a substituent.

In the formula (cat-1), as the alkyl group for $R^1$, $R^2$ and $R^3$, a linear, branched or cyclic alkyl group can be mentioned, and preferably a linear or branched alkyl group. The alkyl group for $R^1$, $R^2$ and $R^3$ has 1 to 15 carbon atoms, preferably 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group. Among these, an ethyl group or an isopropyl group is more preferable.

The aralkyl group for $R^1$, $R^2$ and $R^3$ is preferably a benzyl group or a naphthylmethyl group.

The nitrogen-containing heterocyclic group for $R^1$, $R^2$ and $R^3$ may be aromatic or aliphatic. The nitrogen-containing heterocyclic group is preferably 4 to 7-membered ring, more preferably 4 to 6-membered ring and specific examples thereof include a pyridine ring group or a triazine ring group.

Examples of the substituent which $R'$, $R^2$ and $R^3$ may have include an alkyl group, an alkoxy group, a hydroxy group, an oxo group (=O), an amino group and the like. The alkyl group and the alkoxy group as a substituent preferably have 1 to 5 carbon atoms.

Specific examples of the amines represented by general formula (ca2-1) are shown below.

[Chemical Formula 2]

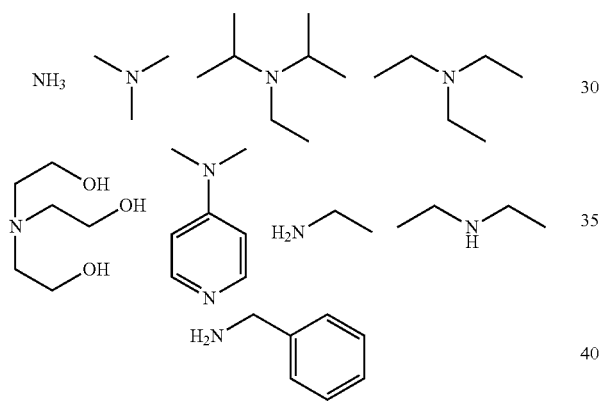

Specific examples of the cyclic amines (e.g., cyclic amidines, cyclic tert-alkylamines) are shown below.

[Chemical Formula 3]

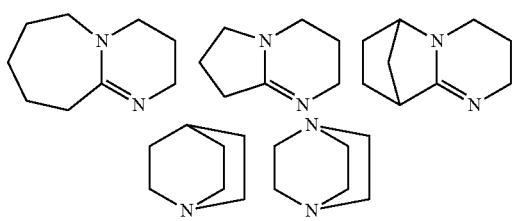

Here, the aforementioned cyclic amines may have a substituent as follows.

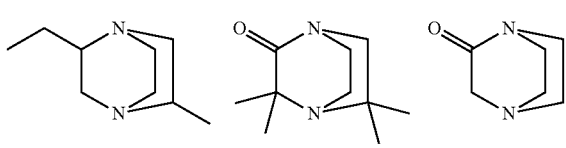

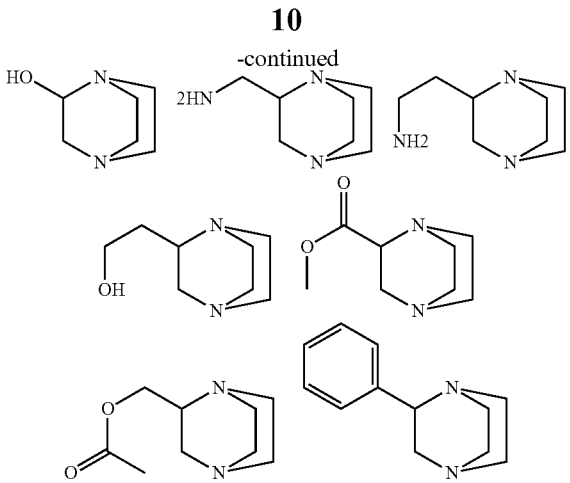

Further, the each conjugated acid of the specific examples of nitrogen-containing compounds, the retention time and pKa value of the conjugated acid are shown below.

Here, the retention time shown together with the chemical structure is a value measured under the specific condition in accordance with the aforementioned HPLC method. Further, the pKa value is a simulation result calculated using ACD/Labs, Software V11.02 (product name, Advanced Chemistry Development Inc.).

It is presumed that the retention time of a conjugated acid of an amine which is not shown below is within the range from 1 to 3 minutes or less (or 3.5 minutes or less), because of its high hydrophilicity. The pKa value of the conjugated acid of the amine is 7.5 or more, since each amine is strong base. For example, the pKa value of a conjugated acid of triethanolamine is 7.7.

[Chemical Formula 4]

| Conjugated acid | | | |
|---|---|---|---|
| Retention time (minute) | 2.2 | 2.2 | 2.2 |
| pKa | 10.62 | 10.98 | 9.52 |

(First Ammonium Salt Compound)

The first ammonium salt compound contains a first ammonium cation which is a primary, secondary or tertiary ammonium cation.

Cation Moiety of First Ammonium Salt Compound

The pKa value of the first ammonium cation is smaller than that of the conjugated acid of the aforementioned nitrogen-containing compound.

For example, it is preferable that the pKa value of the first ammonium cation is less than 8, and more preferably greater than 0 and 7.5 or less, and still more preferably 1 to 7. Here, the pKa value is calculated by simulation using the aforementioned software such as ACD/Labs, Software V11.02.

When the pKa value is less than 8, the reaction with the nitrogen-containing compound easily proceeds. On the other hand, the pKa value is greater than 0, the stability of the first ammonium salt compound is improved.

Further, it is preferable that the hydrophobicity of the first ammonium cation is higher than that of a cation moiety of a compound (P) described later.

With respect to the first ammonium cation, the retention time (which is measured under the specific condition in accordance with the aforementioned HPLC method) may be taken into consideration only in the case where the first ammonium salt compound is synthesized via a precursor (i.e., precursor of the first ammonium salt compound; compound (P) described later).

It is preferable that the retention time of the first ammonium cation is longer than that of the cation moiety (e.g., alkali metal cation) of the precursor (i.e., compound (P)). Specifically, it is preferable that the retention time of the first ammonium salt cation is 3 minutes or more, and more preferably 3.3 minutes or more. The upper limit is not particularly limited, and may be 30 minutes, and preferably 20 minutes or less.

When the retention time of the first ammonium cation is at least as large as the lower limit of the above-mentioned range, salt exchange reaction between the precursor (i.e., compound (P)) and first ammonium cation can reliably proceeds. When the cation moiety of the compound (P) is removed by washing treatment, the yield loss of the salt (objective compound) composed of the first ammonium cation and the anion moiety of the compound (P) can be improved. Longer retention time is more preferable.

Further, with respect to the difference in retention time between the first ammonium cation and the cation moiety (e.g., alkali metal cation) of the precursor thereof (compound (P)), it is preferable that the retention time of the first ammonium cation is 0.5 minute or more longer than that of the cation of the precursor thereof (compound (P)), and it is more preferable that the retention time of the first ammonium cation is 1 minute or more longer than that of the cation of the precursor thereof (compound (P)).

It is preferable that the first ammonium cation has a pKa value smaller than that of a conjugated acid of the nitrogen-containing compound, and has an electron-withdrawing group in order to facilitate the reaction with nitrogen-containing compound. Specific examples of preferable first ammonium cations are shown below.

[Chemical Formula 5]

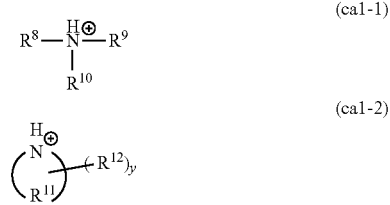

In the formulae, $R^8$ to $R^{10}$ each independently represents a hydrogen atom, an alkyl group of 1 to 15 carbon atoms which may have a substituent, a fluorinated alkyl group which may have a substituent or an aryl group which may have a substituent, and at least one of $R^8$ to $R^{10}$ represents a fluorinated alkyl group or an aryl group; $R^{11}$ represents a group which forms an aromatic ring with the nitrogen atom bonded to the $R^{11}$ group; $R^{12}$ represents an alkyl group of 1 to 15 carbon atoms or a halogen atom; and y represents an integer of 0 to 5.

In the formula (ca1-1), as the alkyl group for $R^8$ to $R^{10}$, a linear, branched or cyclic alkyl group can be mentioned, and a linear or branched alkyl group is preferable, and a linear alkyl group is more preferable. The alkyl group for $R^8$ to $R^{10}$ has 1 to 15 carbon atoms.

In the case where a first ammonium salt compound is synthesized via a compound (P) as a precursor, the larger the number of carbon atoms of an alkyl group is, the higher hydrophobicity. From industrial viewpoint, the alkyl group preferably has 1 to 5 carbon atoms, and preferable examples include a methyl group, an ethyl group, a propyl group, an isopropyl group, an n-butyl group, an isobutyl group, a tert-butyl group, a pentyl group, an isopentyl group and a neopentyl group. When two of $R^8$ to $R^{10}$ represent alkyl groups, these groups may be mutually bonded to form a ring.

Furthermore, as the alkyl group of this fluorinated alkyl group for $R^8$ to $R^{10}$, the same groups as those described above can be mentioned, and the fluorination ratio of the fluorinated alkyl group is preferably 50% or more, and more preferably 75% or more.

The aryl group for $R^8$ to $R^{10}$ is preferably a phenyl group or a naphthyl group.

When at least one of $R^8$ to $R^{10}$ represents a fluorinated alkyl group or an aryl group, the compound tends to exhibit weak basicity, and therefore, the reaction for producing a second ammonium salt compound (i.e., reaction between a nitrogen-containing compound and a first ammonium salt compound) easily proceeds.

Further, in the case where a first ammonium salt compound is synthesized via a compound (P) as a precursor, it is preferable that at least $R^8$ to $R^{10}$ is an aryl group, such that the hydrophobicity of the compound can be improved, that is, the retention time becomes long, and therefore, salt exchange between the cation moiety of a precursor (compound (P)) and a first ammonium cation satisfactorily proceeds.

When only $R^{10}$ among $R^8$ to $R^{10}$ is a fluorinated alkyl group or an aryl group, the remaining $R^8$ and $R^9$ are preferably a hydrogen atom or an alkyl group, and a hydrogen atom or an n-butyl group is more preferable. Further, $R^8$ and $R^9$ are still more preferably the same groups.

In the formula (ca1-2), $R^{11}$ is a group which forms an aromatic ring with the nitrogen atom having the $R^{11}$ group bonded thereto. The aromatic ring is preferably 4 to 7-membered ring, more preferably 4 to 6-membered ring and still more preferably 6-membered ring.

$R^{12}$ represents an alkyl group of 1 to 15 carbon atoms, and the same groups as those described above can be mentioned. In the case where a first ammonium salt compound is synthesized via a compound (P) as a precursor, the larger the number of carbon atoms of an alkyl group for $R^{12}$ is, the higher hydrophobicity. From industrial viewpoint, a tert-butyl group is preferable.

The halogen atom for $R^{12}$ is preferably a fluorine atom.

y represents an integer of 0 to 5, and preferably an integer of 0 to 2 and particularly preferably 2.

Specific examples of the first ammonium cation represented by the general formula (ca1-1) or (ca1-2) are shown below.

Here, the retention time shown together with the chemical structure is a value measured under the specific condition in accordance with the aforementioned HPLC method. The retention time may be taken into consideration only in the case where the first ammonium salt compound is synthesized via the precursor (compound (P)). In order to adjust the retention time at least 3 minutes or more, it is preferable that at least one of $R^8$ to $R^{10}$ in the formula (ca1-1) is an aryl group and the remaining groups are alkyl groups, or it is preferable that $R^{12}$ in the formula (ca1-2) is an alkyl group and y is 1 or more.

The pKa value is a simulation result calculated using ACD/Labs, Software V11.02 (product name, Advanced Chemistry Development Inc.).

[Chemical Formula 6]

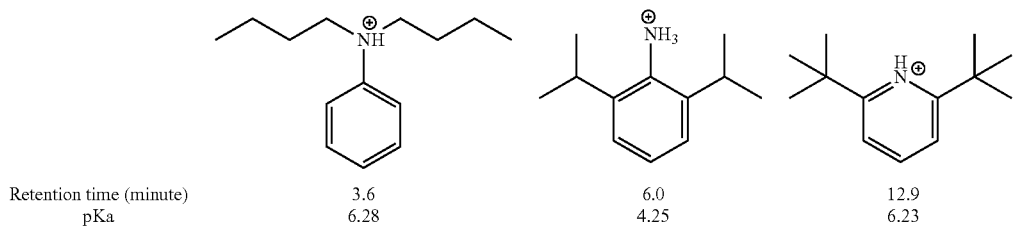

| Retention time (minute) | 3.6 | 6.0 | 12.9 |
| pKa | 6.28 | 4.25 | 6.23 |

Examples of the first ammonium cation having a pKa of 7 or less

[Chemical Formula 7]

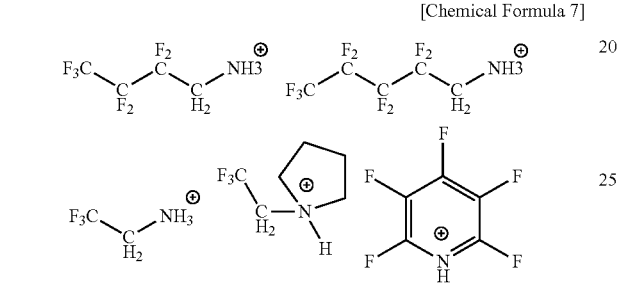

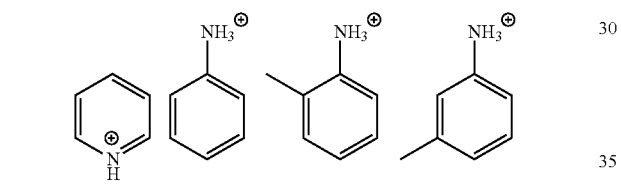

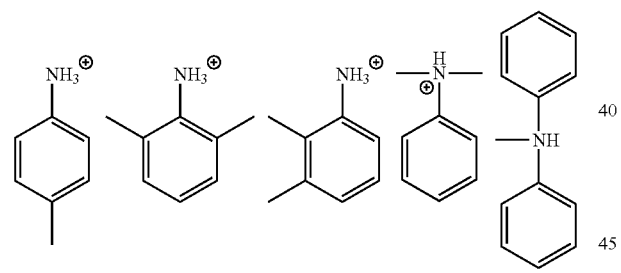

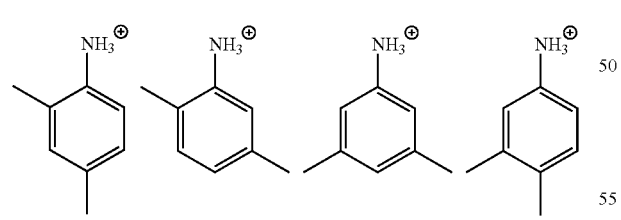

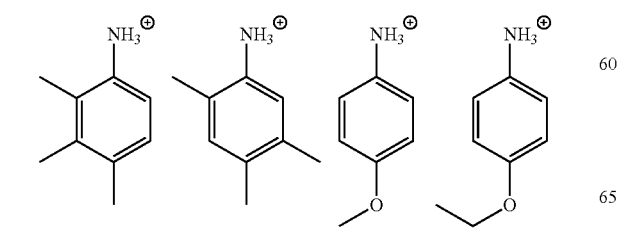

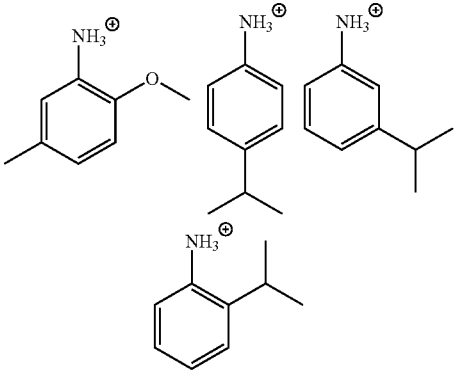

Anion moiety of first ammonium salt compound

The anion moiety of the first ammonium salt compound is not particularly limited, and organic cations such as a sulfonate anion, an amide anion, a methide anion and a carboxylate anion can be preferably used.

Sulfonate Anion

Examples of such a sulfonate anion include conventional sulfonate anions. In terms of the effect of improving the properties of the resist composition of the sixth aspect, specific examples thereof includes an anion represented by general formula (an1-1) shown below.

[Chemical Formula 8]

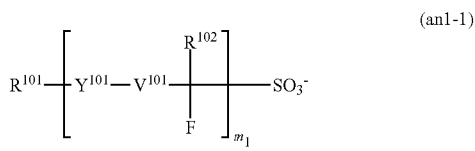

(an1-1)

In the formula, $R^{101}$ represents a cyclic group which may have a substituent, a chain-like alkyl group which may have a substituent or a chain-like alkenyl group which may have a substituent; $R^{102}$ represents a fluorine atom or a fluorinated alkyl group of 1 to 5 carbon atoms; $Y^{101}$ represents a single bond or a divalent linking group containing an oxygen atom or a sulfur atom; $V^{101}$ represents a single bond, an alkylene group or a fluorinated alkylene group; and $m_1$ represents 0 or 1.

In the formula (an1-1), $R^{101}$ represents a cyclic group which may have a substituent, a chain-like alkyl group which may have a substituent or a chain-like alkenyl group which may have a substituent.

(Cyclic Group which May have a Substituent)

The cyclic group is preferably a cyclic hydrocarbon group, and the cyclic hydrocarbon group may be either an aromatic hydrocarbon group or an aliphatic hydrocarbon group. An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

The aromatic hydrocarbon group for $R^{101}$ is a hydrocarbon group having an aromatic ring. The aromatic hydrocarbon group preferably has 5 to 30 carbon atoms, more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group for $R^{101}$ include benzene, biphenyl, fluorene, naphthalene, anthracene and phenanthrene; and aromatic hetero rings in which part of the carbon atoms constituting these aromatic rings has been substituted with a hetero atom. Examples of the hetero atom within the aromatic hetero rings include an oxygen atom, a sulfur atom and a nitrogen atom.

Specific examples of the aromatic hydrocarbon group for $R^{101}$ include a group in which one hydrogen atom has been removed from the aforementioned aromatic ring (aryl group such as a phenyl group and a naphthyl group); and a group in which one hydrogen atom of the aforementioned aromatic ring has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atoms, more preferably 1 or 2, and most preferably 1.

Examples of the cyclic aliphatic hydrocarbon group for $R^{101}$ include an aliphatic hydrocarbon group containing a ring in the structure thereof.

As examples of the aliphatic hydrocarbon group containing a ring in the structure thereof, an alicyclic hydrocarbon group (a group in which one hydrogen atom has been removed from an aliphatic hydrocarbon ring), a group in which the alicyclic hydrocarbon group is bonded to the terminal of a linear or branched aliphatic hydrocarbon group, and a group in which the alicyclic hydrocarbon group is interposed within a linear or branched aliphatic hydrocarbon group, can be given.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic group, a group in which one ore more hydrogen atoms have been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

Among these, as the cyclic aliphatic hydrocarbon group for $R^{101}$, a group in which one or more hydrogen atoms have been removed from a monocycloalkane or a polycycloalkane is preferable, and a group in which one hydrogen atom has been removed from a polycycloalkane is more preferable, an adamantyl group and a norbornyl group are particularly preferable, and an adamantyl group is most preferable.

The linear or branched aliphatic hydrocarbon group which may be bonded to the alicyclic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable, and specific examples include a methylene group [—$CH_2$—], an ethylene group [—($CH_2)_2$—], a trimethylene group [—($CH_2)_3$—], a tetramethylene group [—($CH_2)_4$—] and a pentamethylene group [—($CH_2)_5$—].

As the branched aliphatic hydrocarbon group, a branched alkylene group is preferable, and specific examples include alkylalkylene groups, e.g., alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

Further, the cyclic hydrocarbon group for $R^{101}$ may contains a hetero atom, like as a heterocycle. Specific examples thereof include lactone-containing cyclic groups represented by general formulae (a2-r-1) to (a2-r-7) described later, —$SO_2$— containing cyclic groups represented by formulae (a5-r-1) to (a5-r-4) described later and heterocycles shown below.

[Chemical Formula 9]

(r-hr-1)

(r-hr-2)

(r-hr-3)

(r-hr-4)

(r-hr-5)

(r-hr-6)

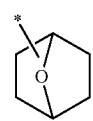 (r-hr-7)

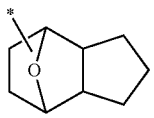 (r-hr-8)

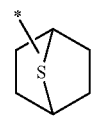 (r-hr-9)

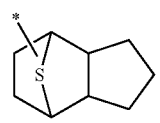 (r-hr-10)

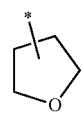 (r-hr-11)

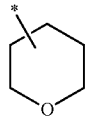 (r-hr-12)

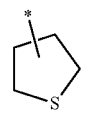 (r-hr-13)

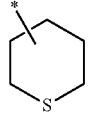 (r-hr-14)

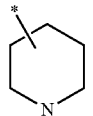 (r-hr-15)

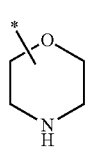 (r-hr-16)

As the substituent for substituting the cyclic hydrocarbon group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent include a fluorine atom, a chlorine atom, a bromine atom and an iodine atom, and a fluorine atom is preferable.

Example of the halogenated alkyl group as a substituent includes a group in which a part or all of the hydrogen atoms within an alkyl group of 1 to 5 carbon atoms such as a methyl group, an ethyl group, a propyl group, an n-butyl group or a tert-butyl group have been substituted with the aforementioned halogen atoms.

The carbonyl group as a substituent is a group to substitute a methylene group (—$CH_2$—) constituting a cyclic hydrocarbon group.

(Chain-like Alkyl Group which May have a Substituent)

The chain-like alkyl group for $R^{101}$ may be either linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

(Chain-like Alkenyl Group which May have a Substituent)

The chain-like alkenyl group for $R^{101}$ may be linear or branched, and preferably has 2 to 10 carbon atoms, more preferably 2 to 5 carbon atoms, still more preferably 2 to 4 carbon atoms, and particularly preferably 3 carbon atoms. Examples of linear alkenyl groups include a vinyl group, a propenyl group (an allyl group) and a butynyl group. Examples of branched alkenyl groups include a 1-methylvinyl group, 2-methylvinyl group, a 1-methylpropenyl group and a 2-methylpropenyl group.

Among the above-mentioned examples, as the chain-like alkenyl group, a vinyl group and a propenyl group are preferable, and a vinyl group is particularly desirable.

As the substituent for substituting the chain-like alkyl group or alkenyl group for $R^{101}$, an alkoxy group, a halogen atom, a halogenated alkyl group, a hydroxyl group, a carbonyl group, a nitro group, an amino group, the same cyclic group as described above for $R^{101}$ or the like can be used.

Among these, as the group for $R^{101}$, a cyclic group which may have a substituent and a chain-like alkenyl group which may have a substituent are preferable, and a cyclic hydrocarbon group which may have a substituent and a chain-like alkenyl group which may have a substituent are more preferable.

Specific examples include a group in which one or more hydrogen atoms have been removed from a phenyl group, a naphthyl group or a polycycloalkane, lactone-containing cyclic groups represented by formulae (a2-r-1) to (a2-r-7) described later, —$SO_2$-containing cyclic groups represented by formulae (a5-r-1) to (a5-r-4) described later; a vinyl group, a propenyl group and the like.

In the formula (an1-1), $Y^{101}$ represents a single bond or a divalent linking group containing an oxygen atom or a sulfur atom.

In the case where $Y^{101}$ is a divalent linking group containing an oxygen atom or a sulfur atom, $Y^{101}$ may contain an atom other than an oxygen atom or sulfur atom. Examples of atoms other than an oxygen atom or sulfur atom include a carbon atom, a hydrogen atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—, —O—C(=O)—), an oxycarbonyl group (—O—C(=O)—), an amide bond (—C(=O)—NH—), a carbonyl group (—C(=O)—) and a carbonate group (—O—C(=O)—O—); and a combination of any of the aforementioned non-hydrocarbon, oxygen atom-containing linking groups with an alkylene group. Furthermore, the combinations may have a sulfonyl group (—SO$_2$—) bonded thereto.

As the combination, the linking groups represented by formulae (y-a1-1) to (y-a1-7) shown below can be mentioned.

[Chemical Formula 10]

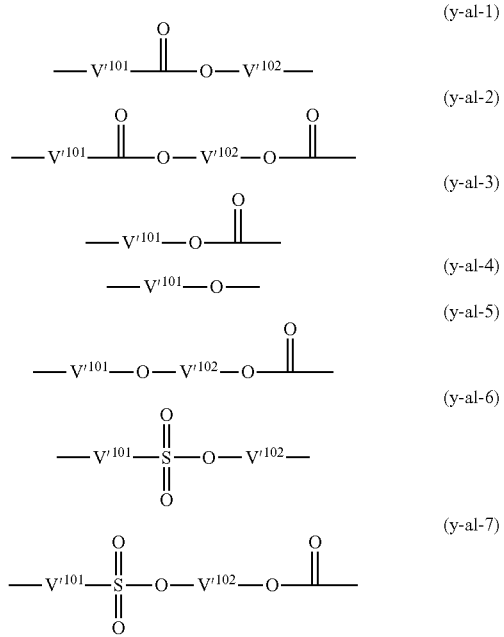

In the formulae, $V'^{101}$ represents a single bond or an alkylene group of 1 to 5 carbon atoms; and $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms.

As the alkylene group for $V'^{101}$ and $V'^{102}$, a linear alkylene group or a branched alkylene group can be used, and a linear alkylene group is preferable.

Specific examples of the alkylene group for $V'^{101}$ and $V'^{102}$ include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

Further, part of methylene group within the alkylene group for $V'^{101}$ and $V'^{102}$ may be substituted with a divalent aliphatic cyclic group of 5 to 10 carbon atoms. Examples of the aliphatic cyclic group include a divalent group in which one hydrogen atom has been removed from the alicyclic hydrocarbon group (a group in which one hydrogen atom has been removed from the aliphatic hydrocarbon ring) described above as a cyclic aliphatic hydrocarbon group for $R^{101}$. As the aliphatic hydrocarbon ring, cyclohexane, norbornane and adamantane are preferable. Specific examples of such groups include a cyclohexylene group, a 1,5-adamantylene group and a 2,6-adamantylene group.

As $Y^{101}$, an ester bond, an ester bond (—C(=O)—O—, —O—C(=O)—), a divalent linking group containing an ester bond or a divalent linking group containing an ether bond is preferable, an ester bond (—C(=O)—O—, —O—C(=O)—) or a linking group represented by any one of the general formulae (y-a1-1) to (y-a1-5) is more preferable, and an ester bond (—C(=O)—O—, —O—C(=O)—) is particularly preferable.

In the formula (an1-1), $V^{101}$ represents a single bond, an alkylene group or a fluorinated alkylene group. The alkylene group or fluorinated alkylene group for $V^{101}$ preferably has 1 to 4 carbon atoms. As the fluorinated alkylene group for $V^{101}$, a group in which part or all of the hydrogen atoms within the aforementioned alkylene group for $V^{101}$ has been substituted with fluorine atoms can be used. Among these, $V^{101}$ is preferably a single bond, an alkylene group of 1 to 4 carbon atoms or a fluorinated alkylene group of 1 to 4 carbon atoms, and a single bond and an alkylene group of 1 to 4 carbon atoms is more preferable.

In the formula (an1-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and is more preferably a fluorine atom.

As specific examples of anions represented by the general formula (an1-1), when $Y^{101}$ is a single bond, fluorinated alkylsulfonate anions such as a trifluoromethanesulfonate anion or a perfluorobutanesulfonate anion can be mentioned.

When $Y^{101}$ is a divalent linking group containing an oxygen atom, anions represented by formulae (an1-1-1) to (an1-1-3) shown below can be mentioned.

[Chemical Formula 11]

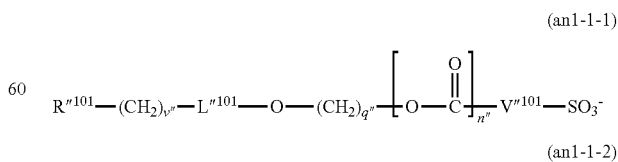

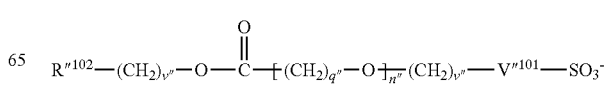

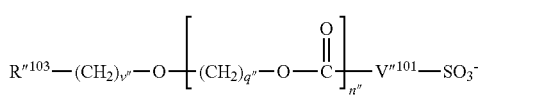
(an1-1-3)

In the formulae, $R''^{101}$ represents an aliphatic cyclic group which may have a substituent, a group represented by any one of the aforementioned formulae (r-hr-1) to (r-hr-6) or a chain-like alkyl group which may have a substituent; $R''^{102}$ represents an aliphatic cyclic group which may have a substituent, a lactone-containing cyclic group represented by any one of formulae (a2-r-1) to (a2-r-7) described later or an $-SO_2$-containing cyclic group represented by any one of formulae (a5-r-1) to (a5-r-4) described later; $R''^{103}$ represents an aromatic cyclic group which may have a substituent, an aliphatic cyclic group which may have a substituent or a chain-like alkenyl group which may have a substituent; $V''^{101}$ represents a fluorinated alkylene group; $L''^{101}$ represents $-C(=O)-$ or $-SO_2-$; v" each independently represents an integer of 0 to 3; q" each independently represents an integer of 1 to 20; n" represents 0 or 1.

As the aliphatic cyclic group for $R''^{101}$, $R''^{102}$ and $R''^{103}$ which may have a substituent, the same groups exemplified as the cyclic aliphatic hydrocarbon group for $R^{101}$ in the formula (an1-1) are preferable. As the substituent, the same groups as those described above for substituting the cyclic aliphatic hydrocarbon group for $R^{101}$ can be mentioned.

As the aromatic cyclic group for $R''^{103}$ which may have a substituent, the same groups as the aromatic hydrocarbon group exemplified as a cyclic hydrocarbon group for $R^{101}$ described above are preferable. As the substituent, the same groups as those described above for substituting the aromatic hydrocarbon group for $R^{101}$ can be mentioned.

As the chain-like alkyl group for $R''^{101}$ which may have a substituent, the same groups exemplified as the chain-like alkyl group for $R^{101}$ are preferable. As the chain-like alkenyl group for $R''^{103}$ which may have a substituent, the same groups exemplified as the chain-like alkenyl group for $R^{101}$ are preferable.

$V''^{101}$ is preferably a fluorinated alkylene group of 1 to 3 carbon atoms, and particularly preferably $-CF_2-$, $-CF_2CF_2-$, $-CHFCF_2-$, $-CF(CF_3)CF_2-$ or $-CH(CF_3)CF_2-$.

Specific examples of the anion moieties represented by the aforementioned formulae (an1-1-1) to (an1-1-3) and specific examples of the anion moieties represented by the aforementioned formula (an1-1) in which $m_1$ is 0 are shown below, but are not limited to these anion moieties.

[Chemical Formula 12]

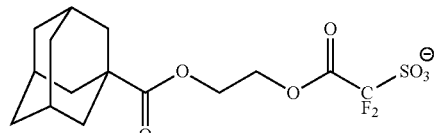

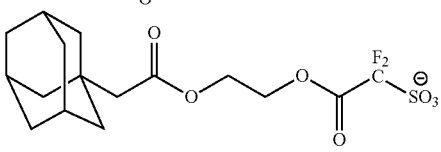

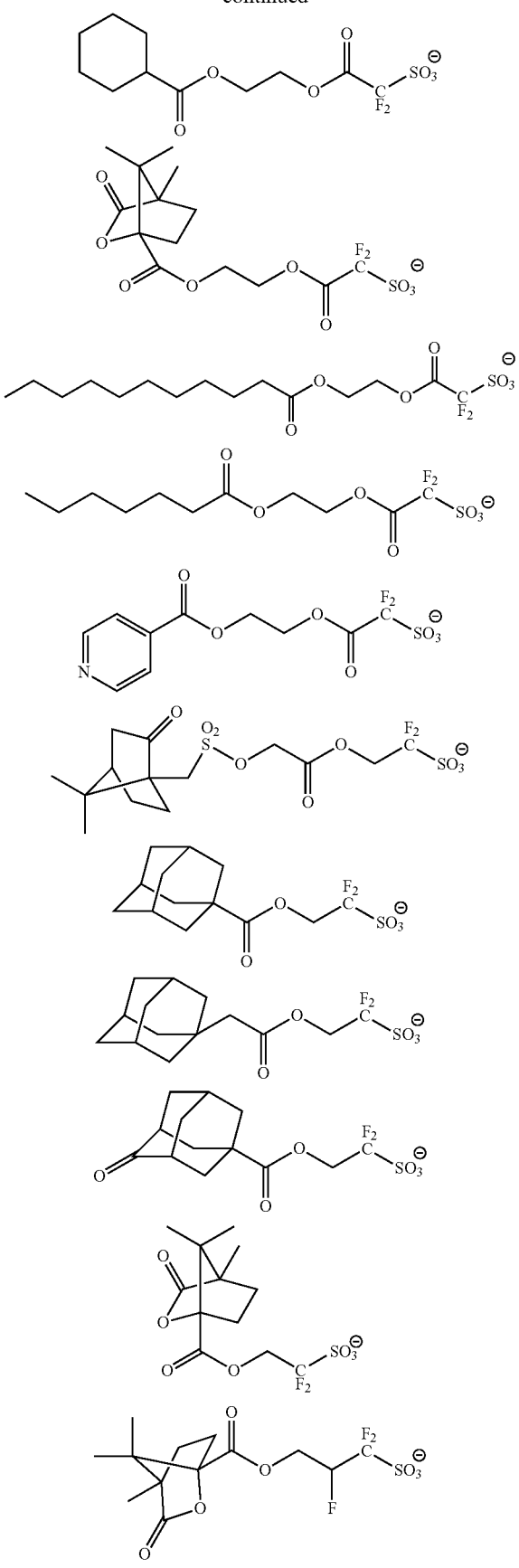

-continued

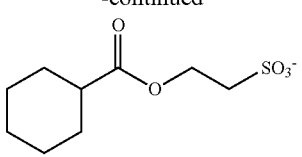
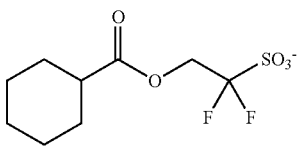
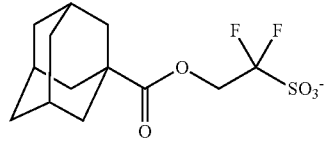
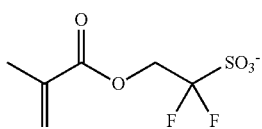

Specific examples of the anion moieties represented by the formula (an1-1-1)

Specific examples of the anion moieties represented by the formula (an1-1-2)

[Chemical Formula 13]

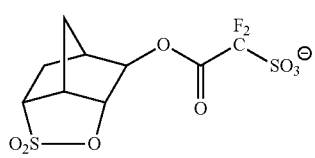
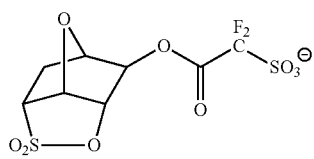
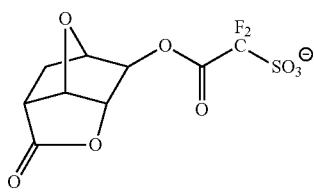
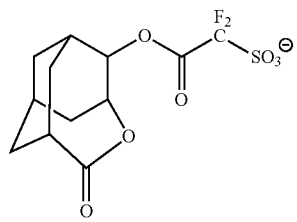
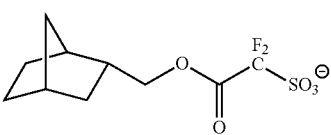

-continued

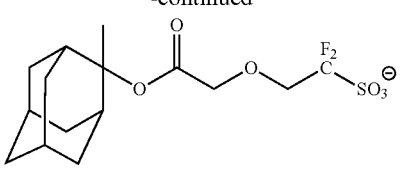

Specific examples of the anion moieties represented by the formula (an1-1-3)

[Chemical Formula 14]

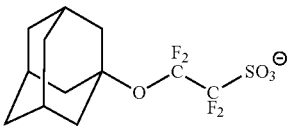
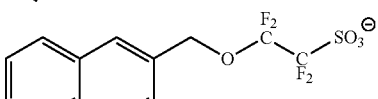
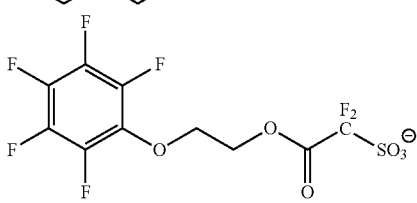
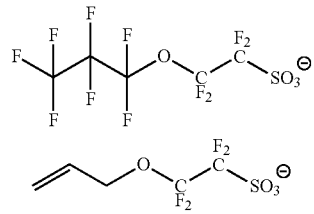
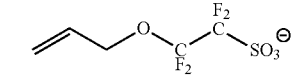

Specific examples of the anion moieties represented by the formula (an1-1) in which $m_1$ is 0

[Chemical Formula 15]

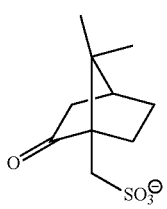
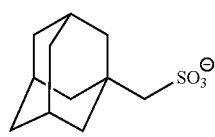
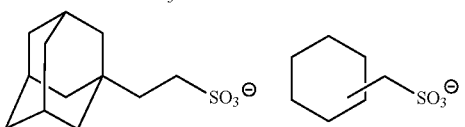
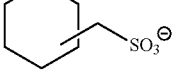
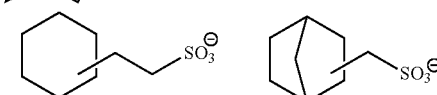
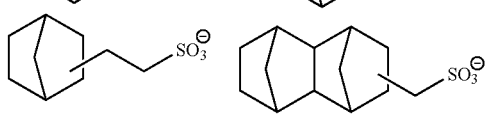

-continued

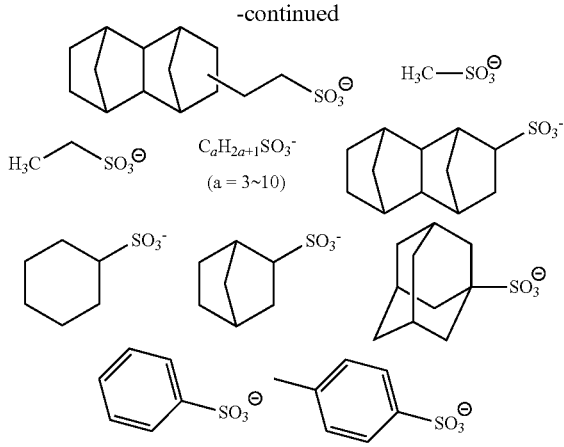

Amide anion

Examples of such an amide anion include conventional amide anions such as a carbonylamide anion, a carbonylimide anion, a sulfonylamide anion, a sulfonylimide anion and the like. In terms of the effect of improving the properties of the resist composition of the sixth aspect, specific examples thereof includes an anion represented by general formula (an1-2) shown below.

[Chemical Formula 16]

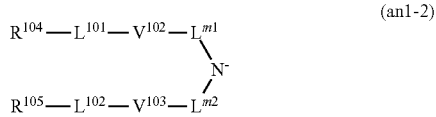
(an1-2)

In the formula, $R^{104}$ and $R^{105}$ each independently represents a cyclic group which may have a substituent, a chain-like alkyl group which may have a substituent or a chain-like alkenyl group which may have a substituent, $R^{104}$ and $R^{105}$ may be mutually bonded to form a ring; and $V^{102}$ and $V^{103}$ each independently represents a single bond, an alkylene group or a fluorinated alkylene group; $L^{101}$ and $L^{102}$ each independently represents a single bond or an oxygen atom; $L^{m1}$ represents —$SO_2$—, —C(=O)— or a single bond; and $L^{m2}$ represents —$SO_2$— or —C(=O)—.

In formula (an1-2), $R^{104}$ and $R^{105}$ each independently represents a cyclic group which may have a substituent, a chain-like alkyl group which may have a substituent or a chain-like alkenyl group which may have a substituent, and is the same groups as those defined above for $R^{101}$ in the aforementioned formula (an1-1), provided that, $R^{104}$ and K may be mutually bonded to form a ring.

Among these, as $R^{104}$ and $R^{105}$, a chain-like alkyl group which may have a substituent or a cyclic group which may have a substituent is preferable.

As the chain-like alkyl group for $R^{104}$ and $R^{105}$ which may have a substituent, a linear or branched alkyl group or a linear or branched fluorinated alkyl group is more preferable.

The chain-like alkyl group preferably has 1 to 10 carbon atoms, preferably 1 to 7, and more preferably 1 to 3. The smaller the number of carbon atoms of the chain-like alkyl group for $R^{104}$ and $R^{105}$ within the above-mentioned range of the number of carbon atoms, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

The cyclic group for $R^{104}$ and $R^{105}$ which may have a substituent is more preferably a cyclic aliphatic hydrocarbon group, and particularly preferably an alicyclic hydrocarbon group (group in which one hydrogen atom has been removed from the aliphatic hydrocarbon ring). Specific examples thereof include a monocyclic alicyclic hydrocarbon group and a polycyclic alicyclic hydrocarbon group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic group, a group in which one or more hydrogen atoms have been removed from a polycycloalkane is preferable, and the polycycloalkane preferably has 7 to 12 carbon atoms. Examples of the polycycloalkane include adamantane, norbornane, isobornane, tricyclodecane and tetracyclododecane. These monocycloalkane and polycycloalkane may have a substituent, and as a cyclic structure having a substituent, camphor can be mentioned.

In formula (an1-2) $V^{102}$ and $V^{103}$ each independently represents a single bond, an alkylene group or a fluorinated alkylene group, and is the same groups as those defined above for $V^{101}$ in the aforementioned formula (an1-1).

In the formula (an1-2), $L^{101}$ and $L^{102}$ each independently represents a single bond or an oxygen atom.

Specific examples of the anion moieties represented by the formula (an1-2) in which $L^{m1}$ is not a single bond are shown below, but are not limited to these anion moieties.

{Chemical Formula 17]

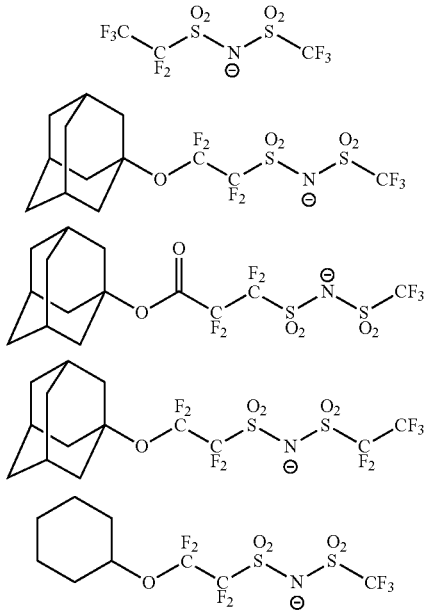

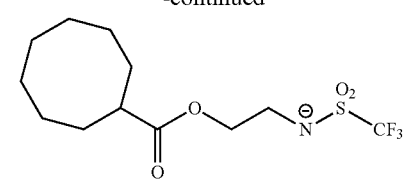
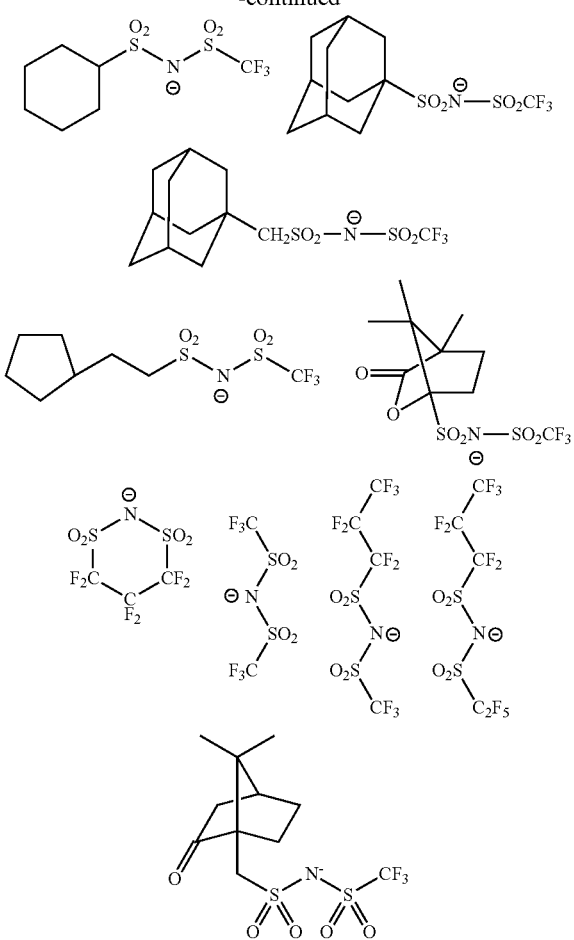
Specific examples of the anion moieties represented by the formula (an1-2) in which $L^{m1}$ is a single bond are shown below, but are not limited to these anion moieties.
[Chemical Formula 18]
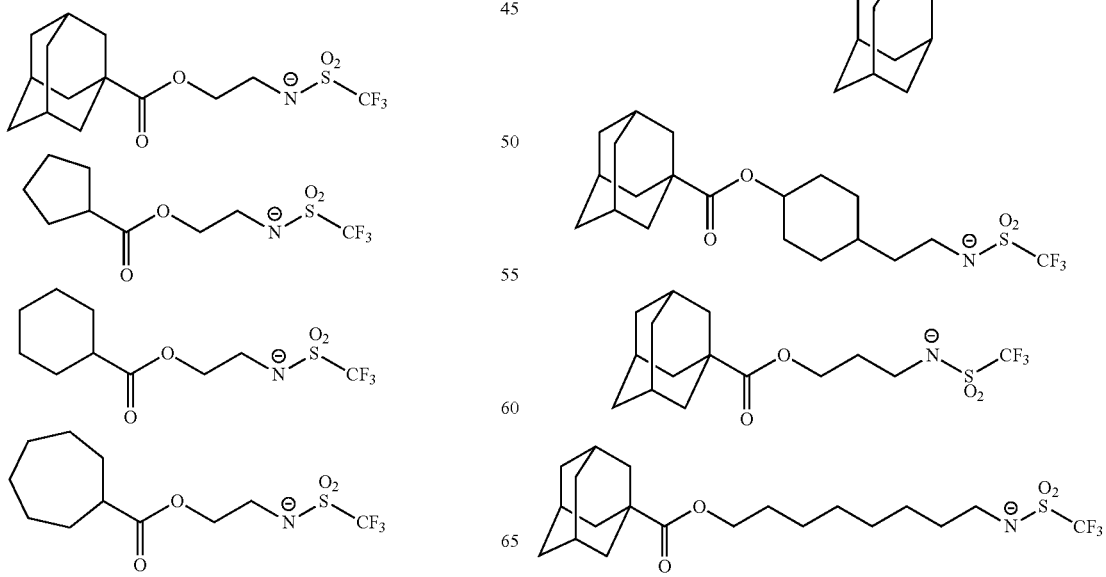

-continued

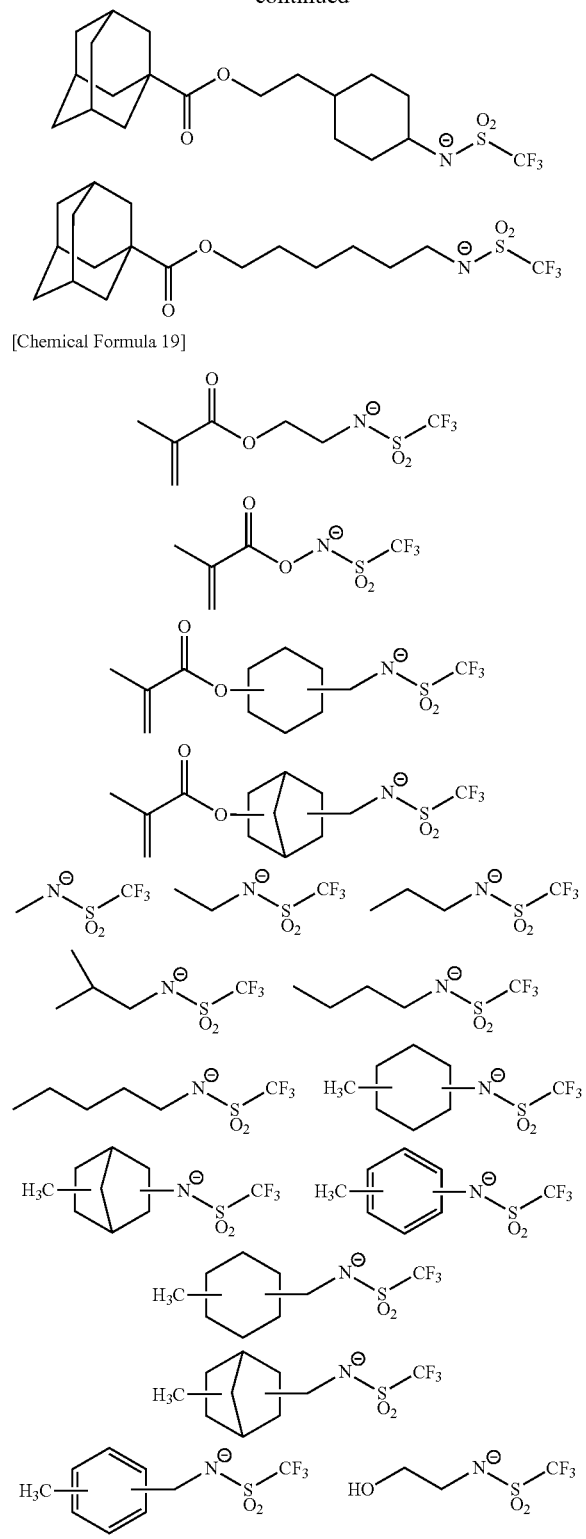

[Chemical Formula 19]

Methide Anion

Examples of such a methide anion include conventional methide anions. In terms of the effect of improving the properties of the resist composition of the sixth aspect, specific examples thereof includes an anion represented by general formula (an1-3) shown below.

[Chemical Formula 20]

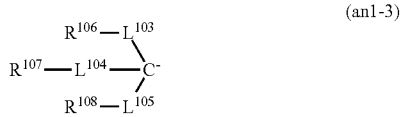

(an1-3)

In the formula, $R^{106}$ to $R^{108}$ each independently represents a cyclic group which may have a substituent, a chain-like alkyl group which may have a substituent or a chain-like alkenyl group which may have a substituent, two of $R^{106}$ to $R^{108}$ may be mutually bonded to form a ring; and $L^{103}$ to $L^{105}$ each independently represents a single bond, —CO— or —SO$_2$—.

In formula (an1-3), $R^{106}$ and $R^{108}$ each independently represents a cyclic group which may have a substituent, a chain-like alkyl group which may have a substituent or a chain-like alkenyl group which may have a substituent, and is the same groups as those defined above for $R^{101}$ in the aforementioned formula (an1-1), provided that, two of $R^{106}$ to $R^{108}$ may be mutually bonded to form a ring. Among these, as $R^{106}$ to $R^{108}$, a chain-like alkyl group which may have a substituent or a cyclic group which may have a substituent is preferable.

As the chain-like alkyl group for $R^{106}$ to $R^{108}$ which may have a substituent, a linear or branched alkyl group or a linear or branched fluorinated alkyl group is preferable, and a linear or branched fluorinated alkyl group is more preferable.

The chain-like alkyl group preferably has 1 to 10 carbon atoms, preferably 1 to 7, and more preferably 1 to 3. The smaller the number of carbon atoms of the chain-like alkyl group within the above-mentioned range of the number of carbon atoms, the more the solubility in a resist solvent is improved. Further, in the chain-like alkyl group, it is preferable that the number of hydrogen atoms substituted with fluorine atoms is as large as possible because the acid strength increases and the transparency to high energy radiation of 200 nm or less or electron beam is improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

The cyclic group for $R^{106}$ to $R^{108}$ which may have a substituent is more preferably a cyclic aliphatic hydrocarbon group, and particularly preferably an aromatic hydrocarbon group (hydrocarbon group having an aromatic ring). The aromatic hydrocarbon group preferably has 5 to 30 carbon atoms, more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group for $R^{106}$ to $R^{108}$ include benzene, biphenyl, fluorene, naphthalene, anthracene and phenanthrene; and aromatic hetero rings in which part of the carbon atoms constituting these aromatic rings has been substituted with a hetero atom. Examples of the hetero atom within the aromatic hetero rings include an oxygen atom, a sulfur atom and a nitrogen atom.

Specific examples of the aromatic hydrocarbon group for $R^{106}$ to $R^{108}$ include a group in which one hydrogen atom has been removed from the aforementioned aromatic ring (aryl group such as a phenyl group and a naphthyl group); and a group in which one hydrogen atom of the aforementioned aromatic ring has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atoms, more preferably 1 or 2, and most preferably 1.

In the formula (an1-3), $L^{103}$ to $L^{105}$ each independently represents a single bond, —CO— or —SO$_2$—.

Specific examples of the anion moieties represented by the formula (an1-3) are shown below, but are not limited to these anion moieties.

[Chemical Formula 21]

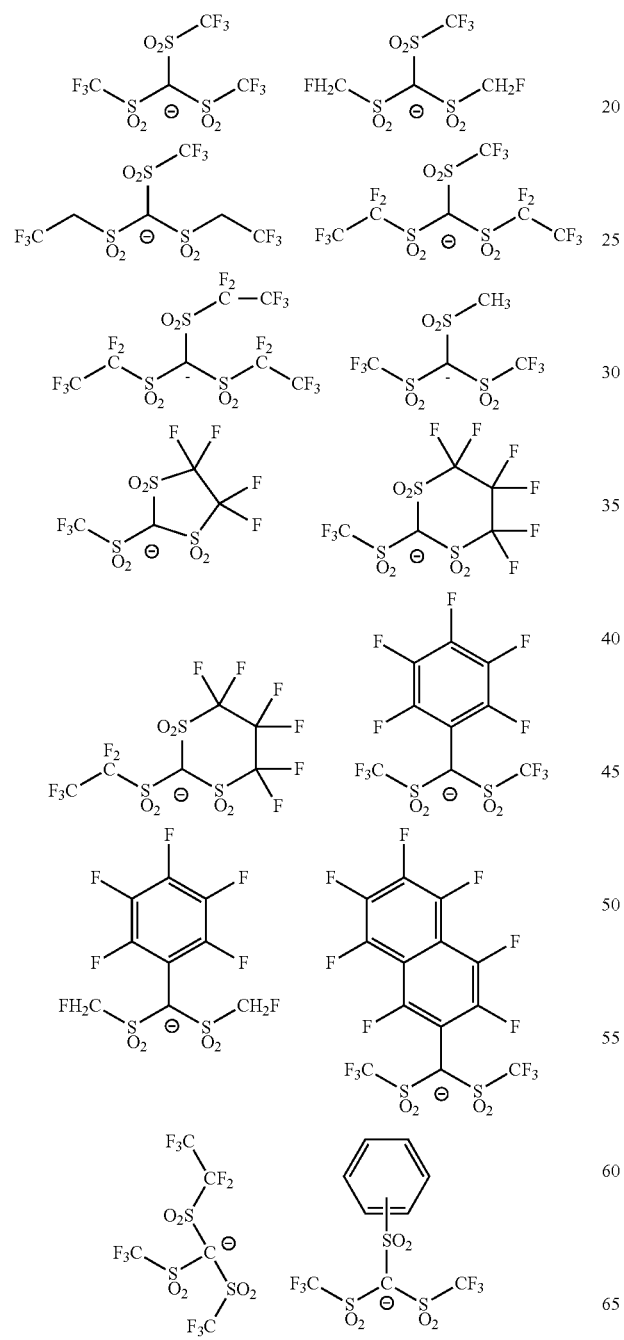

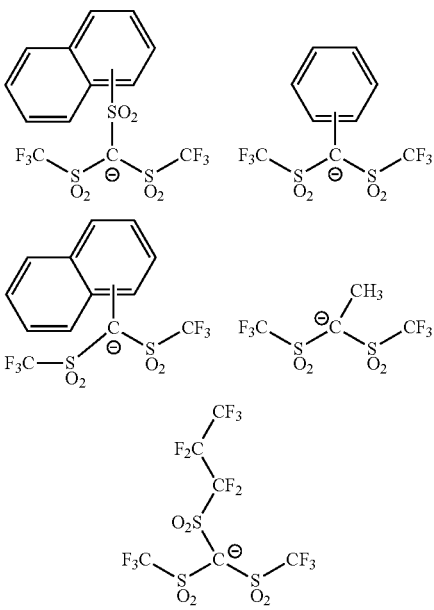

Carboxylate Anion

Examples of such a carboxylate anion include conventional carboxylate anions. In terms of the effect of improving the properties of the resist composition of the sixth aspect, specific examples thereof includes an anion represented by general formula (an1-4) shown below.

[Chemical Formula 22]

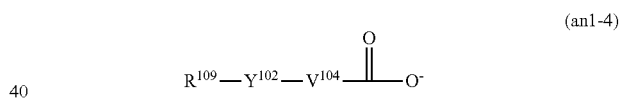

(an1-4)

In the formula, $R^{109}$ represents a cyclic group which may have a substituent, a chain-like alkyl group which may have a substituent or a chain-like alkenyl group which may have a substituent; $Y^{102}$ represents a single bond or a divalent linking group containing an oxygen atom or a sulfur atom; and $V^{104}$ represents a single bond, an alkylene group or a fluorinated alkylene group.

In formula (an1-4), $R^{109}$ represents a cyclic group which may have a substituent, a chain-like alkyl group which may have a substituent or a chain-like alkenyl group which may have a substituent, and is the same groups as those defined above for $R^{101}$ in the aforementioned formula (an1-1).

Among these, as $R^{109}$, a chain-like alkyl group which may have a substituent is preferable.

As the chain-like alkyl group for $R^{109}$ which may have a substituent, a linear or branched alkyl group is more preferable. The chain-like alkyl group preferably has 1 to 10 carbon atoms, preferably 1 to 7, and more preferably 1 to 3.

In the formula (an1-4), $Y^{102}$ and $V^{104}$ are the same as defined above for $Y^{101}$ and $V^{101}$ in the formula (an1-1).

Specific examples of the anion moieties represented by the formula (an1-4) are shown below, but are not limited to these anion moieties.

[Chemical Formula 23]

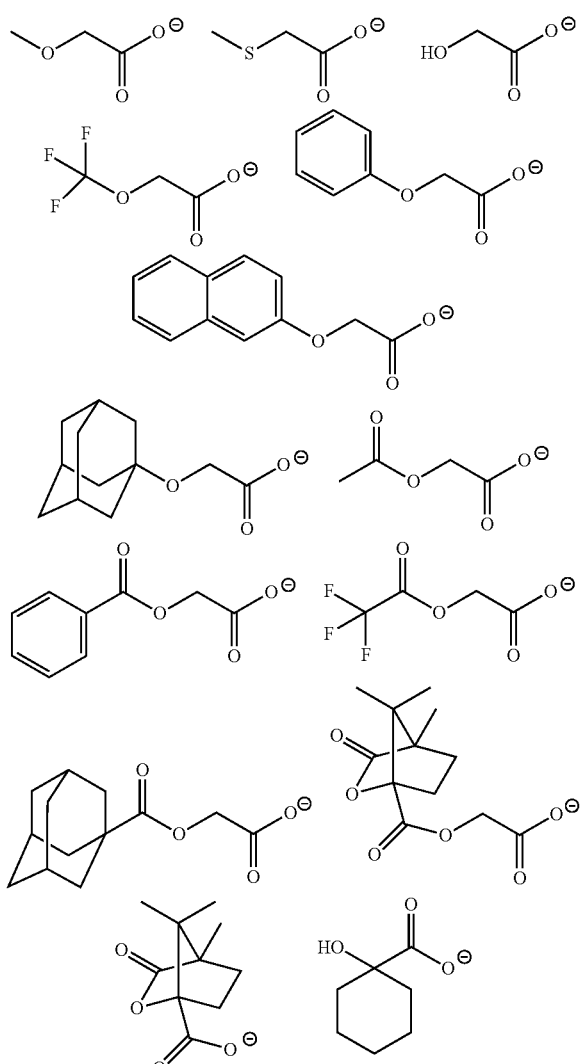

[Chemical Formula 24]

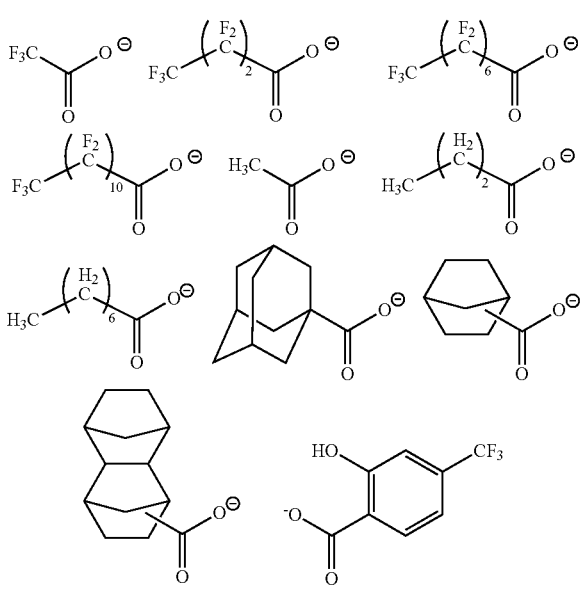

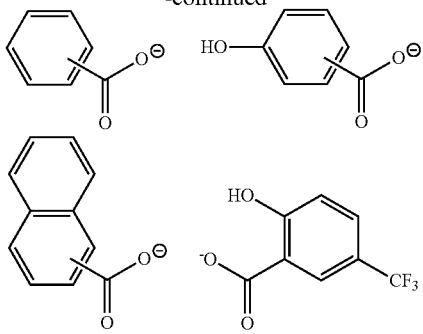

In terms of the effect of improving the properties of the resist composition of the sixth aspect, as the anion moiety for the first ammonium salt compound, a sulfonate anion, an amide anion, a methide anion or a carboxylate anion is preferable.

(Reaction Between First Ammonium Salt Compound and Nitrogen-Containing Compound)

For example, the reaction between the nitrogen-containing compound and the first ammonium salt compound is conducted in an organic solvent. The first ammonium salt compound reacts with the nitrogen-containing compound in an organic solvent, thereby replacing the first ammonium cation of the first ammonium salt compound with a conjugated acid of the nitrogen-containing compound (i.e., second ammonium cation) to obtain a second ammonium salt compound containing the second ammonium cation.

The amount of the first ammonium salt compound and the amount of the nitrogen-containing compound can be appropriately determined, taking into consideration the amount of the first ammonium cation of the first of the ammonium salt compound.

The reaction temperature is preferably 0 to 50° C., and more preferably 10 to 30° C.

The reaction time varies, depending on the reactivity of the first ammonium salt compound and nitrogen-containing compound, the reaction temperature, and the like. However, in general, the reaction time is preferably 5 minutes to 24 hours, more preferably 10 to 120 minutes, and still more preferably 10 to 60 minutes.

The organic solvent may be any organic solvents which contain a component capable of dissolving both of the first ammonium salt compound and nitrogen-containing compound. In particular, it is preferable that a good solvent that dissolves the obtained second ammonium salt compound and a poor solvent that does not dissolve the second ammonium salt compound are used in combination.

Examples of the good solvent include acetonitrile, dimethyl sulfoxide, N,N-dimethylformamide, methanol and the like.

Examples of the poor solvent include hydrocarbon solvents such as n-heptane, n-hexane or the like, and ether solvents such as tert-butyl methyl ether, diisopropyl ether or the like.

After reaction between the first ammonium salt compound and the nitrogen-containing compound, either by washing the reaction solution (e.g., good solvent phase in the case where a good solvent and a poor solvent are used in combination) with a poor solvent, followed by removing the solvent, or by adding the reaction solution to an excess amount of an organic solvent (e.g., diisopropanol, heptane, methanol) in a dropwise manner so as to precipitate the compound, followed by separating the precipitated compound by filtration, the second ammonium salt compound can be obtained.

In the method of producing an ammonium salt compound of the present invention, the reaction between the nitrogen-containing compound and first ammonium salt compound is a reaction including the transfer of a proton (H$^+$), and is different from a reaction such as a salt exchange reaction. The reaction equilibrium thereof is more biased in the forward direction than that of the salt exchange reaction. Therefore, the amount of the nitrogen-containing compound can be reduced. As a result, it is possible to reduce unreacted raw materials and to obtain a second ammonium salt compound with high purity.

Further, by using the difference in pKa value, that is, by reacting a first ammonium salt compound and a nitrogen-containing compound capable of forming a conjugated acid which has a larger pKa value than that of the first ammonium cation, a second ammonium salt compound having the conjugated acid (i.e., second ammonium cation) can be obtained, wherein the conjugated acid has a lower hydrophobicity than that of a cation moiety (a sulfonium cation, an iodonium cation and the like) of an acid generator for a resist composition. As a result, for example, when an acid generator for a resist composition is produced, salt exchange for introducing a desired cation moiety (a sulfonium cation, an iodonium cation and the like) satisfactorily proceeds. Further, when the hydrophobicity of the first ammonium cation is high, as described later, since it is advantageous to remove impurities by wash treatment, yield can be increased.

[Step of Obtaining First Ammonium Salt Compound]

As a method of producing a first ammonium salt compound, a method in which salt exchange between a first ammonium cation and a compound (P) containing a cation which has a lower hydrophobicity than the hydrophobicity of the first ammonium cation is conducted, or a method in which only the counteranion moiety to be paired with the first ammonium cation is appropriately synthesized without conducting salt exchange of cation moiety, can be mentioned.

In the method of producing an ammonium salt compound of the present invention, it is preferable that the first ammonium salt compound is obtainable by the former method, that is, obtainable by conducting salt exchange between the first ammonium cation and the compound (P) containing a cation which has a lower hydrophobicity than the hydrophobicity of the first ammonium cation. In the case of the former method, it is advantageous in that impurities such as byproducts produced in the synthesis of compound (P) can be easily removed by wash treatment, and the yield can be improved.

The salt exchange reaction between the compound (P) and the first ammonium cation is preferably conducted in a two-phase reaction system of water and an organic solvent.

In this step, for example, by mixing the compound (P) and a salt containing the first ammonium cation in a mixed solvent of an organic solvent and water, a first ammonium salt compound can be obtained.

(Salt Containing First Ammonium Cation)

The first ammonium cation is the same cation moiety as those described above for the first ammonium cation within the aforementioned first ammonium salt compound, and the hydrophobicity thereof is higher than that of a cation moiety of a compound (P).

The salt containing the first ammonium cation is a compound capable of conducting salt exchange between the first ammonium cation within the salt and the compound (P). That is, the first ammonium cation of the salt becomes the cation moiety of the first ammonium salt compound.

It is preferable that the salt containing the first ammonium salt is a compound composed of an cation moiety (which is the first ammonium cation) and an anion moiety (which is a non-nucleophilic ion).

Examples of non-nucleophilic ions include a halogen ion such as a bromine ion or a chlorine ion; an ion capable of forming an acid exhibiting a lower acidity than the compound (P); BF$_4^-$, AsF$_6^-$, SbF$_6^-$, PF$_6^-$ and ClO$_4^-$. The ion capable of forming an acid exhibiting a lower acidity than the compound (P) is not particularly limited, and examples thereof include sulfonate ions such as a p-toluenesulfonate ion, a methanesulfonate ion and a benzenesulfonate ion.

(Compound (P))

The compound (P) contains a cation which has a lower hydrophobicity than that of the first ammonium cation.

In the step of obtaining first ammonium salt compound, by conducting salt exchange reaction so as to replace a cation moiety having a low hydrophobicity with a cation moiety having a high hydrophobicity, salt exchange can satisfactorily proceeds. As a result, a first ammonium salt compound containing a desired first ammonium cation can be produced.

The cation moiety of compound (P) is not particularly limited, as long as the retention time thereof is shorter than that of the first ammonium cation, wherein the retention time is measured under the specific condition in accordance with the aforementioned HPLC method. For example, the retention time of the cation moiety of compound (P) is preferably 0.5 to 10 minutes, more preferably 1 to 5 minutes, and still more preferably 1 to 3 minutes. When the retention time is at least as large as the lower limit of the above-mentioned range, the component (P) exhibits excellent solubility in an organic solvent, and can be readily synthesized. On the other hand, when the retention time is no more than the upper limit of the above-mentioned range, salt exchange reaction for providing a first ammonium salt compound easily proceeds.

As a cation moiety of the compound (P), a metal cation, an ammonium ion, H$^+$, a phosphonium ion and an other inorganic cation can be mentioned, and the cation moiety can be selected appropriately, depending on the level of hydrophobicity of the first ammonium cation.

As the metal ion, an alkali metal ion is preferably used. Examples of the alkali metal ion include sodium ion, potassium ion and the like.

As the ammonium ion, an ammonium ion other than the first ammonium cation can be selected appropriately, and examples thereof include ammonium ion (NH$_4^+$), a quaternary ammonium ion, a primary ammonium ion, a secondary ammonium ion and a tertiary ammonium ion.

Examples of the quaternary ammonium ion include tetramethylammonium ion, tetraethylammonium ion (Et$_4$N$^+$), trimethylethylammonium ion (Me$_3$EtN$^+$), other tetraalkylammonium ions in which the total number of carbon atoms is 10 or less, and a quaternary ammonium ion represented by chemical formulae shown below.

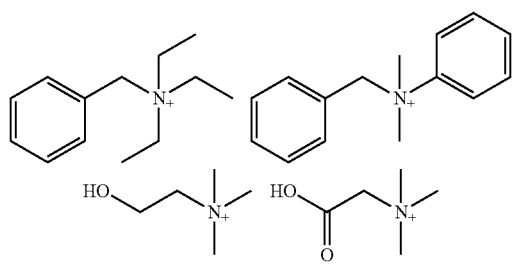

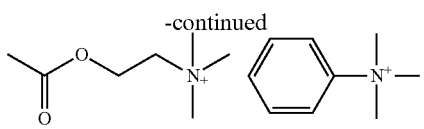

Examples of the primary ammonium ion, secondary ammonium ion and tertiary ammonium ion include methylammonium ion, dimethylammonium ion, trimethylammonium ion, ethylammonium ion, diethylammonium ion, triethylammonium ion, n-propyl ammonium ion, di-n-propylammonium ion, tri-n-propylammonium ion, i-propylammonium ion, di-1-propylammonium ion, tri-1-propylammonium ion, diisopropyl-ethylammonium ion, phenylammonium ion and the like.

Further, it is necessary that there is a certain difference in retention time between the cation moiety of compound (P) and the first ammonium cation, wherein the retention time can be measured in accordance with the aforementioned HPLC method. The value obtained by dividing the retention time of the first ammonium cation by the retention time of the cation moiety of compound (P) is greater than 1, more preferably 1.1 or more, and still more preferably 1.2 or more. When the value is 1.1 or more, salt exchange easily proceeds.

Examples of the anion moiety of the compound (P) include an organic anion. That is, it is preferable that the compound (P) is a salt containing an organic anion and a cation which has a lower hydrophobicity than the hydrophobicity of the first ammonium cation.

As the organic anion, the same anions as those exemplified for anion moiety of the first ammonium salt compound can be mentioned. Among these, in terms of the effect of improving the properties of the resist composition of the sixth aspect, a sulfonate anion, an amide anion, a methide anion or a carboxylate anion is preferable.

That is, as the compound (P), a compound in which the first ammonium cation of the first ammonium salt compound has been replaced by a metal ion, ammonium ion, $H^+$, a phosphonium ion or an other inorganic cation, can be mentioned.

When the compound (P) is mixed with the salt containing the first ammonium cation, as an organic solvent which constitutes a mixed solvent with water, an organic solvent capable of liquid separation from water, and dissolving the first ammonium salt compound can be used. Examples thereof include ketone solvents such as cyclohexanone, methyl ethyl ketone and diethyl ketone; ether solvents such as diethyl ether, t-butyl methyl ether and diisopropyl ether; tetrahydrofuran; 1,3-dioxolane; halogenated solvents such as dichloromethane and 1,2-dichloroethane; ester solvents such as ethyl acetate and propylene glycol monomethyl ether acetate; propionitrile; and a mixed solvent thereof.

In the step of obtaining a first ammonium salt compound, the temperature condition during salt exchange is preferably 0 to 50° C., and more preferably 10 to 30° C. The mixing time for conducting salt exchange depends on the temperature condition or the reactivity of the compound (P) and the salt containing the first ammonium cation, and the mixing time is preferably 0.5 minutes to 24 hours, more preferably 5 minutes to 12 hours, and still more preferably 10 to 60 minutes.

The amount of the salt containing the first ammonium cation is preferably 1 to 5 mol, per 1 mole of the compound (P).

In the step of obtaining a first ammonium salt compound, after mixing a compound (P) and a salt containing a first ammonium cation, or while mixing a compound (P) and a salt containing a first ammonium cation, wash treatment may be conducted.

The first ammonium salt compound obtained in this step has a higher hydrophobicity than that of the cation moiety of the compound (P). By virtue of its higher hydrophobicity, when wash treatment is conducted, the first ammonium salt compounds is less likely to be eluted in wash solution (poor solvent) from organic phase (good solvent). As a result, impurities such as unreacted materials, metal ions, byproducts and the like can be removed by wash treatment. Further, the first ammonium salt compound is less likely to be eluted in wash solution, and therefore, the yield of product obtained in the reaction of the first ammonium salt compound and the nitrogen-containing compound can be improved. Therefore, it is preferable that the first ammonium salt compound is obtainable by conducting salt exchange between the first ammonium cation and the compound (P), and conducting washing treatment.

Further, by using the first ammonium salt compound, the purity and yield of the second ammonium salt compound obtainable in the reaction with the nitrogen-containing compound, or the purity and yield of the compound (acid generator) obtainable by conducting salt exchange of the second ammonium salt compound can be improved. Moreover, by using a resist composition containing an acid generator having hardly any impurities, lithography properties in the formation of a resist pattern can be improved. Further, with respect to the compound containing a cation moiety having a low hydrophobicity (i.e., first ammonium salt compound), impurity can be easily removed by wash treatment, as compared to the compound containing a cation moiety having a high hydrophobicity (i.e., compound (acid generator) obtainable by conducting salt exchange of the second ammonium salt compound). Therefore, by conducting wash treatment before salt exchange reaction between the second ammonium salt compound and a cation moiety having a high hydrophobicity (e.g., sulfonium cation or iodonium cation), impurities can be preferably reduced.

As a method of wash treatment, disperse washing, washing after redissolution and reprecipitation and liquid-liquid washing can be preferably used.

As an organic solvent used in disperse washing, a polar solvent is preferable, and for example, alcohol solvents such as methanol and isopropanol are preferable, and dimethylsulfoxide (DMSO), N,N-dimethylformamide and N-methylpyrrolidone can be also preferably used.

In washing after redissolution and reprecipitation, for example, water or solvents such as isopropanol, heptane and methanol can be preferably used.

In liquid-liquid washing, a poor solvent (which does not dissolve the first ammonium salt compound (e.g., the aforementioned hydrocarbon solvent, ether solvent)), and a good solvent (which dissolves the first ammonium salt compound (e.g., organic solvent such as dimethylsulfoxide and dimethylformamide, a mixed solvent of water and polar solvent)) are used in combination.

After the salt exchange reaction in the step of obtaining a first ammonium salt compound, it is preferable that the first ammonium compound contained in the reaction mixture be separated and purified.

The separation and purification can be conducted by a conventional method. For example, any one of concentration, water rinse, organic solvent rinse, solvent extraction, distillation, crystallization, recrystallization and chromatography can be used alone, or two or more of these methods may be used in combination.

<<Production Method of Compound>>

The method of producing a compound of the second aspect of the present invention includes: a step of reacting a first ammonium salt compound containing a first ammonium cation which is a primary, secondary or tertiary ammonium cation, with a nitrogen-containing compound having a lone pair to obtain a second ammonium salt compound which contains a conjugated acid of the nitrogen-containing compound, wherein the conjugated acid of the nitrogen-containing compound has a larger pKa than the pKa of the first ammonium cation (hereafter, this step is referred to as "step of obtaining second ammonium salt compound"); and a step of conducting salt exchange between the second ammonium salt compound and a sulfonium cation or iodonium cation which has a higher hydrophobicity than the hydrophobicity of the conjugated acid of the nitrogen-containing compound (hereafter, this step is referred to as "salt exchange step").

The compound produced by the production method is useful as an acid generator component of a resist composition.

In the production method of the present invention, taking into consideration the hydrophobicity of a sulfonium cation or iodonium cation contained in a compound as a final objective product, a first ammonium salt compound, a nitrogen-containing compound and a compound for salt exchange are selected and used in combination, such that they fulfill the predetermined relation of pKa value and hydrophobicity.

[Step of Obtaining Second Ammonium Salt Compound]

In the step of obtaining a second ammonium salt compound, by reacting a first ammonium salt compound containing a first ammonium cation, which is a primary, secondary or tertiary ammonium cation, with a nitrogen-containing compound having a lone pair, a second ammonium salt compound which contains a conjugated acid of the nitrogen-containing compound can be obtained, wherein the conjugated acid of the nitrogen-containing compound has a larger pKa than the pKa of the first ammonium cation.

This step can be conducted by applying, for example, the aforementioned 《Production method of ammonium salt compound》 according the first aspect of the present invention.

[Salt Exchange Step]

In the salt exchange step, salt exchange between the second ammonium salt compound obtainable in the aforementioned [Step of obtaining second ammonium salt compound] and a sulfonium cation or iodonium cation which has a higher hydrophobicity than the hydrophobicity of the conjugated acid of the nitrogen-containing compound is conducted.

(Sulfonium Cation or Iodonium Cation)

The sulfonium cation or iodonium cation used in salt exchange reaction is a cation having a higher hydrophobicity than that of a cation moiety of the second ammonium salt compound (i.e., second ammonium cation, conjugated acid of the nitrogen-containing compound). In the salt exchange process, by conducting salt exchange reaction so as to replace a cation moiety having a low hydrophobicity with a cation moiety having a high hydrophobicity, salt exchange can satisfactorily proceeds. As a result, a compound containing a desired sulfonium cation or iodonium cation (i.e., final objective product) can be effectively produced with a high yield.

Examples of the sulfonium cation or iodonium cation used in salt exchange step include cations represented by general formulae (ca-1) to (ca-4) shown below.

[Chemical Formula 26]

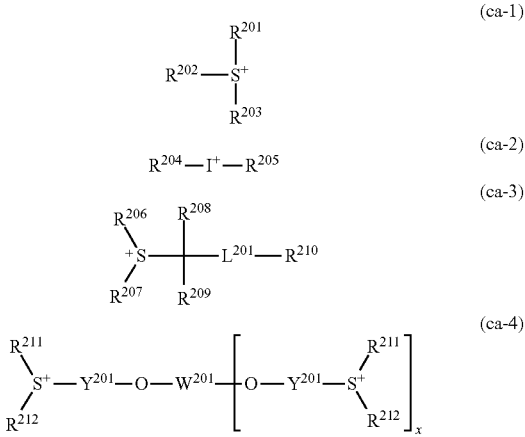

In the formulae, each of $R^{201}$ to $R^{207}$, $R^{211}$ and $R^{212}$ independently represents an aryl group which may have a substituent, an alkyl group which may have a substituent or an alkenyl group which may have a substituent; $R^{201}$ to $R^{203}$, $R^{206}$ and $R^{207}$, and $R^{211}$ and $R^{212}$ may be mutually bonded to form a ring with the sulfur atom; $R^{208}$ and $R^{209}$ each represents a hydrogen atom or an alkyl group of 1 to 5 carbon atoms; $R^{211}$ represents an aryl group which may have a substituent, an alkyl group which may have a substituent, an alkenyl group which may have a substituent or an —$SO_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group of 6 to 20 carbon atoms can be mentioned, and a phenyl group or a naphthyl group is preferable.

As the alkyl group for $R^{201}$ to $R^{207}$, $R^{211}$ and $R^{212}$, a chain-like or cyclic alkyl group of 1 to 30 carbon atoms is preferable.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$, $R^{210}$ to $R^{212x}$ may have include an alkyl group, a halogen atom, a halogenated alkyl group, a carbonyl group, a cyano group, an amino group, an aryl group and groups represented by formulae (ca-r-1) to (ca-r-7) shown below.

[Chemical Formula 27]

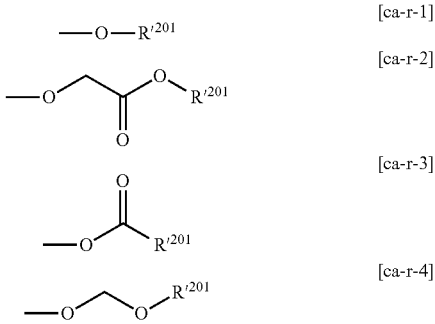

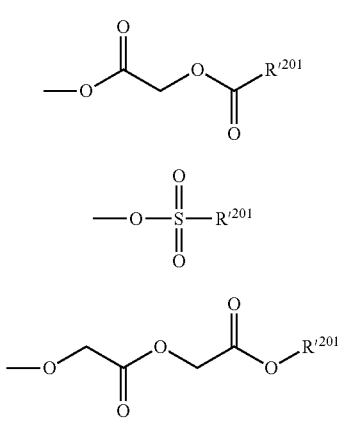

[ca-r-5]

[ca-r-6]

[ca-r-7]

In the formulae, $R'^{201}$ each independently represents a hydrogen atom, a cyclic group which may have a substituent, a chain-like alkyl group which may have a substituent or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R^{101}$ in the aforementioned formula (an1-1) can be mentioned. As the cyclic group which may have a substituent and chain-like alkyl group which may have a substituent, the same groups as those described above for the acid dissociable group represented by formula (a1-r-2) described later can be also mentioned.

When $R^{201}$ to $R^{203}$, $R^{206}$ and $R^{207}$, and $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). As the ring to be formed, the ring containing the sulfur atom in the skeleton thereof is preferably a 3 to 10-membered ring, and most preferably a 5 to 7-membered ring. Examples of the formed ring include a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxathiin ring, a tetrahydrothiophenium ring and a tetrahydrothiopyranium ring.

$R^{208}$ and $R^{209}$ each independently represents a hydrogen atom or an alkyl group of 1 to 5 carbon atoms, is preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent or an —SO$_2$-containing cyclic group which may have a substituent.

As the aryl group for $R^{210}$, an unsubstituted aryl group of 6 to 20 carbon atoms can be mentioned, and a phenyl group or a naphthyl group is preferable.

As the alkyl group for $R^{210}$, a chain-like or cyclic alkyl group of 1 to 30 carbon atoms is preferable.

The alkenyl group for $R^{210}$ preferably has 2 to 10 carbon atoms.

As the —SO$_2$— containing cyclic group for $R^{210}$ which may have a substituent, the same groups as the "—SO$_2$— containing cyclic group" for Ra$^{21}$ in general formula (a2-1) described later can be mentioned, and the group represented by general formula (a5-r-1) described later is preferable.

$Y^{201}$ each independently represents an arylene group, an alkylene group or an alkenylene group.

As the arylene group for $Y^{201}$, a group in which one hydrogen atom has been removed from an aryl group exemplified as an aromatic hydrocarbon group for $R^{101}$ in the aforementioned formula (an1-1) can be mentioned.

As the alkylene group and the alkenylene group for $Y^{201}$, the same aliphatic hydrocarbon group as the divalent hydrocarbon group for Va$^1$ in general formula (a1-1) described later can be mentioned.

In the formula (ca-4), x represents 1 or 2.

$W^{201}$ represents a linking group having a valency of (x+1), that is, a divalent or trivalent linking group.

As the divalent linking group for $W^{201}$, a divalent hydrocarbon groups which may have a substituent is preferable, and as examples thereof, the same groups as the hydrocarbon group for Ya$^{21}$ in general formula (a2-1) described later can be mentioned. The divalent linking group for $W^{201}$ may be linear, branched or cyclic, and cyclic is more preferable. Among these, an arylene group having two carbonyl groups, each bonded to the terminal thereof is preferable. As the arylene group, a phenylene group and a naphthylene group can be mentioned. Of these, a phenylene group is particularly desirable.

As the trivalent linking group for $W^{201}$, a group in which one hydrogen atom has been removed from the aforementioned divalent linking group for $W^{201}$, and a group in which the divalent linking group has been bonded to an another divalent linking group can be mentioned. The trivalent linking group for $W^{201}$ is preferably an arylene group having two carbonyl groups bonded thereto.

Specific examples of preferable cations represented by formula (ca-1) include cations represented by formulae (ca-1-1) to (ca-1-63) shown below.

[Chemical Formula 28]

(ca-1-1)

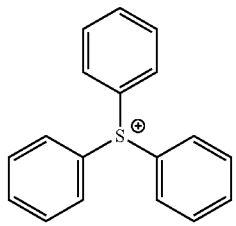

(ca-1-2)

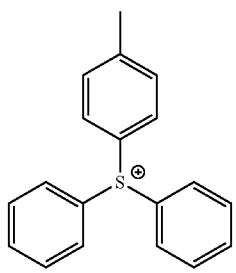

(ca-1-3)
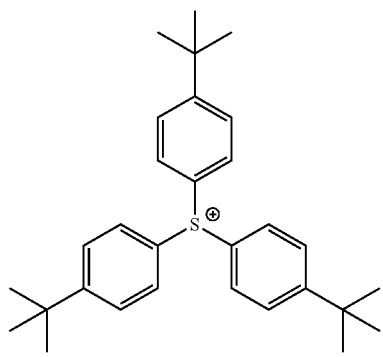
(ca-1-4)
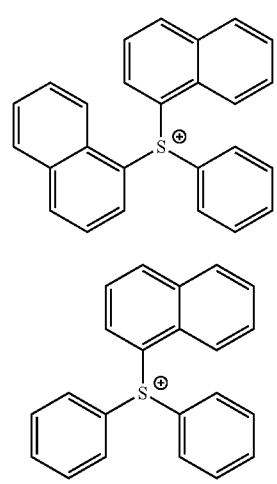
(ca-1-5)
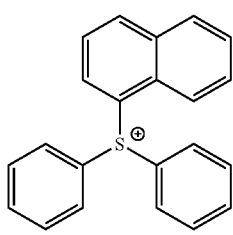
(ca-1-6)
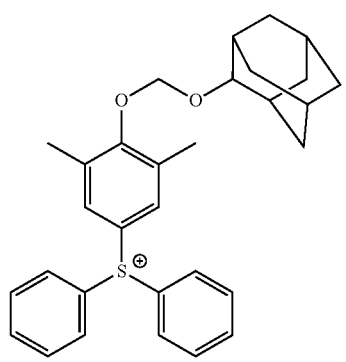
(ca-1-7)
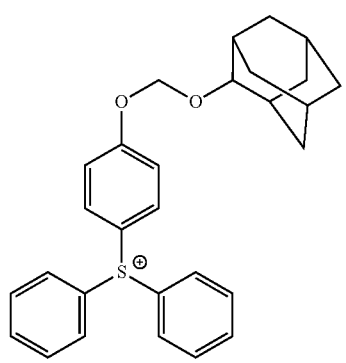
(ca-1-8)
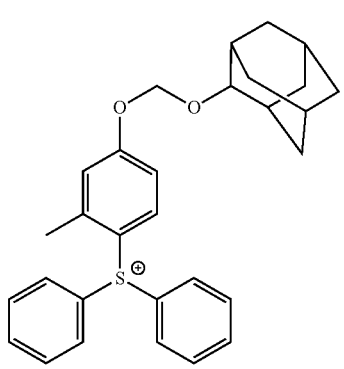
(ca-1-9)
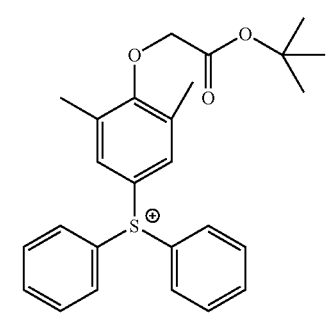
(ca-1-10)
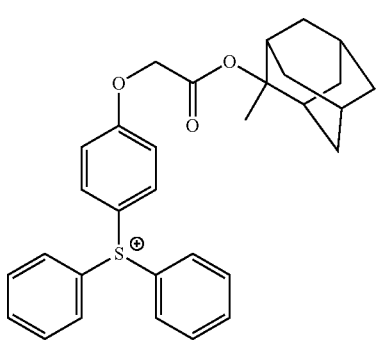
(ca-1-11)
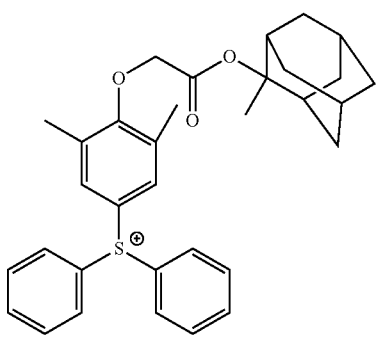

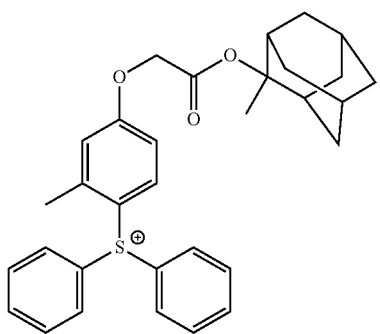 (ca-1-12)
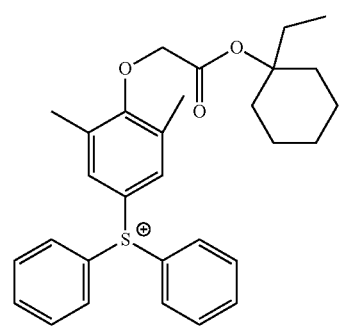 (ca-1-13)
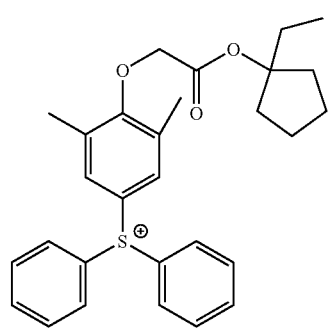 (ca-1-14)
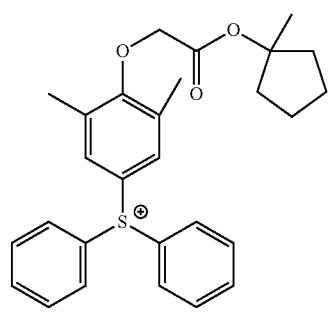 (ca-1-15)
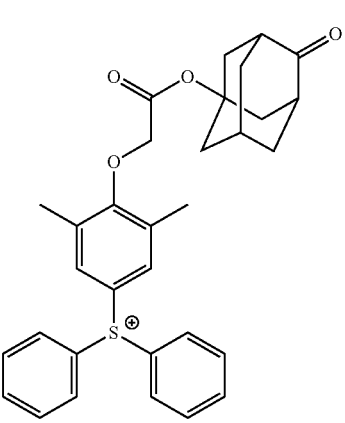 (ca-1-16)
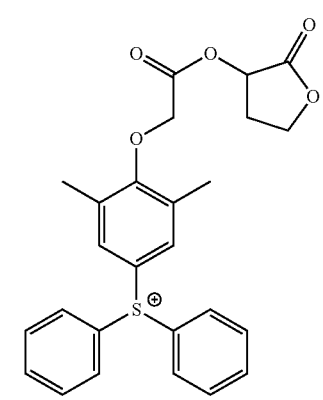 (ca-1-17)
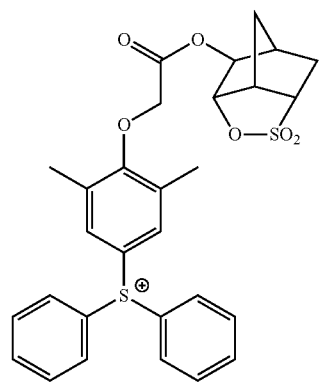 (ca-1-18)
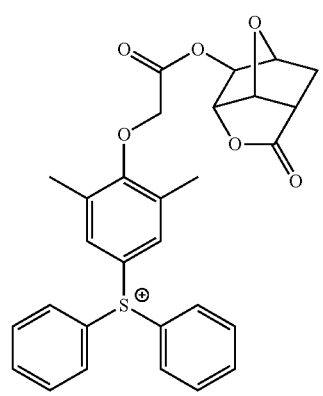 (ca-1-19)

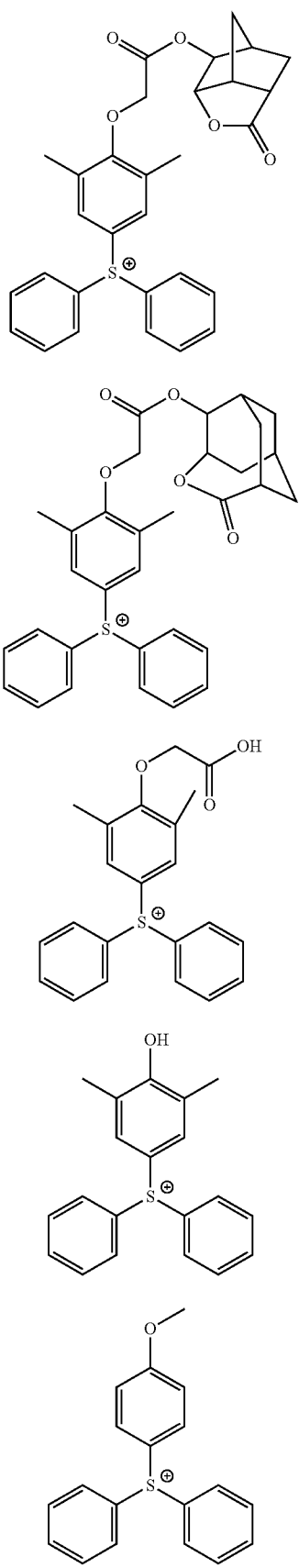
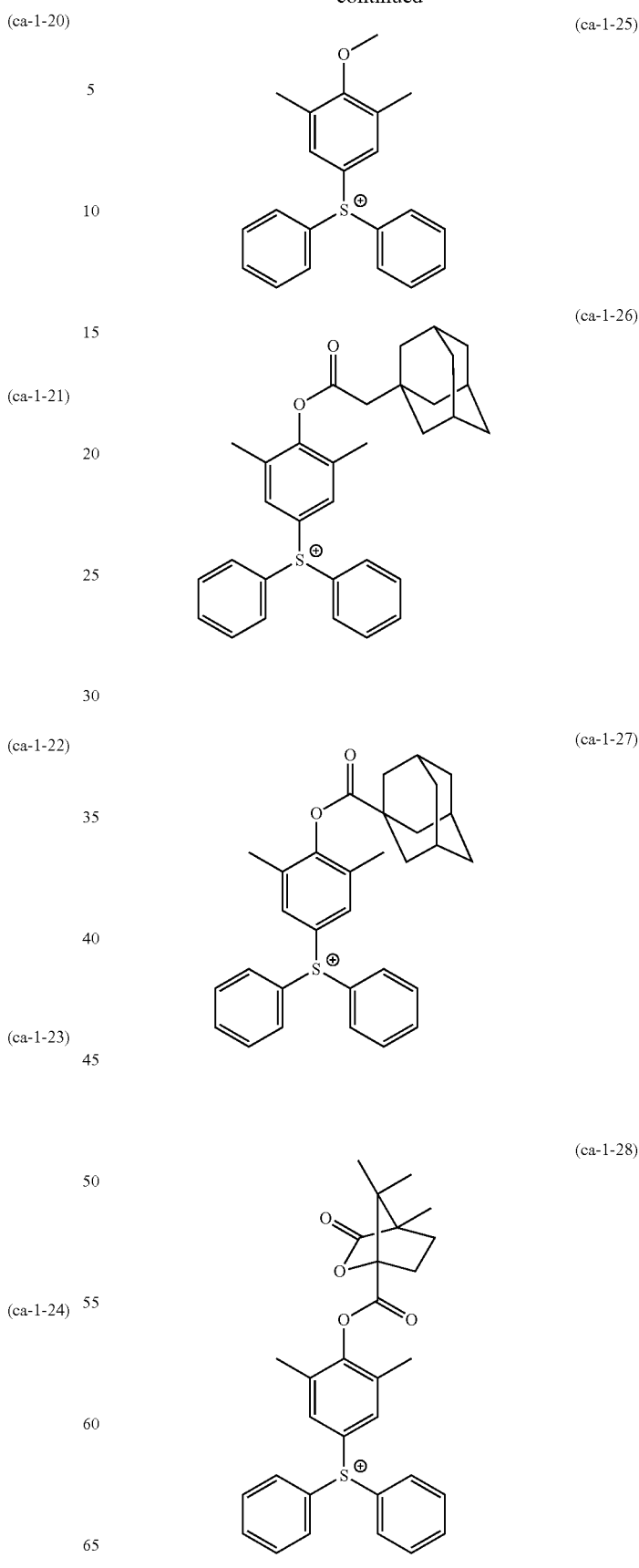

[Chemical Formula 29]
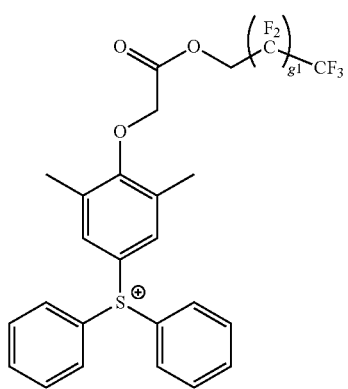
(ca-1-29)
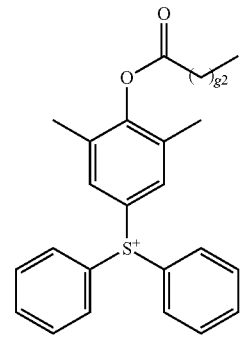
(ca-1-30)
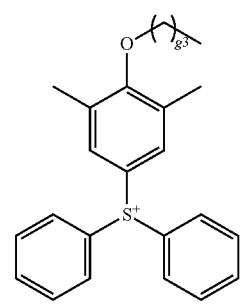
(ca-1-31)
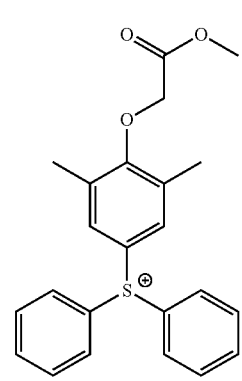
(ca-1-32)
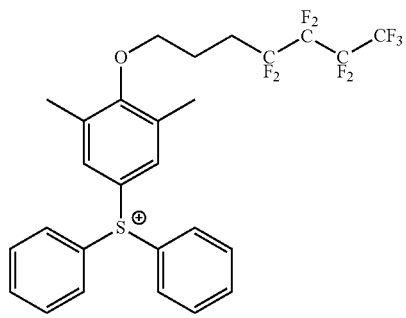
(ca-1-33)
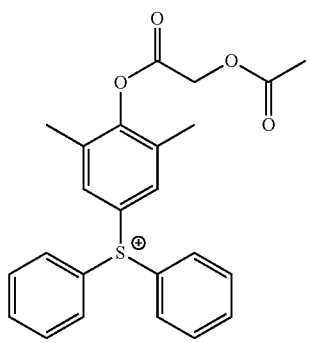
(ca-1-34)
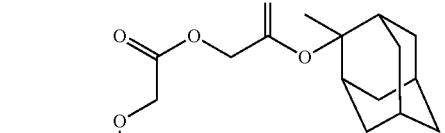
(ca-1-35)
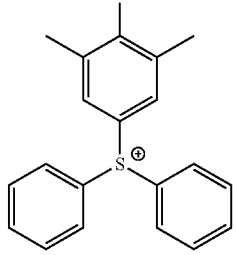
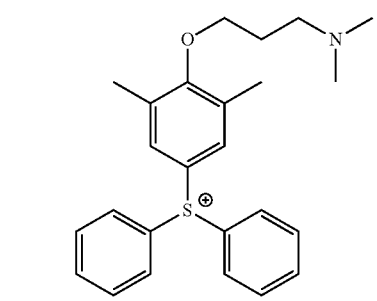
(ca-1-36)
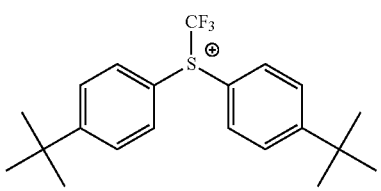
(ca-1-37)

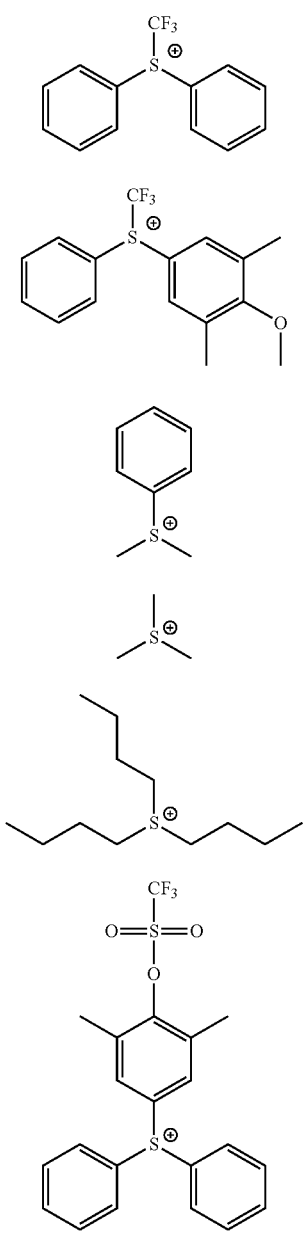
In the formulae, g1, g2 and g3 represent recurring numbers, wherein g1 is an integer of 1 to 5, g2 is an integer of 0 to 20, and g3 is an integer of 0 to 20.
[Chemical Formula 30]
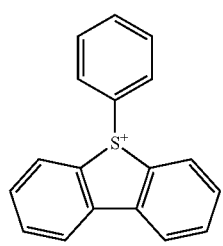
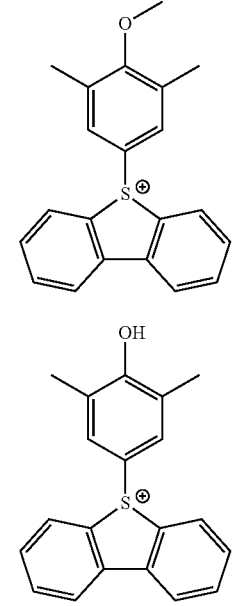
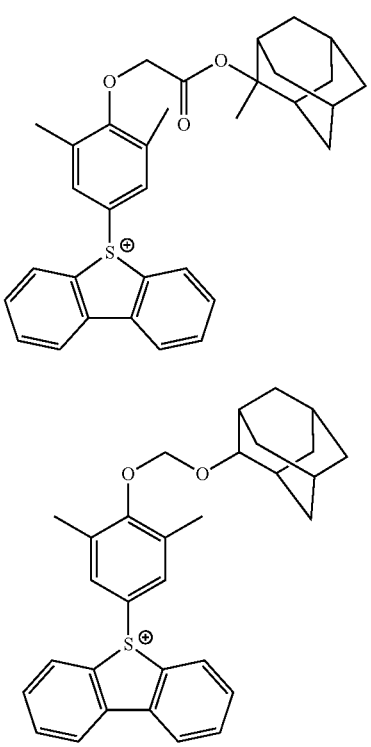
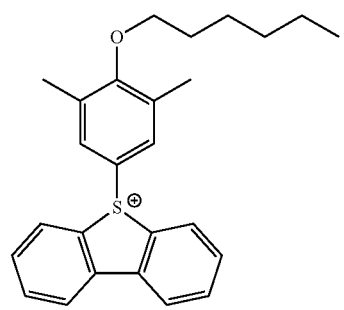

(ca-1-50) 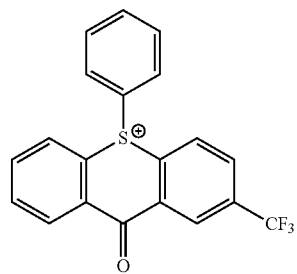
(ca-1-51) 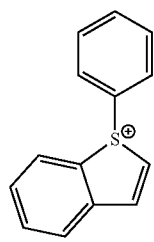
(ca-1-52) 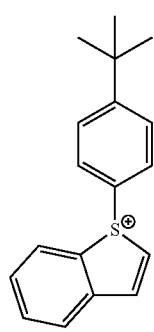
(ca-1-53) 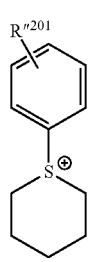
(ca-1-54) 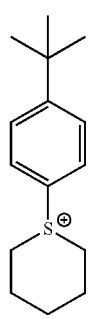
(ca-1-55) 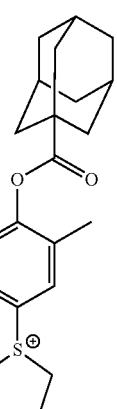
(ca-1-56) 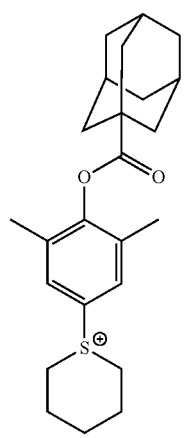
(ca-1-57) 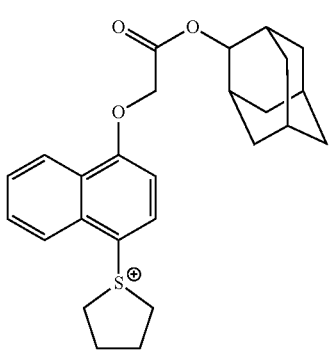
(ca-1-58) 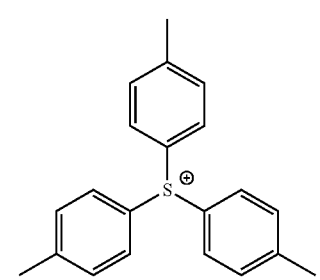

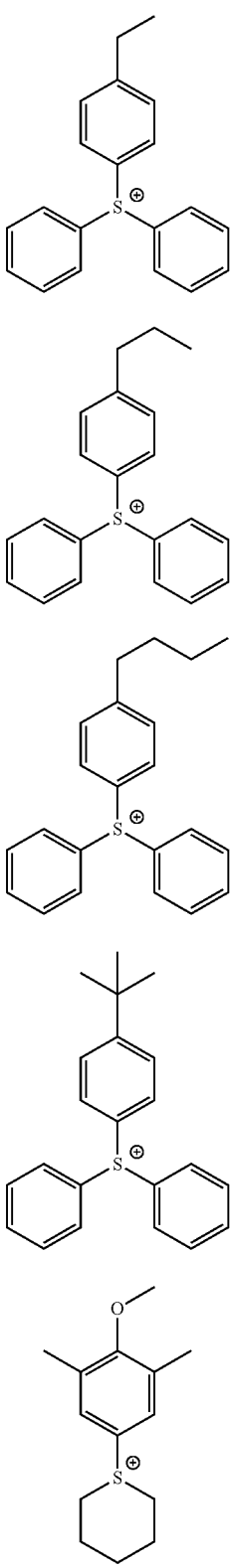

(ca-1-59)

(ca-1-60)

(ca-1-61)

(ca-1-62)

(ca-1-63)

Specific examples of preferable cations represented by the formula (ca-2) include diphenyliodonium and bis(4-tert-butylphenyl)iodonium.

Specific examples of preferable cations represented by the formula (ca-3) include cations represented by formulae (ca-3-1) to (ca-3-6) shown below.

[Chemical Formula 31]

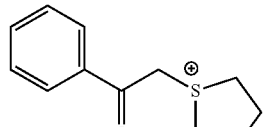

(ca-3-1)

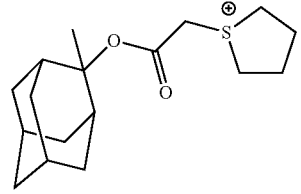

(ca-3-2)

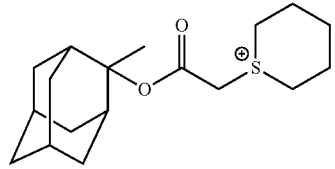

(ca-3-3)

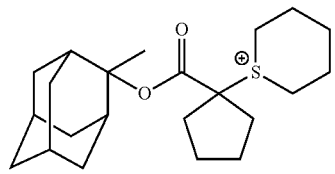

(ca-3-4)

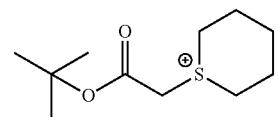

(ca-3-5)

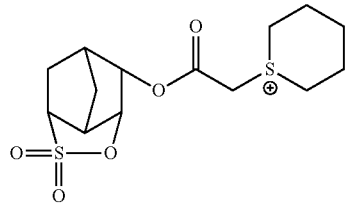

(ca-3-6)

In the formulae, $R''^{201}$ represents a hydrogen atom or a substituent, and as the substituent, the same groups as those described above for substituting the $R^{201}$ to $R^{207}$ and $R^{210}$ to $R^{212}$ can be mentioned.

Specific examples of preferable cations represented by formula (ca-4) include cations represented by formulae (ca-4-1) and (ca-4-2) shown below.

[Chemical Formula 32]

(ca-4-1)

(ca-4-2)

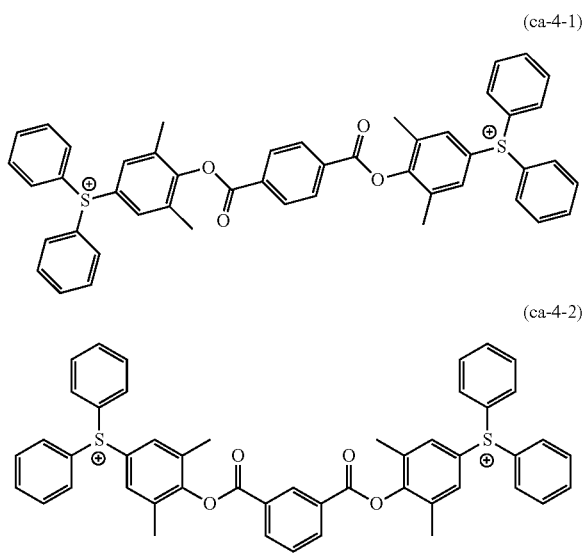

It is preferable that the retention time of the sulfonium cation or iodonium cation used in salt exchange step is 1.5 minutes or more, and more preferably 2 minutes or more, wherein the retention time is measured under the specific condition in accordance with the aforementioned HPLC method. The upper limit is not particularly limited, and is preferably 60 minutes or less. When the retention time is at least as large as the lower limit of the above-mentioned range, salt exchange between the second ammonium salt compound and a sulfonium cation or iodonium cation easily proceeds.

With respect to the sulfonium cation or iodonium cation exemplified above, the retention time measured under the specific condition in accordance with the aforementioned HPLC method is as follows.

Here, a cation which contains a substituent having a high hydrophobicity tends to exhibit a long retention time, whereas a cation which contains a hydrophilic group such as a polar group tends to exhibit a short retention time.

Examples of a cation which exhibits a retention time of 2.6 minutes or less include cations represented by the formulae (ca-1-38) to (ca-1-42) and (ca-1-63); a cation represented by formula (ca-1-53) in which $R''^{201}$ is a small group such as a hydrogen atom, a methyl group or an alkoxy group; a cation represented by formula (ca-1-53) which has a polar group such as a hydroxy group or a carboxy group; and cations represented by the formulae (ca-3-1), (ca-3-5) and (ca-3-6). For example, the retention time of the cation represented by the formula (ca-1-38) is 2.3 minutes, and the retention time of the cation represented by the formula (ca-1-63) is 2.6 minutes.

Examples of a cation which exhibits a retention time within the range of greater than 2.6 minutes to 4 minutes or less include cations represented by the formulae (ca-1-1), (ca-1-2), (ca-1-17) to (ca-1-25), (ca-1-28) and (ca-1-29); cations represented by the formulae (ca-1-30) to (ca-1-31) in which the recurring numbers g2 and g3 is small (about 0 to 2); cations represented by the formulae (ca-1-32), (ca-1-34), (ca-1-36), (ca-1-43) to (ca-1-46), (ca-1-50) to (ca-1-52), (ca-1-54) and (ca-1-58) to (ca-1-60); and other cations represented by the formula (ca-1-53). For example, the retention time of the cation represented by the formula (ca-1-1) is 2.7 minutes, and the retention time of the cation represented by the formula (ca-1-2) is 3.1 minutes.

Examples of a cation which exhibits a retention time of greater than 4 minutes include cations represented by the formulae (ca-1-3) to (ca-1-16), (ca-1-21), (ca-1-26), (ca-1-27) and (ca-1-29); cations represented by the formulae (ca-1-30) to (ca-1-31) in which the recurring numbers g2 and g3 are large (3 or more); cations represented by formulae (ca-1-33), (ca-1-35), (ca-1-37), (ca-1-47) to (ca-1-49), (ca-1-55) to (ca-1-57), (ca-1-61), (ca-1-62) and (ca-3-2) to (ca-3-4); cations represented by the formulae (ca-4-1) and (ca-4-2). For example, the retention time of the cation represented by the formula (ca-1-29) in which g1 is 1 is 6.7 minutes.

Further, it is necessary that there is a certain difference in retention time between the second ammonium cation (conjugated acid of the nitrogen-containing compound) and the sulfonium cation or iodonium cation, wherein the retention time can be measured in accordance with the aforementioned HPLC method. The value obtained by dividing the retention time of the sulfonium cation or iodonium cation by the retention time of the second ammonium cation is greater than 1, more preferably 1.005 or more, and still more preferably 1.01 or more. When the value is 1.005 or more, salt exchange easily proceeds. The second ammonium cation has a high hydrophilicity and the retention time thereof is basically short. Therefore, when there is a slightly difference in retention time between the second ammonium cation and the sulfonium cation or iodonium cation, salt exchange easily proceeds.

(Salt Exchange Between Second Ammonium Salt Compound and Sulfonium Cation or Iodonium Cation)

The salt exchange reaction between the second ammonium salt compound and a sulfonium cation or iodonium cation is preferably conducted in a two-phase reaction system of water and an organic solvent.

In the salt exchange step, for example, by mixing the second ammonium salt compound and a compound containing a sulfonium cation or iodonium cation (compound for salt exchange) in a mixed solvent of an organic solvent and water, a desired compound can be obtained.

The compound for salt exchange used in the salt exchange step is a compound containing a sulfonium cation or iodonium cation, and is capable of conducting salt exchange between the sulfonium cation or iodonium cation contained in the compound for salt exchange and the second ammonium cation. That is, the sulfonium cation or iodonium cation of the compound for salt exchange becomes the cation moiety of the compound produced by the production method of the present invention.

It is preferable that the compound for salt exchange is a compound composed of a cation moiety (which is a sulfonium cation or iodonium cation) and an anion moiety (which is a non-nucleophilic ion).

Examples of non-nucleophilic ions include a halogen ion such as a bromine ion or a chlorine ion; an ion capable of forming an acid exhibiting a lower acidity than the second ammonium salt compound; $BF_4^-$, $AsF_6^-$, $SbF_6^-$, $PF_6^-$ and $ClO_4^-$. The ion capable of forming an acid exhibiting a lower acidity than the second ammonium salt compound is not particularly limited, and can be appropriately determined depending on the second ammonium salt compound. Examples thereof include sulfonate ions such as a p-toluenesulfonate ion, a methanesulfonate ion and a benzenesulfonate ion.

As an organic solvent which constitutes a mixed solvent with water, an organic solvent capable of liquid separation from water, and dissolving the second ammonium salt compound can be used. Examples thereof include cyclohexanone, methyl ethyl ketone, propylene glycol monomethyl ether acetate, tetrahydrofuran, dichloromethane, 1,2-dichloroethane, ethyl acetate, propionitrile and a mixed solvent thereof.

The temperature condition during salt exchange is preferably 0 to 50° C., and more preferably 10 to 30° C.

The mixing time for mixing the second ammonium salt compound and compound for salt exchange varies, depending on the reactivity of the second ammonium salt compound and compound for salt exchange, the temperature condition and the like. However, in general, the mixing time is preferably 0.5 minutes to 24 hours, more preferably 5 minutes to 12 hours, and still more preferably 10 to 60 minutes.

The amount of the compound for salt exchange used in the salt exchange reaction is preferably 1 to 10 moles per 1 mole of the second ammonium salt compound, and more preferably 1 to 5 moles per 1 mole of the second ammonium salt compound.

After the salt exchange reaction between the second ammonium salt compound and compound for salt exchange, it is preferable that the compound (final objective product) contained in the reaction mixture be separated and purified.

The separation and purification can be conducted by a conventional method. For example, any one of concentration, water rinse, organic solvent rinse, solvent extraction, distillation, crystallization, recrystallization and chromatography can be used alone, or two or more of these methods may be used in combination.

According to the method of producing a compound of the present invention, the second ammonium salt compound as an intermediate can be obtained with high purity, and salt exchange satisfactorily proceeds. As a result, a compound having hardly any impurities can be obtained with a high yield.

《Compound》

The compound of the third aspect of the present invention is a compound produced in accordance with <<Production method of compound>> according to the second aspect of the present invention. The compound is preferable as an acid generator component for a resist composition. Further, the compound is preferable as a quencher (acid diffusion control agent) of a resist composition.

The compound according to the present invention may have a polymerizable group (hereafter, the compound having a polymerizable group is referred to as "compound (m)").

Examples of the polymerizable group include a vinyl group, an allyl group, an acryloyl group, a methacryloyl group, a fluorovinyl group, a difluorovinyl group, a trifluorovinyl group, a difluorotrifluoromethylvinyl group, a trifluoroallyl group, a perfluoroallyl group, a trifluoromethylacryloyl group, a nonylfluorobutylacryloyl group, a vinyl ether group, a fluorine-containing vinyl ether group, an allyl ether group, an fluorine-containing allyl ether group, a styryl group, a fluorine-containing styryl group, a norbornyl group, a fluorine-containing norbornyl group, and a silyl group.

Examples of the compound (m) include a compound in which the aforementioned organic anion (preferably the aforementioned sulfonate anion, amide anion, methide anion and carboxylate anion) has been bonded to a polymerizable group via a linking group or has been bonded directly to a polymerizable group without a linking group.

As the linking group, the groups represented by formulae (y-a1-11) to (y-a1-15), and (y-ar-1) to (y-ar-4) shown below can be mentioned.

[Chemical Formula 33]

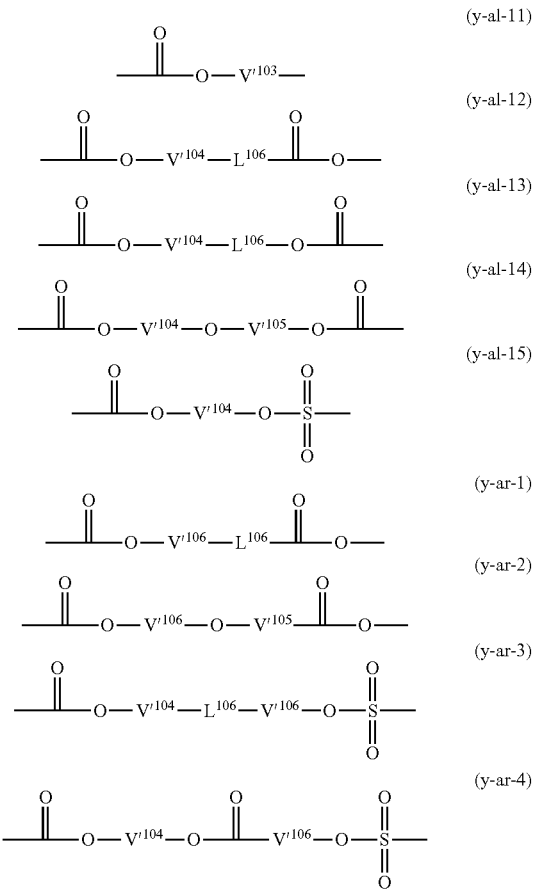

In the formulae, $V'^{103}$ represents a single bond or a divalent hydrocarbon group of 1 to 30 carbon atoms; $V'^{104}$ represents a divalent hydrocarbon group of 1 to 30 carbon atoms which may have a substituent; $L^{106}$ represents —NH—, —S— or a single bond; $V'^{105}$ represents an alkylene group of 1 to 10 carbon atoms; and $V'^{106}$ represents a divalent aromatic hydrocarbon group which may have a substituent.

In the formulae, $V'^{103}$ represents a single bond or a divalent hydrocarbon group of 1 to 30 carbon atoms.

The divalent hydrocarbon group for $V'^{103}$ is preferably a saturated hydrocarbon group, and more preferably an alkylene group of 1 to 30 carbon atoms. The alkylene group for $V'^{103}$ may be any of linear, branched or cyclic.

Specific examples of the alkylene group for $V'^{103}$ include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

Further, a divalent aliphatic cyclic group of 5 to 10 carbon atoms, for example, a group in which two hydrogen atoms have been removed from the aliphatic hydrocarbon ring such as cyclohexane, norbornane or adamantane, can be also preferably used.

Specific examples of such groups include a cyclohexylene group, a 1,5-adamantylene group and a 2,6-adamantylene group.

In the formulae, $V'^{104}$ represents a divalent hydrocarbon group of 1 to 30 carbon atoms which may have a substituent. The divalent hydrocarbon group represented by $V'^{104}$ is the same as defined above for the divalent hydrocarbon group represented by $V'^{103}$.

Examples of substituents which $V'^{104}$ may have include a halogen atom (preferably fluorine atom), a hydroxy group and an oxo group (=O).

In the formulae, $L^{106}$ represents —NH—, —S— or a single bond.

In the formulae, $V'^{105}$ represents an alkylene group of 1 to 10 carbon atoms, and preferably an alkylene group of 1 to 5 carbon atoms.

In the formulae, $V^{106}$ represents a divalent aromatic hydrocarbon group which may have a substituent.

As the divalent aromatic hydrocarbon group for $V'^{106}$, a group in which two hydrogen atoms have been removed from the aforementioned aromatic ring exemplified in the explanation of $R^{106}$ to $R^{108}$ (arylene group), and a group in which one hydrogen atom has been removed from the aromatic ring and another one of hydrogen atom has been substituted with an alkylene group can be mentioned. Examples of the substituents which $V'^{106}$ may have include the same substituents as described above for substituents for substituting the cyclic hydrocarbon group for $R^{101}$ (e.g., an alkyl group, an alkoxy group, a halogen atom, a halogenated alkyl group, a hydroxyl group, a carbonyl group, a nitro group or the like).

As a preferable example of the compound (m), a compound represented by general formula (a6-1) shown below can be given.

[Chemical Formula 34]

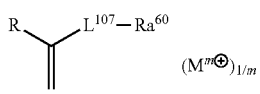

(a6-1)

In the formula, R represents a hydrogen atom, an alkyl group of 1 to 5 carbon atoms or a halogenated alkyl group of 1 to 5 carbon atoms; $L^{107}$ represents a single bond or a divalent linking group; $Ra^{60}$ represents an organic anion; m represents an integer of 1 or more; and $M^{m+}$ represents a sulfonium cation or an iodonium cation.

In general formula (a6-1), R represents a hydrogen atom, an alkyl group of 1 to 5 carbon atoms or a halogenated alkyl group of 1 to 5 carbon atoms.

The alkyl group and the halogenated alkyl group for R are respectively the same as defined for the alkyl group and the halogenated alkyl group for the substituent which may be bonded to the carbon atom on the α-position of the aforementioned substituted acrylate ester. R is preferably a hydrogen atom, an alkyl group of 1 to 5 carbon atoms or a fluorinated alkyl group of 1 to 5 carbon atoms, and most preferably a hydrogen atom or a methyl group.

In the formula (a6-1), $L^{107}$ represents a single bond or a divalent linking group. As the divalent linking group for $L^{107}$, the linking groups represented by the aforementioned formulae (y-a1-11) to (y-a1-15), and (y-ar-1) to (y-ar-4) shown below can be mentioned.

In the formula (a6-1), $Ra^{60}$ represents an organic anion. Examples of the organic anion include a sulfonate anion, an amide anion, a methide anion and a carboxylate anion, and anions represented by formulae (an-m1) to (an-m4) shown below are preferably used.

[Chemical Formula 35]

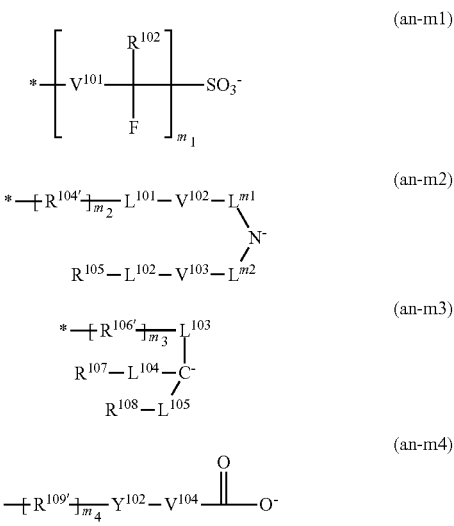

In the formula (an-m1), $R^{102}$, $V^{101}$ and $m_1$ are the same as defined for $R^{102}$, $V^{101}$ and $m_1$ in the formula (an1-1).

In the formula (an-m2), $R^{104'}$ is a group in which one hydrogen atom has been removed from a cyclic group, chain-like alkyl group or chain-like alkenyl group for $R^{104}$ in the formula (an1-2). $R^{105}$ is the same group as defined above for $R^{105}$ in the formula (an1-2), and $R^{104'}$ and $R^{105}$ may be mutually bonded to form a ring. $V^{102}$, $V^{103}$, $L^{101}$, $L^{102}$, $L^{m1}$ and $L^{m2}$ are the same as defined for $V^{102}$, $V^{103}$, $L^{101}$, $L^{102}$, $L^{m1}$ and $L^{m2}$ in the formula (an1-2). $m_2$ represents 0 or 1.

In the formula (an-m3), $R^{106'}$ is a group in which one hydrogen atom has been removed from a cyclic group, chain-like alkyl group or chain-like alkenyl group for $R^{106}$ in the formula (an1-3). $R^{107}$ and $R^{108}$ are the same groups as defined above for $R^{107}$ and $R^{108}$ in the formula (an1-3), and two of $R^{106'}$, $R^{107}$ and $R^{108}$ may be mutually bonded to form a ring. $L^{103}$ to $L^{105}$ are the same as defied above for $L^{103}$ to $L^{105}$ in the formula (an1-3). $m_3$ represents 0 or 1.

In the formula (an-m4), $R^{109'}$ is a group in which one hydrogen atom has been removed from a cyclic group, chain-like alkyl group or chain-like alkenyl group for $R^{109}$ in the formula (an1-4). $Y^{102}$ and $V^{104}$ are the same as defied above for $Y^{102}$ and $V^{104}$ in the formula (an1-4). $m_4$ represents 0 or 1.

In the formula (a6-1), m represents an integer of 1 or more, and $M^{m+}$ represents a sulfonium cation or an iodonium cation. Examples of the $M^{m+}$ group include cations represented by the general formulae (ca-1) to (ca-4), and specific examples thereof Specific examples of the compounds represented by the formula (a6-1) are shown below, but are not limited to these compounds. In the formulae, $R^α$ represents a hydrogen atom, a methyl group or a trifluoromethyl group, and $(M^{m+})_{1/m}$ is the same as $(M^{m+})_{1/m}$ in the formula (a6-1).

[Chemical Formula 36]
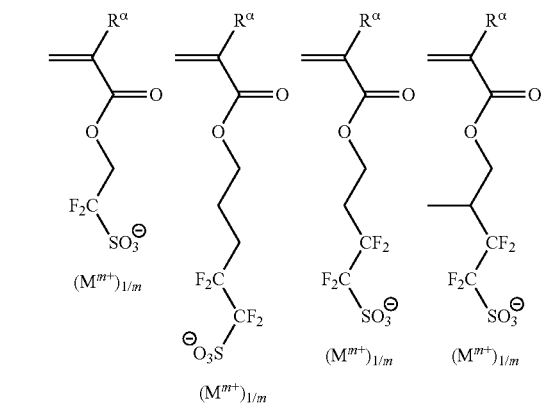
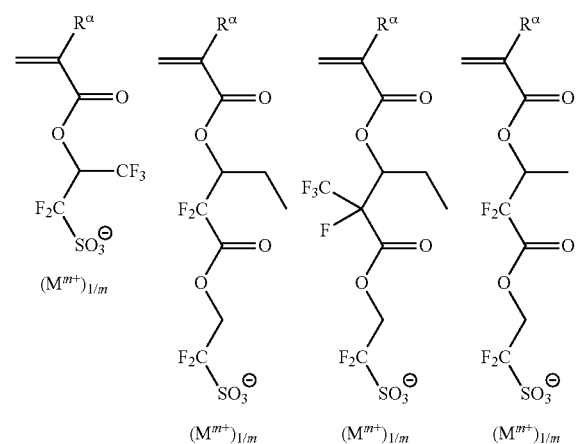
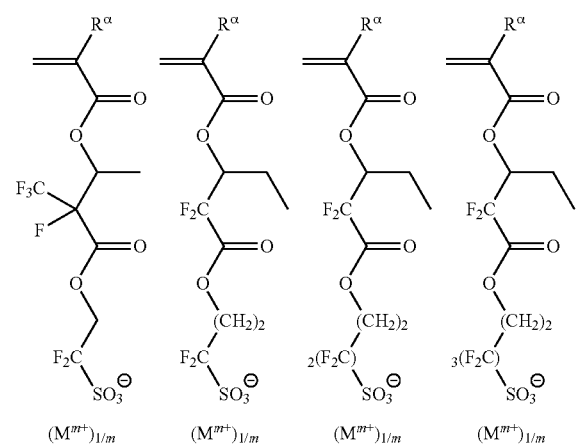
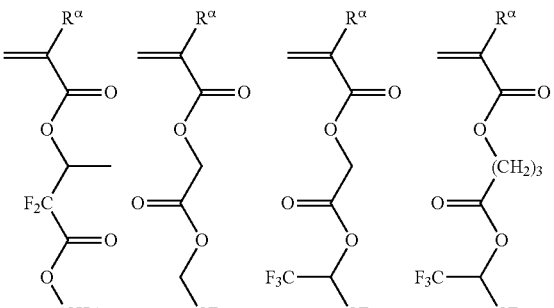
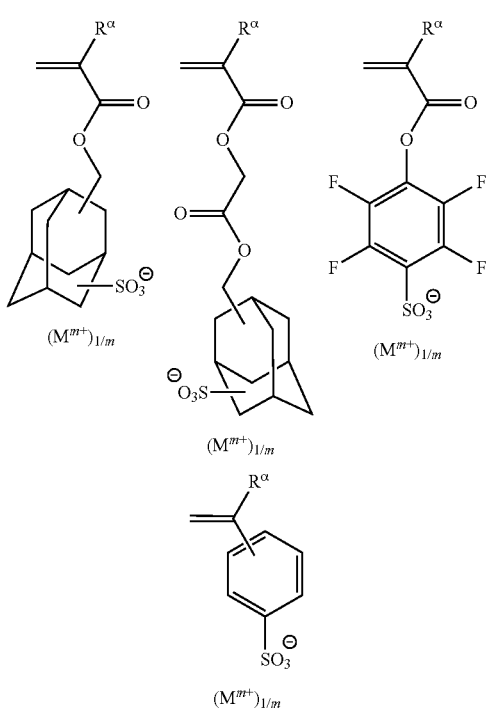
[Chemical Formula 37]
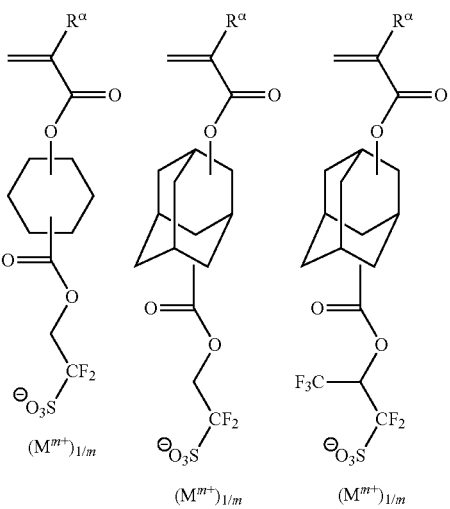

-continued
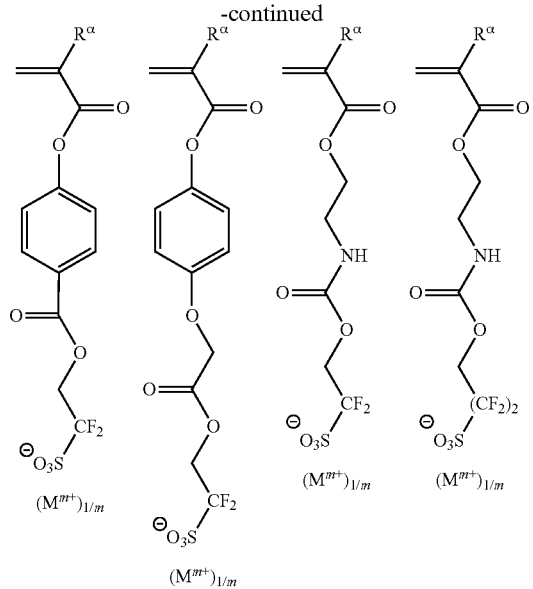
[Chemical Formula 38]
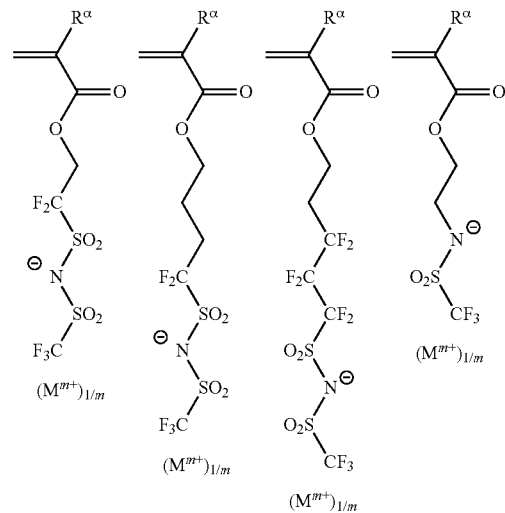
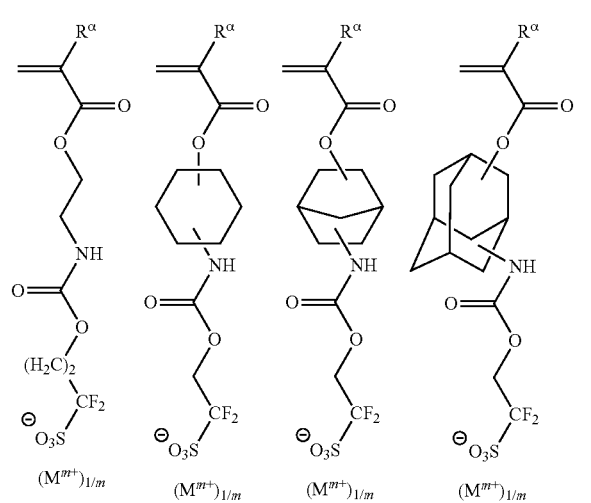
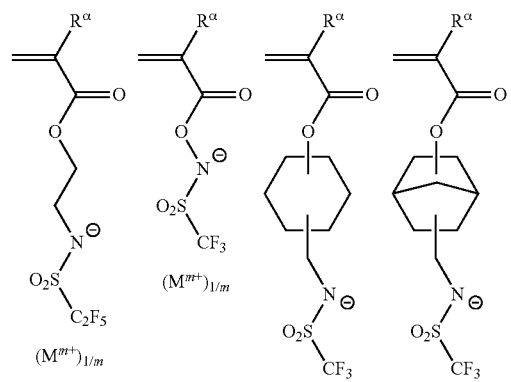
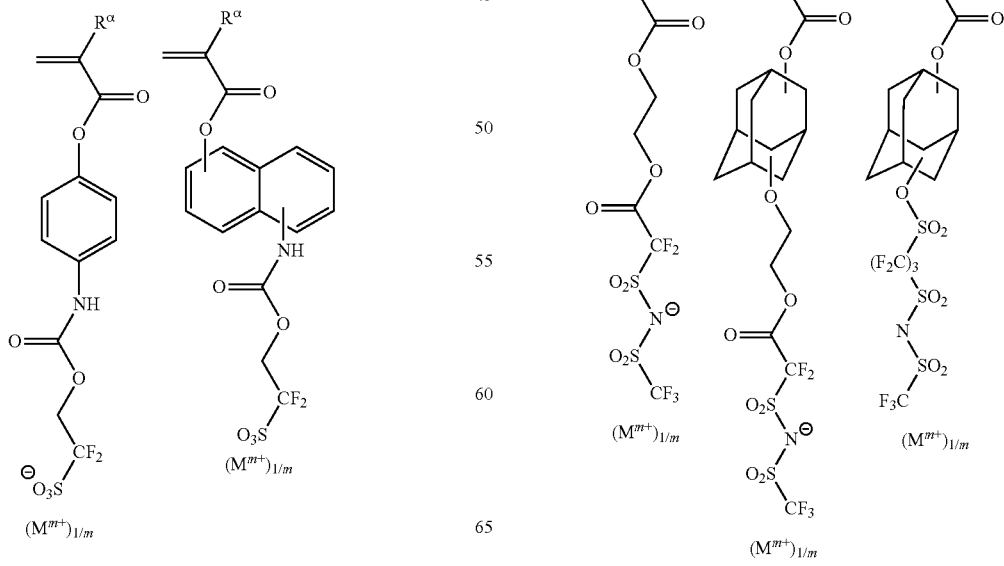

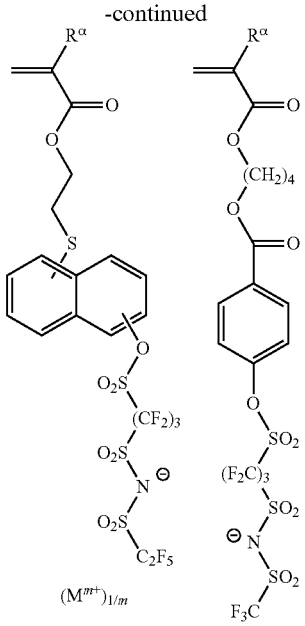
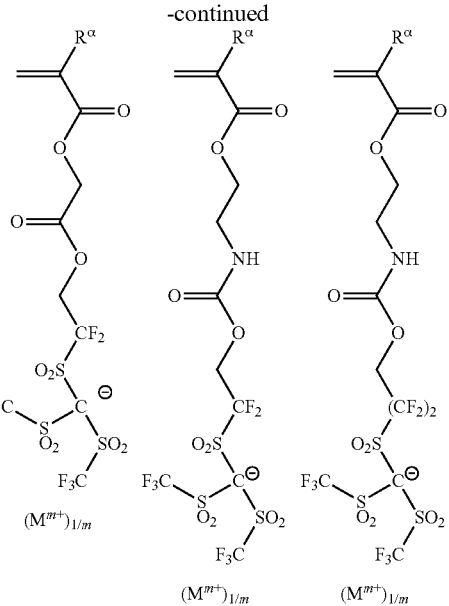
[Chemical Formula 39]
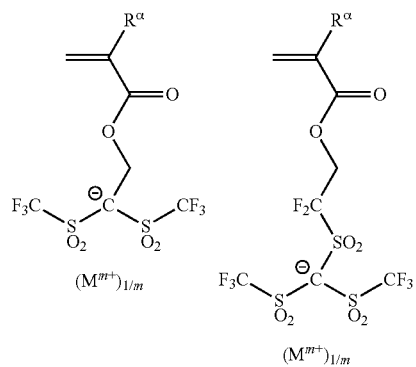
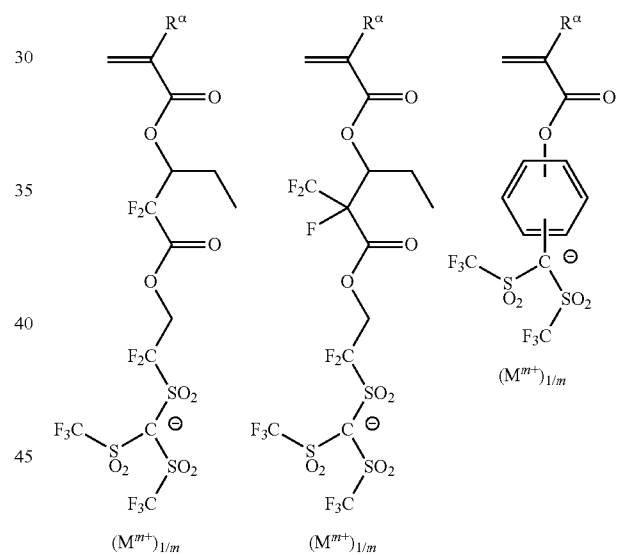
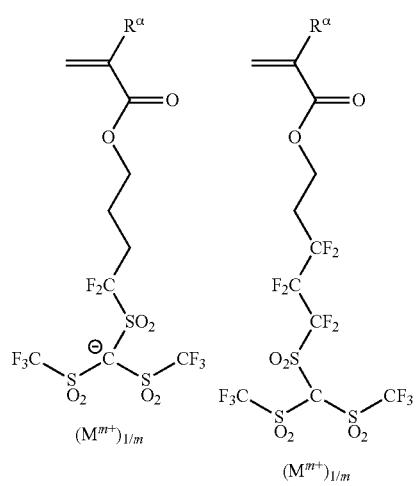

-continued

[Chemical structures with labels $(M^{m+})_{1/m}$]

<<Polymeric Compound>>

The polymeric compound of the fourth aspect of the present invention has a structural unit (hereafter, sometimes referred to as "structural unit (a6)") derived from a compound (compound (m)) of the third aspect of the present invention, which has a polymerizable group.

Such a polymeric compound has a function of generating acid upon exposure, and can be used as a base resin for a resist composition.

Preferable examples of the compound (m) include compounds represented by the general formula (a6-1).

As the structural unit (a6) contained in the polymeric compound, 1 type of structural unit may be used, or 2 or more types may be used.

If desired, the polymeric compound of the fourth aspect of the present invention may further include a structural unit other than the structural unit (a6), as well as the structural unit (a6). Examples of other structural units include a structural unit (a1), a structural unit (a2), a structural unit (a3) and a structural unit (a4), which are described below.

The type of structural unit (a6), the type of other structural units to be introduced if desired, the amount of each structural unit of the polymer compound, the weight average molecular weight of the polymer compound and the dispersity of the polymer compound can be appropriately determined, taking into consideration the desired copolymer compositional ratio and required properties.

The polymeric compound can be obtained by a conventional radical polymerization or the like of the monomers (e.g., compound (m)) corresponding with each of the structural units.

<<Acid Generator>>

The acid generator according to the fifth aspect of the present invention is an acid generator including the aforementioned compound of the third aspect. The explanation of the acid generator is the same as the explanation of the compound of the third aspect of the present invention described above.

The acid generator according to a fourth aspect of the present invention is useful for a resist composition. Further, the acid generator of the fifth aspect of the present invention is also useful as an acid diffusion control agent (component (D)) describe later.

<<Resist Composition>>

The resist composition of a sixth aspect of the present invention includes a polymeric compound of the fourth aspect of the present invention or an acid generator of the fifth aspect of the present invention.

According to the resist composition of the present invention, by using the compound produced in accordance with the aforementioned method of producing a compound of the present invention, excellent lithography properties can be achieved.

As such a resist composition, for example, a resist composition which generates acid upon exposure and exhibits changed solubility in a developing solution under action of acid, and which includes a base component (A) which exhibits changed solubility in a developing solution under action of acid (hereafter, referred to as "component (A)") can be mentioned.

When a resist film is formed using the resist composition and the formed resist film is subjected to a selective exposure, acid is generated at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

The resist composition of the present invention may be either a positive resist composition or a negative resist composition.

Further, in the formation of a resist pattern, the resist composition of the present invention can be applied to an alkali developing process using an alkali developing solution in the developing treatment, or a solvent developing process using a developing solution containing an organic solvent (organic developing solution) in the developing treatment.

The resist composition of the present invention has a function of generating acid upon exposure, and in the resist composition, the component (A) may generate acid upon exposure, or an additive component other than the component (A) may generate acid upon exposure.

More specifically, the resist composition of the present invention may be a resist composition (1) containing an acid generator component (B) which generates acid upon exposure (hereafter, referred to as "component (B)");

a resist composition (2) in which the component (A) is a component which generates acid upon exposure; or a resist composition (3) in which the component (A) is a component which generates acid upon exposure, and further containing an acid generator component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits changed solubility in a developing solution under action of acid, as the component (A) (e.g., component (A-1) or component (A-2) described later), the polymeric compound of the fourth aspect of the present invention can be applied.

When the resist composition of the present invention is the aforementioned resist composition (1), as the component (B), the acid generator of the fifth aspect of the present invention can be applied.

<Component (A)>

In the present invention, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" refers to a polymer having a molecular weight of 1,000 or more.

As the molecular weight of the polymer, the weight average molecular weight in terms of the polystyrene equivalent value determined by gel permeation chromatography (GPC) is used.

As the component (A), a resin, a low molecular weight compound, or a combination thereof may be used.

The component (A) may be a component that exhibits increased solubility in a developing solution under action of acid or a component that exhibits decreased solubility in a developing solution under action of acid.

Further, the component (A) may be a component that generates acid upon exposure. In such a case, as the component (A), the polymeric compound of the fourth aspect of the present invention can be applied.

When the resist composition of the present invention is a "negative resist composition for alkali developing process" that forms a negative-tone resist pattern in an alkali developing process (or a "positive resist composition for solvent developing process" that forms a positive-tone resist pattern in a solvent developing process), as the component (A), a base component (A-2) that is soluble in an alkali developing solution (hereafter, this base component is sometimes referred to as "component (A-2)") is preferably used, and a cross-linking component is further added. In such a resist composition, when acid is generated upon exposure, the action of the acid causes cross-linking between the component (A-2) and the cross-linking component. As a result, the solubility of the resist composition in an alkali developing solution is decreased (the solubility of the resist composition in an organic developing solution is increased). Therefore, in the formation of a resist pattern, by conducting selective exposure of a resist film formed by applying the resist composition to a substrate, the exposed portions become insoluble in an alkali developing solution (soluble in an organic developing solution), whereas the unexposed portions remain soluble in an alkali developing solution (insoluble in an organic developing solution), and hence, a negative resist pattern can be formed by conducting development using an alkali developing solution. On the other hand, when an organic developing solution is used as the developing solution, a positive resist pattern can be formed.

As the component (A-2), a resin that is soluble in an alkali developing solution (hereafter, referred to as "alkali-soluble resin") is used.

Examples of the alkali soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have the hydrogen atom bonded to the carbon atom on the α-position substituted with a substituent or polycycloolefin resin having a sulfoneamide group, as disclosed in U.S. Pat. No. 6,949,325; an acrylic resin which may have the hydrogen atom bonded to the carbon atom on the α-position substituted with a substituent and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linking agent added is preferably within a range from 1 to 50 parts by weight, relative to 100 parts by weight of the alkali-soluble resin.

In the case where the resist composition of the present invention is a resist composition which forms a positive pattern in an alkali developing process and a negative pattern in a solvent developing process (i.e., a positive type resist composition for alkali developing process) or a resist composition which forms a negative paten in a solvent developing process (i.e., a negative type resist composition for solvent developing process), as a component (A), it is preferable to use a base component (A-1) (hereafter, referred to as "component (A-1)") which exhibits increased polarity by the action of acid.

By using the component (A-1), since the polarity of the base component changes prior to and after exposure, an excellent development contrast can be obtained not only in an alkali developing process, but also in a solvent developing process.

More specifically, in the case of applying an alkali developing process, the component (A-1) is substantially insoluble in an alkali developing solution prior to exposure, but when acid is generated upon exposure, the action of this acid causes an increase in the polarity of the base component, thereby increasing the solubility of the component (A-1) in an alkali developing solution. Therefore, in the formation of a resist pattern, by conducting selective exposure of a resist film formed by applying the resist composition to a substrate, the exposed portions change from an insoluble state to a soluble state in an alkali developing solution, whereas the unexposed portions remain insoluble in an alkali developing solution, and hence, a positive resist pattern can be formed by alkali developing.

On the other hand, in the case of a solvent developing process, the component (A-1) exhibits high solubility in an organic developing solution prior to exposure, and when acid is generated upon exposure, the polarity of the component (A-1) is increased by the action of the generated acid, thereby decreasing the solubility of the component (A-1) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern.

In the resist composition of the present invention, the component (A) is preferably a component (A-1).

For example, when the component (A) is a component (A-1), the resist composition may be used in a method of forming a positive-tone resist pattern in an alkali developing process, or in a method of forming a negative-tone resist pattern in a solvent developing process.

[Polymeric Compound (A1)]

When the component (A) is component (A-1), the component (A-1) preferably includes a polymeric compound (A1) which has a structural unit (a1) containing an acid decomposable group that exhibits increased polarity by the action of acid (hereafter, sometimes referred to as "component (A1)").

(Structural Unit (a1))

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of acid to form a polar group.

Examples of the polar group include a carboxy group, a hydroxy group, an amino group and a sulfo group (—$SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

Here, the "acid dissociable group" include:

(i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

The acid dissociable group is not particularly limited, and any of the groups that have been conventionally proposed as acid dissociable groups for the base resins of chemically amplified resists can be used.

Examples of the acid dissociable group for protecting the carboxy group or hydroxy group as a polar group include the acid dissociable group represented by general formula (a1-r-1) shown below (hereafter, referred to as "acetal-type acid dissociable group").

[Chemical Formula 40]

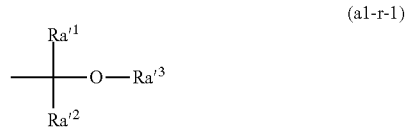

(a1-r-1)

In the formula, $Ra'^1$ and $Ra'^2$ represents a hydrogen atom or an alkyl group; and $Ra'^3$ represents a hydrocarbon group, provided that $Ra'^3$ may be bonded to $Ra'^1$ or $Ra'^2$ to form a ring.

In the formula (a1-r-1), it is preferable that at least one of $Ra'^1$ and $Ra'^2$ represents a hydrogen atom, and it is more preferable that both of $Ra'^1$ and $Ra'^2$ represent a hydrogen atom.

In the case where $Ra'^1$ or $Ra'^2$ is an alkyl group, as the alkyl group, the same alkyl groups as those described above the for the substituent which may be bonded to the carbon atom on the α-position of the aforementioned α-substituted acrylate can be mentioned, and an alkyl group of 1 to 5 carbon atoms is preferable. Specific examples thereof include a linear or branched alkyl group. Specific examples of the linear or branched alkyl group include a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In the formula (a1-r-1), examples of the hydrocarbon group for $Ra'^3$ include a linear, branched or cyclic alkyl group.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group, a neopentyl group, a 1,1-diethylpropyl group and a 2,2-dimethylbutyl group, and an isopropyl group is desirable.

When $Ra'^3$ is a cyclic hydrocarbon group, the hydrocarbon group may be either an aliphatic group or an aromatic group, and may be either a polycyclic group or a monocyclic group.

As the monocyclic alicyclic hydrocarbon group, a group in which one hydrogen atom has been removed from a monocycloalkane is preferable. The monocycloalkane preferably has 3 to 6 carbon atoms, and specific examples thereof include cyclopentane and cyclohexane.

As the polycyclic alicyclic hydrocarbon group, a group in which one hydrogen atom has been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

When the cyclic hydrocarbon group for $Ra'^3$ is an aromatic hydrocarbon group, examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which one hydrogen atom has been removed from the aforementioned aromatic hydrocarbon ring (aryl group); and a group in which one hydrogen atom of the aforementioned aryl group has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atoms, more preferably 1 or 2, and most preferably 1.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Examples of the acid dissociable group for protecting the carboxy group as a polar group include the acid dissociable group represented by general formula (a1-r-2) shown below. Hereafter, with respect to the acid dissociable group represented by the following formula (a1-r-2), the acid dissociable group constituted of alkyl groups is referred to as "tertiary ester-type acid dissociable group".

[Chemical Formula 41]

(a1-r-2)

In the formula, $Ra'^4$ to $Ra'^6$ each independently represents a hydrocarbon group,
provided that $Ra'^5$ and $Ra'^6$ may be mutually bonded to form a ring.

As the hydrocarbon group for $Ra'^4$ to $Ra'^6$, the same groups as those described above for $Ra'^3$ can be mentioned.

$Ra'^4$ is preferably an alkyl group of 1 to 5 carbon atoms. In the case where $Ra'^5$ and $Ra'^6$ are mutually bonded to form a ring, a group represented by general formula (a1-r2-1) shown below. On the other hand, in the case where $Ra'^4$ to $Ra'^6$ are not mutually bonded and independently represent a hydrocarbon group, the group represented by general formula (a1-r2-2) shown below can be mentioned.

[Chemical Formula 42]

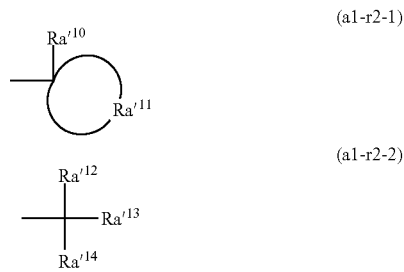

In the formulae, $Ra'^{10}$ represents an alkyl group of 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represents a hydrocarbon group.

In the formula (a1-r2-1), as the alkyl group of 1 to 10 carbon atoms for $Ra'^{10}$, the same groups as described above for the linear or branched alkyl group for $Ra'^3$ in the formula (a1-r-1) are preferable. In the formula (a1-r2-1), as the aliphatic cyclic group which is formed by $Ra'^{11}$ and the carbon group having $Ra'^{10}$ bonded thereto, the same groups as those described above for the cyclic alkyl group for $Ra'^3$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^3$ in the formula (a1-r-1), it is still more preferable that the alkyl group is a linear alkyl group of 1 to 5 carbon atoms, and it is particularly preferable that the alkyl group is a methyl group or an ethyl group.

In the formula (a1-r2-2), it is preferable that $Ra'^{13}$ is the same group as described above for the linear, branched or cyclic alkyl group for $Ra'^3$ in the formula (a1-r-1).

Among these, the same cyclic alkyl group as those describe above for $Ra'^3$ is more preferable.

Specific examples of the group represented by formula (a1-r2-1) are shown below. In the present specification, "*" in the formula represents a valence bond.

[Chemical Formula 43]

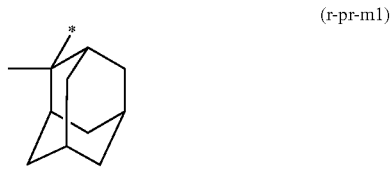

(r-pr-m1)

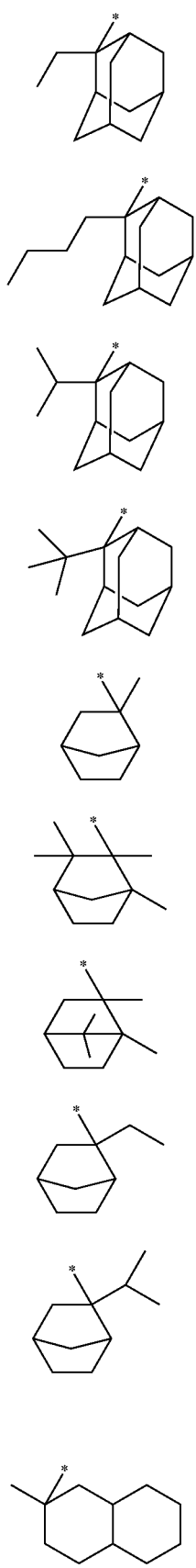
(r-pr-m2)
(r-pr-m3)
(r-pr-m4)
(r-pr-m5)
(r-pr-m6)
(r-pr-m7)
(r-pr-m8)
(r-pr-m9)
(r-pr-m10)
(r-pr-m11)
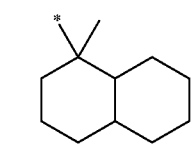
(r-pr-m12)
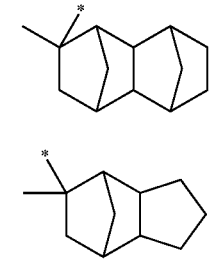
(r-pr-m13)
(r-pr-m14)
(r-pr-m15)
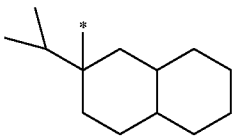
(r-pr-m16)
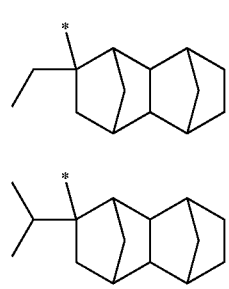
(r-pr-m17)
[Chemical Formula 44]
(r-pr-s1)
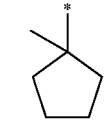
(r-pr-s2)
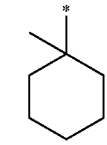
(r-pr-s3)
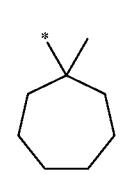
(r-pr-s4)
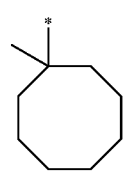

(r-pr-s5) 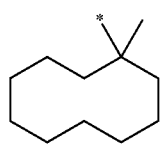
(r-pr-s6) 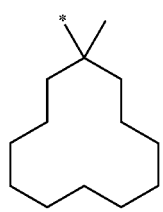
(r-pr-s7) 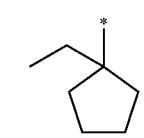
(r-pr-s8) 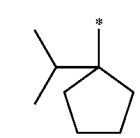
(r-pr-s9) 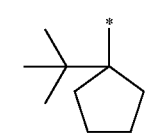
(r-pr-s10) 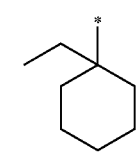
(r-pr-s11) 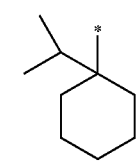
(r-pr-s12) 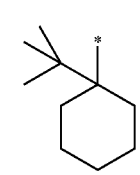
(r-pr-s13) 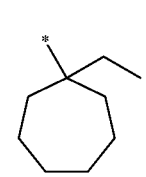
(r-pr-s14) 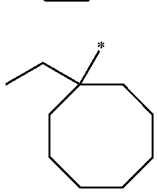
(r-pr-s15) 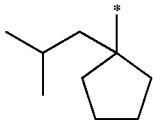
(r-pr-s16) 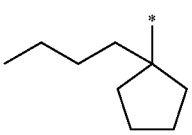
(r-pr-s17) 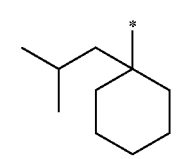
(r-pr-s18) 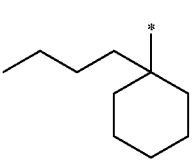
Specific examples of the group represented by formula (a1-r2-2) are shown below.
[Chemical Formula 45]
(r-pr-cm1) 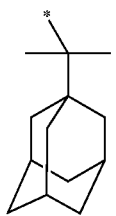
(r-pr-cm2) 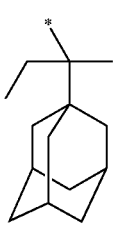
(r-pr-cm3) 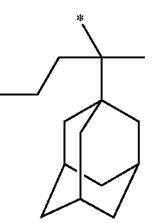
(r-pr-cm4) 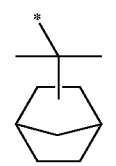

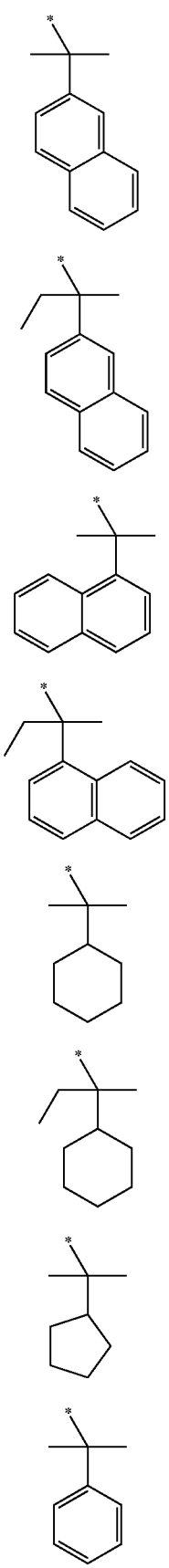

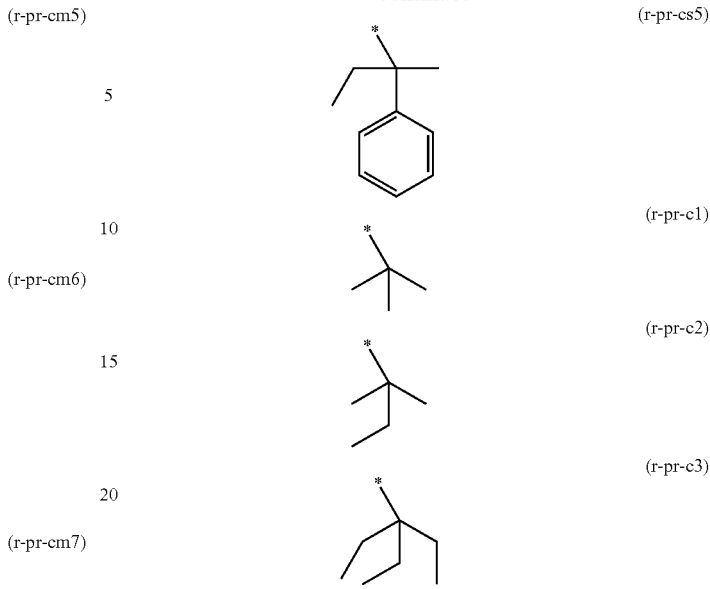

Examples of the acid dissociable group for protecting a hydroxy group as a polar group include the acid dissociable group represented by general formula (a1-r-3) shown below (hereafter, referred to as "tertiary alkyloxycarbonyl-type acid dissociable group").

[Chemical Formula 46]

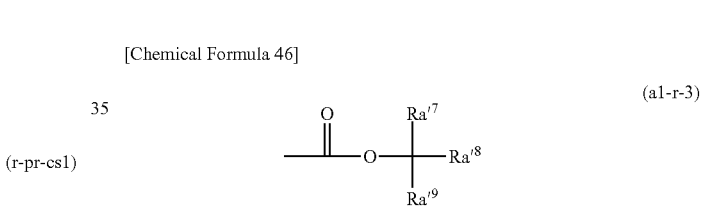

(a1-r-3)

In the formula, $Ra'^7$ to $Ra'^9$ each independently represents an alkyl group.

In the formula (a1-r-3), $Ra'^7$ to $Ra'^9$ is each preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent and contains an acid decomposable group which exhibits increased polarity by the action of acid; a structural unit derived from an acrylamide which contains an acid decomposable group which exhibits increased polarity by the action of acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

Specific examples of preferable structural units for the structural unit (a1) include structural units represented by general formula (a1-1) or (a1-2) shown below.

[Chemical Formula 47]

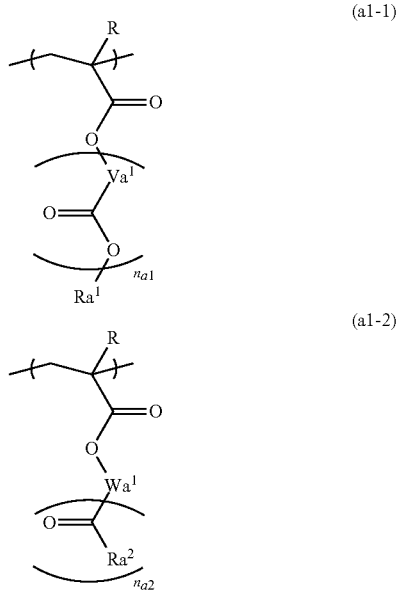

In the formulae, R represents a hydrogen atom, an alkyl group of 1 to 5 carbon atoms or a halogenated alkyl group of 1 to 5 carbon atoms; $Va^1$ represents a divalent hydrocarbon group which may have an ether bond; $n_{a1}$ represents 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents 1 to 3; and $Ra^2$ represents an acid dissociable group represented by the aforementioned formula (a1-r-1) or (a1-r-3).

In general formula (a1-1), as the alkyl group of 1 to 5 carbon atoms represented by R, a linear or branched alkyl group of 1 to 5 carbon atoms is preferable, and specific examples include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

The hydrocarbon group for $Va^1$ may be either an aliphatic hydrocarbon group or an aromatic hydrocarbon group. An "aliphatic hydrocarbon group" refers to a hydrocarbon group that has no aromaticity. The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

Further, $Va^1$ may have an ether bond (—O—) interposed between the carbon atoms of the aforementioned divalent hydrocarbon group. $Va^1$ may have one ether bond or two ether bonds.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable, and specific examples include a methylene group [—CH$_2$—], an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, a branched alkylene group is preferable, and specific examples include alkylalkylene groups, e.g., alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$) CH$_2$CH$_2$—. As the alkyl group within the alkylalkylene group, a linear alkyl group of 1 to 5 carbon atoms is preferable.

As examples of the aliphatic hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of a linear or branched aliphatic hydrocarbon group, and a group in which the alicyclic hydrocarbon group is interposed within a linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane.

As the polycyclic alicyclic hydrocarbon group, a group in which two hydrogen atoms have been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for $Va^1$ preferably has 5 to 30 carbon atoms, more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom.

Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (for example, a group in which one hydrogen atom has been removed from an aryl group within an arylalkyl group such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atoms, more preferably 1 or 2, and most preferably 1.

In the aforementioned formula (a1-2), the hydrocarbon group for $Wa^1$ having a valency of $n_{a2}+1$ may be either an aliphatic hydrocarbon group or an aromatic hydrocarbon group. The aliphatic hydrocarbon group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $n_{a2}+1$ is preferably divalent, trivalent or tetravalent, and divalent or trivalent is more preferable.

Specific examples of structural units represented by the general formula (a1-1) are shown below.

[Chemical Formula 48]

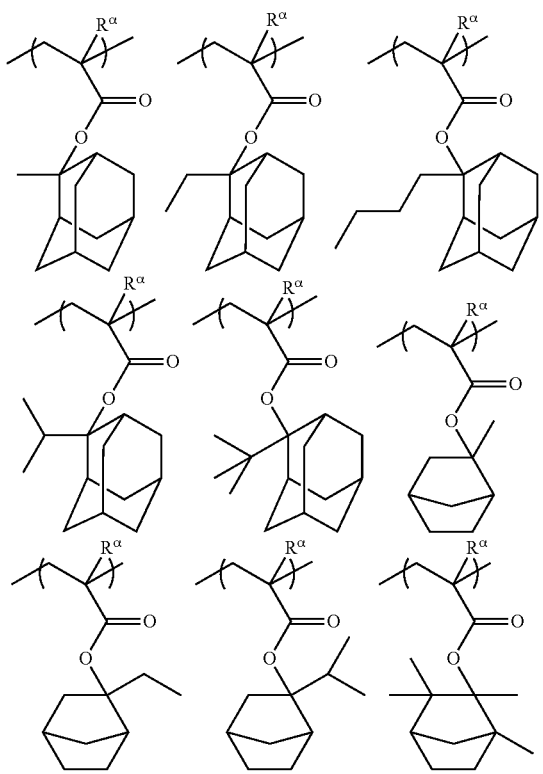

-continued

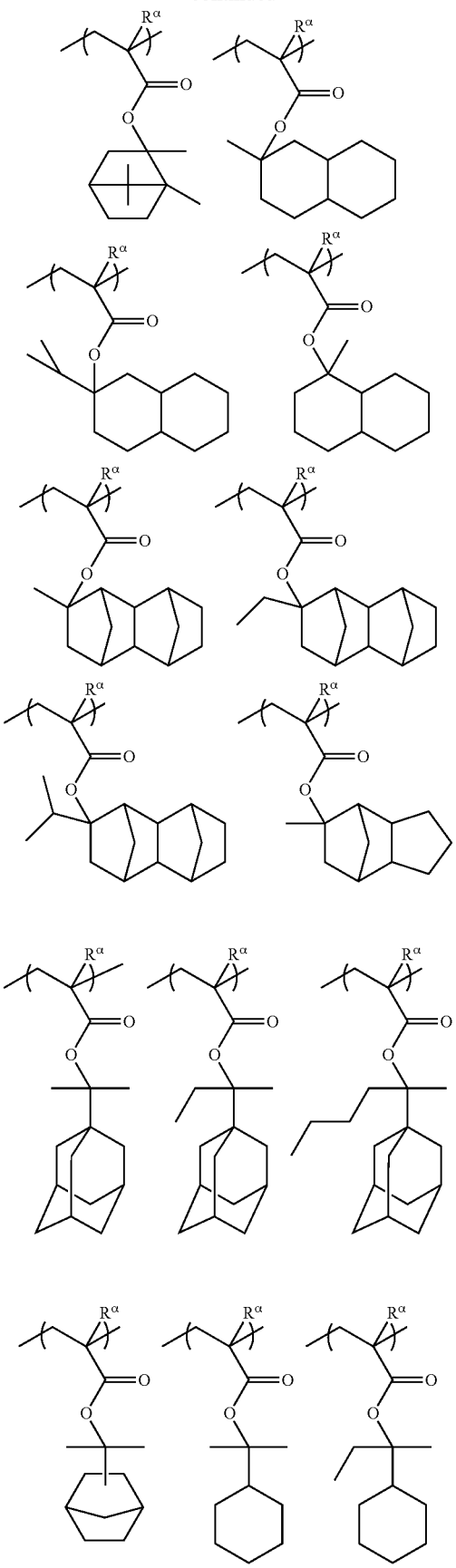

-continued
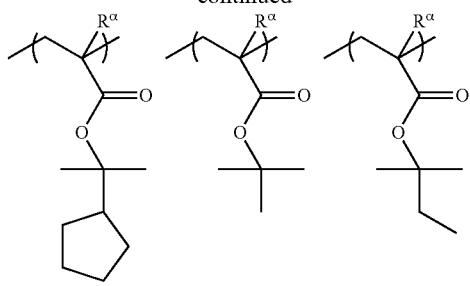
[Chemical Formula 49]
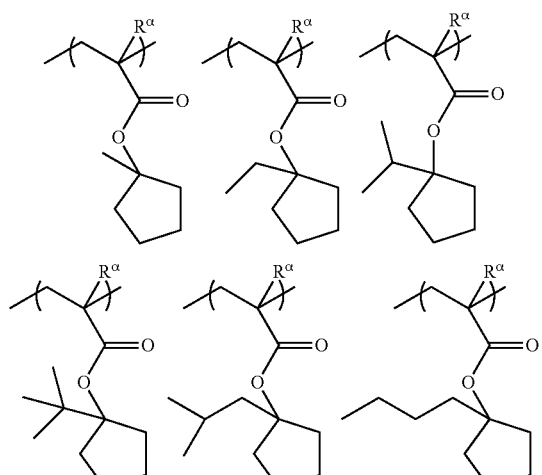
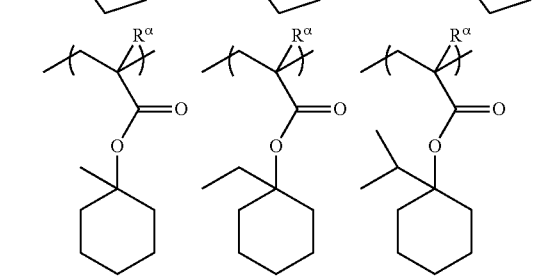
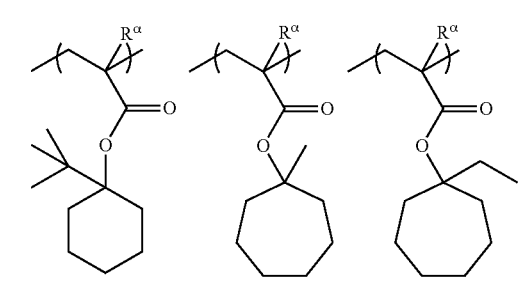
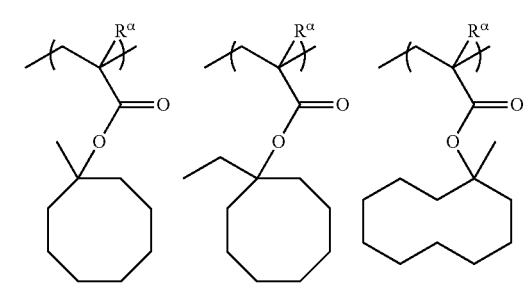
-continued
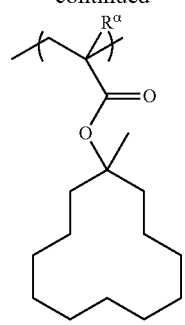
[Chemical Formula 50]
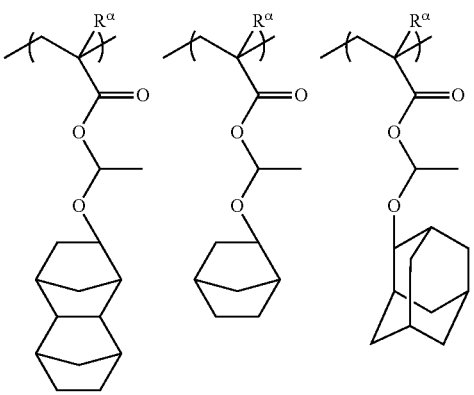
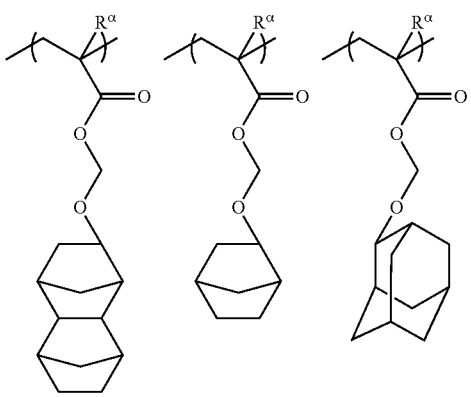
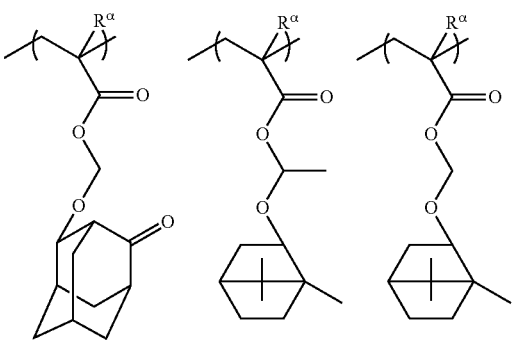

-continued
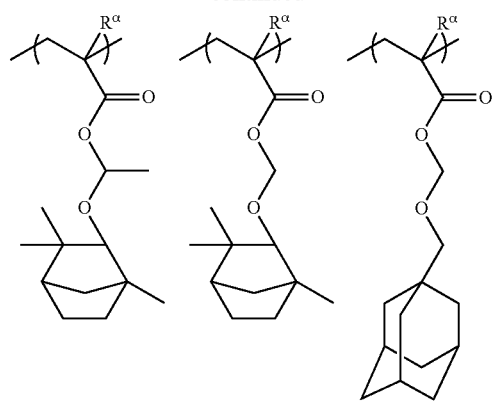
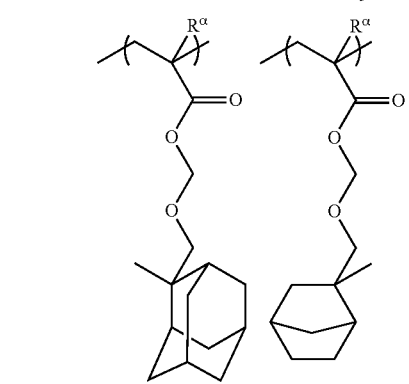
[Chemical Formula 51]
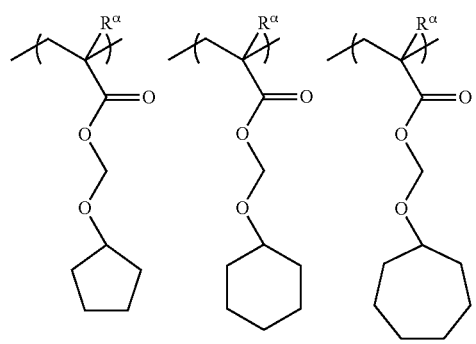
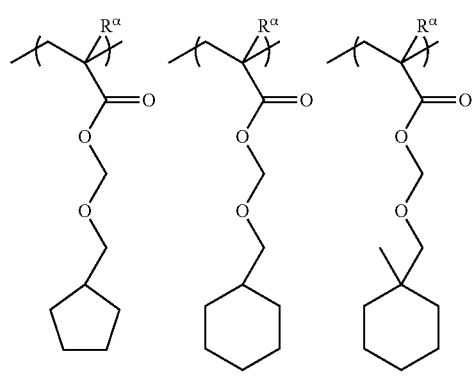
-continued
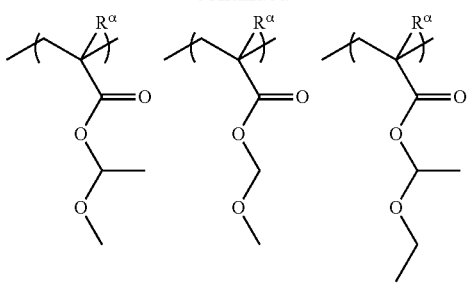
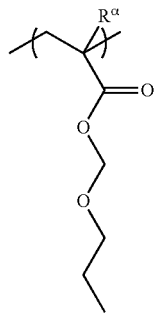
[Chemical Formula 52]
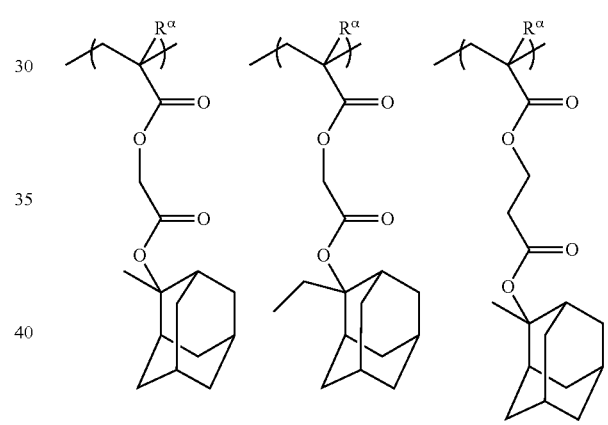
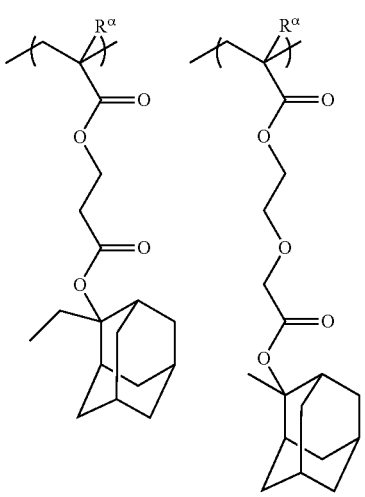

-continued
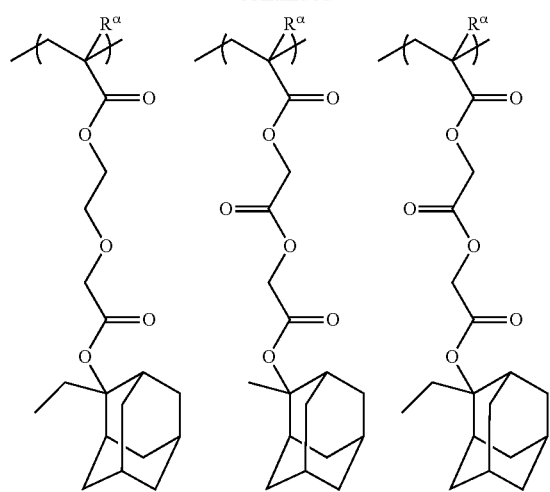
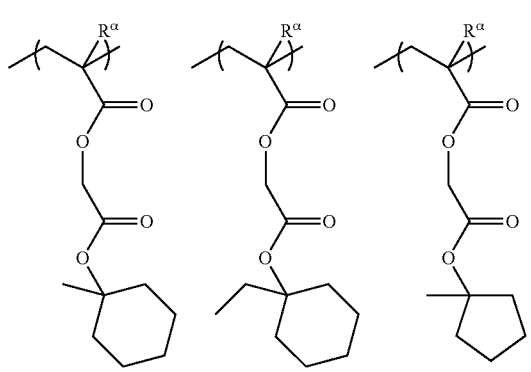
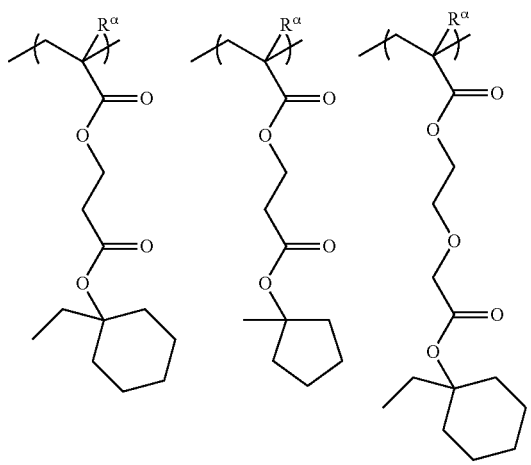
-continued
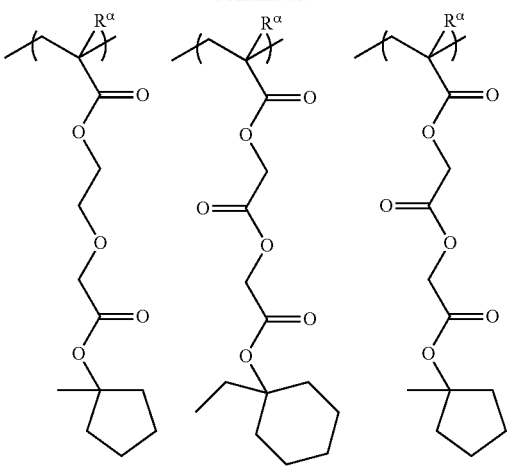
In the formulae, $R^{\alpha}$ is the same as defined above.
Specific examples of structural units represented by the general formula (a1-2) are shown below.
[Chemical Formula 53]
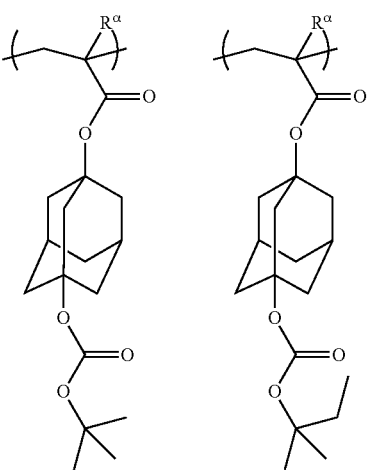
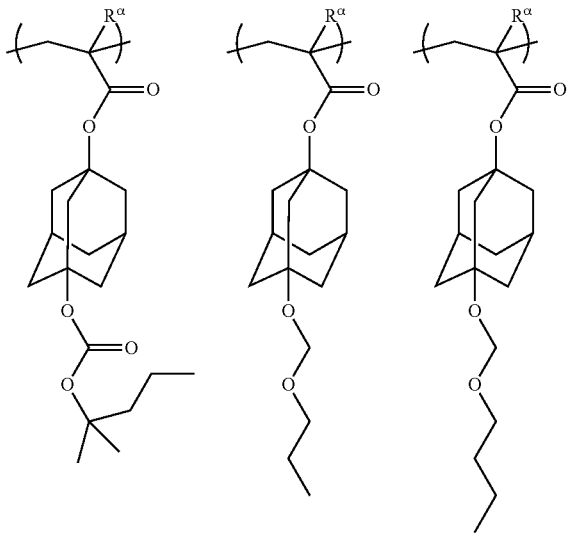

-continued

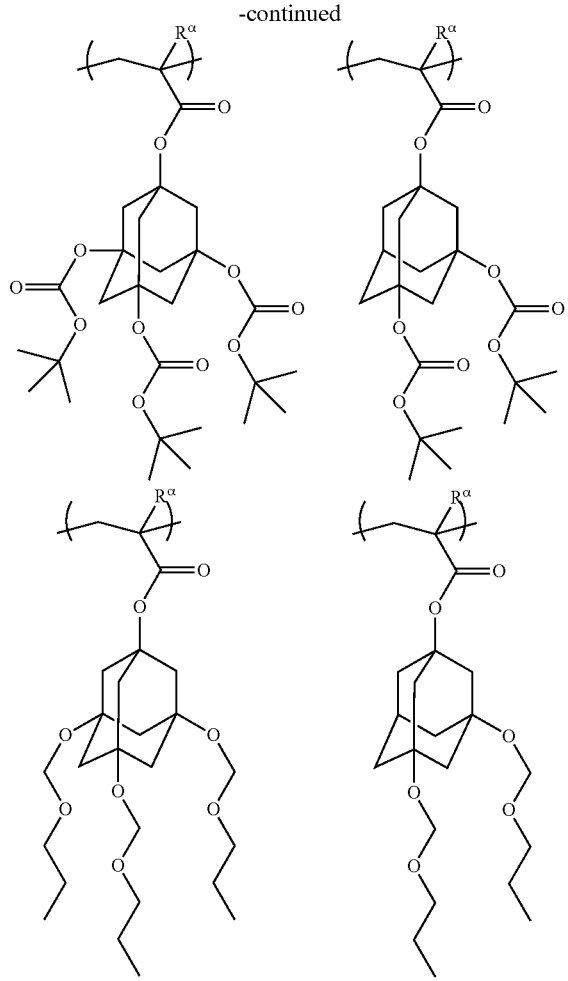

In the formulae, $R^\alpha$ is the same as defined above.

As the structural unit (a1) contained in the component (A1), 1 type of structural unit may be used, or 2 or more types may be used.

In the component (A1), the amount of the structural unit (a1) based on the combined total of all structural units constituting the component (A1) is preferably 20 to 80 mol %, more preferably 20 to 75 mol %, and still more preferably 25 to 70 mol %. When the amount of the structural unit (a1) is at least as large as the lower limit of the above-mentioned range, a resist pattern can be easily formed, and various lithography properties such as sensitivity, resolution, LWR and the like are improved. On the other hand, when the amount of the structural unit (a1)) is no more than the upper limit of the above-mentioned range, a good balance can be achieved with the other structural units.

(Other Structural Units)

The component (A1) may be further include a structural unit other than the structural unit (a1), as well as the structural unit (a1). As the other structural unit, any other structural unit which cannot be classified as the aforementioned structural units can be used without any particular limitation, and any of the multitude of conventional structural units used within resist resins for ArF excimer lasers or KrF excimer lasers (and particularly for ArF excimer lasers) can be used. For example, a structural units (a2) to (a4) and a structural unit (a6) shown below can be used.

Structural Unit (a2):

The structural unit (a2) is a structural unit which contains a lactone-containing cyclic group, an —$SO_2$— containing cyclic group or a carbonate-containing cyclic group.

When the component (A1) is used for forming a resist film, the lactone-containing cyclic group, the —$SO_2$— containing cyclic group or the carbonate-containing cyclic group within the structural unit (a2) is effective in improving the adhesion between the resist film and the substrate.

The aforementioned structural unit (a1) which contains a lactone-containing cyclic group, an —$SO_2$— containing cyclic group or a carbonate-containing cyclic group falls under the definition of the structural unit (a2); however, such a structural unit is regarded as a structural unit (a1), and does not fall under the definition of the structural unit (a2).

The term "lactone-containing cyclic group" refers to a cyclic group including a ring containing a —O—C(═O)— structure (lactone ring). The term "lactone ring" refers to a single ring containing a —O—C(═O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples include structural units represented by general formulae (a2-r-1) to (a2-r-7) shown below.

[Chemical Formula 54]

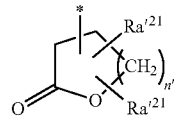

(a2-r-1)

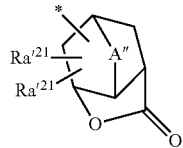

(a2-r-2)

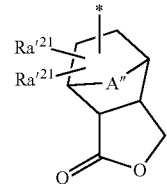

(a2-r-3)

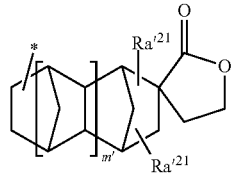

(a2-r-4)

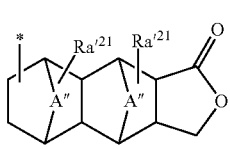
(a2-r-5)

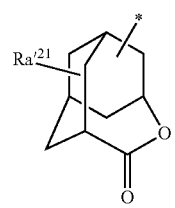
(a2-r-6)

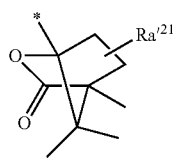
(a2-r-7)

In the formulae, each $Ra'^{21}$ independently represents a hydrogen atom, an alkyl group, an alkoxy group, a halogen atom, a halogenated alkyl group, a hydroxy group, —COOR″, —OC(═O)R″, a hydroxyalkyl group or a cyano group; R″ represents a hydrogen atom or an alkyl group; A″ represents an oxygen atom, a sulfur atom or an alkylene group of 1 to 5 carbon atoms which may contain an oxygen atom (—O—) or a sulfur atom (—S—); n' represents an integer of 0 to 2; and m' represents 0 or 1.

In the formulae (a2-r-2), (a2-r-3) and (a2-r-5), as the alkylene group of 1 to 5 carbon atoms for A″, a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—. As A″, an alkylene group of 1 to 5 carbon atoms or —O— is preferable, more preferably an alkylene group of 1 to 5 carbon atoms, and most preferably a methylene group.

In the formulae (a2-r-1) to (a2-r-7), the alkyl group for $Ra'^{21}$ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or an ethyl group is preferable, and a methyl group is particularly desirable.

The alkoxy group for $Ra'^{21}$ is preferably an alkoxy group of 1 to 6 carbon atoms.

Further, the alkoxy group is preferably a linear or branched alkoxy group. Specific examples of the alkoxy groups include the aforementioned alkyl groups for $Ra'^{21}$ having an oxygen atom (—O—) bonded thereto.

As examples of the halogen atom for $Ra'^{21}$, a fluorine atom, chlorine atom, bromine atom and iodine atom can be given. Among these, a fluorine atom is preferable.

Examples of the halogenated alkyl group for $Ra'^{21}$ include groups in which part or all of the hydrogen atoms within the aforementioned alkyl groups has been substituted with the aforementioned halogen atoms. As the halogenated alkyl group, a fluorinated alkyl group is preferable, and a perfluoroalkyl group is particularly desirable.

With respect to —COOR″ and —OC(═O)R″ for $Ra'^{21}$, R″ represents a hydrogen atom or an alkyl group.

The alkyl group for R″ may be linear, branched or cyclic, and preferably has 1 to 15 carbon atoms.

When R″ represents a linear or branched alkyl group, it is preferably an alkyl group of 1 to 10 carbon atoms, more preferably an alkyl group of 1 to 5 carbon atoms, and most preferably a methyl group or an ethyl group.

When R″ is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for $Ra'^{21}$ preferably has 1 to 6 carbon atoms, and specific examples thereof include the aforementioned alkyl groups for the substituent in which at least one hydrogen atom has been substituted with a hydroxy group.

Specific examples of the group represented by the aforementioned general formulae (a2-r-1) to (a2-r-7) are shown below.

[Chemical Formula 55]

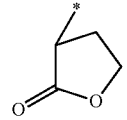
(r-Ic-1-1)

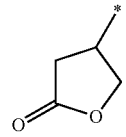
(r-Ic-1-2)

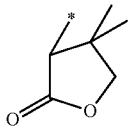
(r-Ic-1-3)

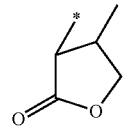
(r-Ic-1-4)

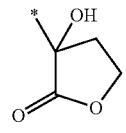
(r-Ic-1-5)

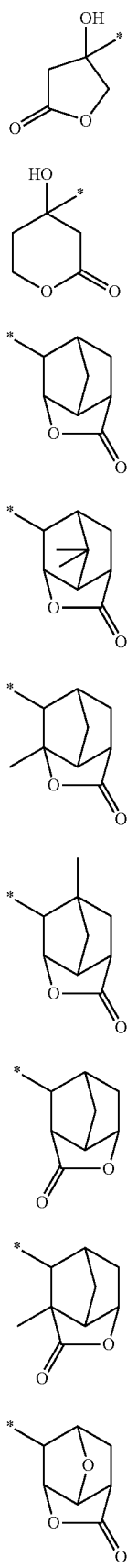
(r-Ic-1-6)
(r-Ic-1-7)
(r-Ic-2-1)
(r-Ic-2-2)
(r-Ic-2-3)
(r-Ic-2-4)
(r-Ic-2-5)
(r-Ic-2-6)
(r-Ic-2-7)
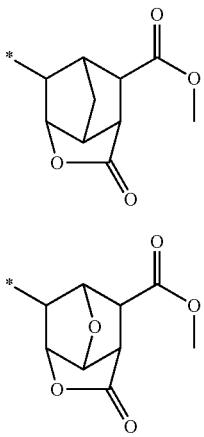
(r-Ic-2-8)
(r-Ic-2-9)
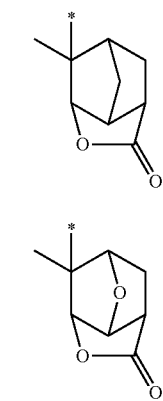
(r-Ic-2-10)
(r-Ic-2-11)
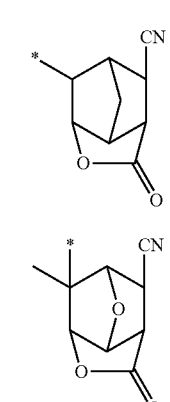
(r-Ic-2-12)
(r-Ic-2-13)
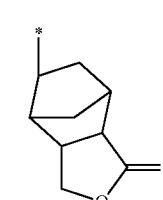
(r-Ic-3-1)
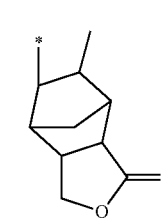
(r-Ic-3-2)

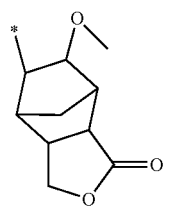 (r-Ic-3-3)
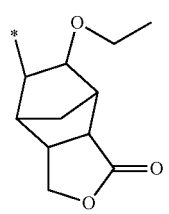 (r-Ic-3-4)
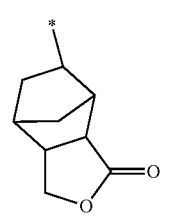 (r-Ic-3-5)
[Chemical Formula 56]
(r-Ic-4-1)
(r-Ic-4-2)
(r-Ic-4-3)
(r-Ic-4-4)
(r-Ic-4-5)
(r-Ic-4-6)
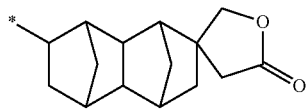 (r-Ic-4-7)
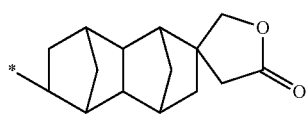 (r-Ic-4-8)
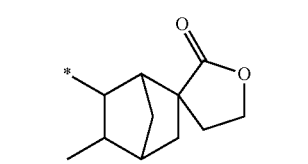 (r-Ic-4-9)
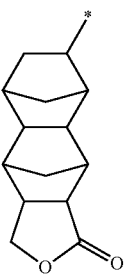 (r-Ic-5-1)
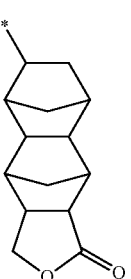 (r-Ic-5-2)
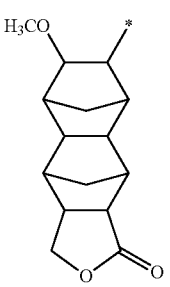 (r-Ic-5-3)
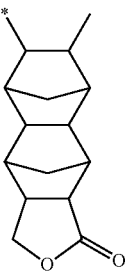 (r-Ic-5-4)

-continued (r-Ic-6-1)

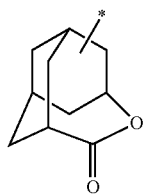

(r-Ic-7-1)

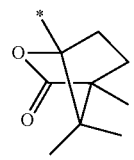

An "—SO$_2$— containing cyclic group" refers to a cyclic group having a ring containing —SO$_2$— within the ring structure thereof, i.e., a cyclic group in which the sulfur atom (S) within —SO$_2$— forms part of the ring skeleton of the cyclic group. The ring containing —SO$_2$— within the ring skeleton thereof is counted as the first ring. A cyclic group in which the only ring structure is the ring that contains —SO$_2$— in the ring skeleton thereof is referred to as a monocyclic group, and a group containing other ring structures is described as a polycyclic group regardless of the structure of the other rings. The —SO$_2$— containing cyclic group may be either a monocyclic group or a polycyclic group.

As the —SO$_2$— containing cyclic group, a cyclic group containing —O—SO$_2$— within the ring skeleton thereof, i.e., a cyclic group containing a sultone ring in which —O—S- within the —O—SO$_2$— group forms part of the ring skeleton thereof is particularly desirable.

More specific examples of the —SO$_2$— containing cyclic group include groups represented by general formulae (a5-r-1) to (a5-r-4) shown below.

[Chemical Formula 57]

(a5-r-1)

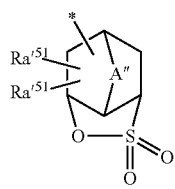

(a5-r-2)

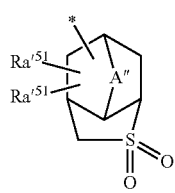

(a5-r-3)

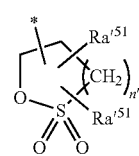

-continued (a5-r-4)

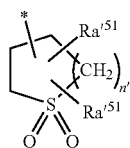

In the formulae, each Ra'$^{51}$ independently represents a hydrogen atom, an alkyl group, an alkoxy group, a halogen atom, a halogenated alkyl group, a hydroxy group, —COOR'', —OC(=O)R'', a hydroxyalkyl group or a cyano group; R'' represents a hydrogen atom or an alkyl group; A'' represents an oxygen atom, a sulfur atom or an alkylene group of 1 to 5 carbon atoms which may contain an oxygen atom or a sulfur atom; and n' represents an integer of 0 to 2.

In general formulae (a5-r-1) to (a5-r-4), A'' is the same as defined for A'' in general formulae (a2-r-2), (a2-r-3) and (a2-r-5).

Examples of the alkyl group, alkoxy group, halogen atom, halogenated alkyl group, —COOR'', —OC(=O)R'' and hydroxyalkyl group for Ra'$^{51}$ include the same groups as those described above in the explanation of Ra'$^{21}$ in the general formulae (a2-r-1) to (a2-r-7).

Specific examples of the group represented by the aforementioned general formulae (a5-r-1) to (a5-r-4) are shown below. In the formulae shown below, "Ac" represents an acetyl group.

[Chemical Formula 58]

(r-sl-1-1)

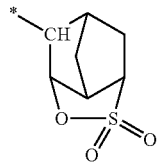

(r-sl-1-2)

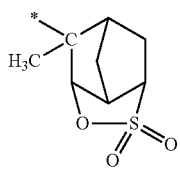

(r-sl-1-3)

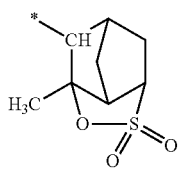

(r-sl-1-4)

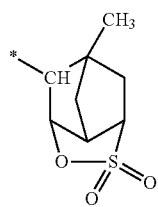

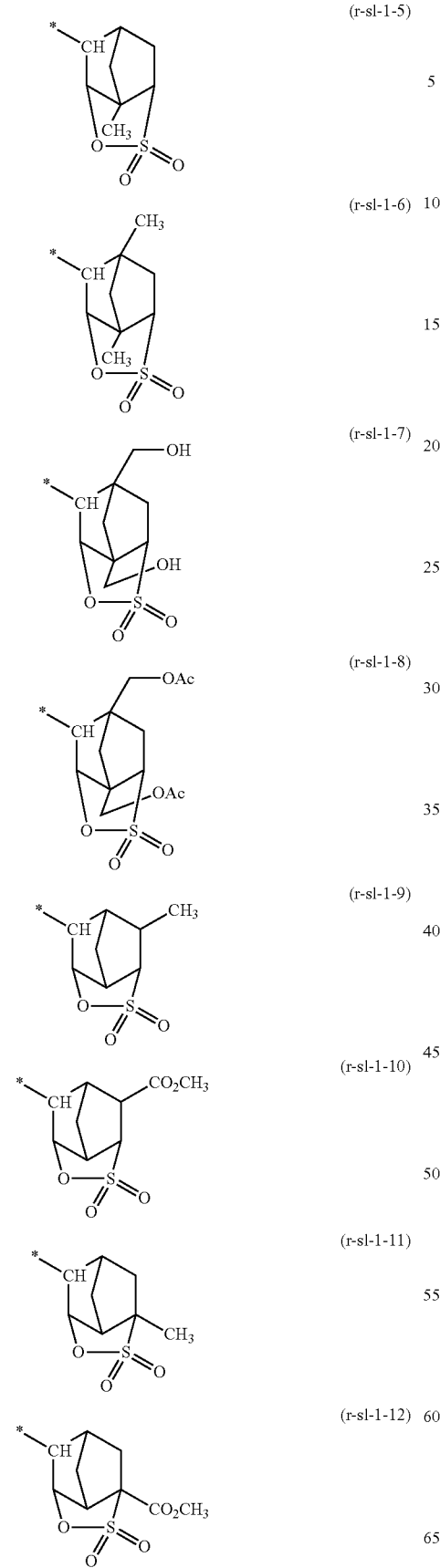
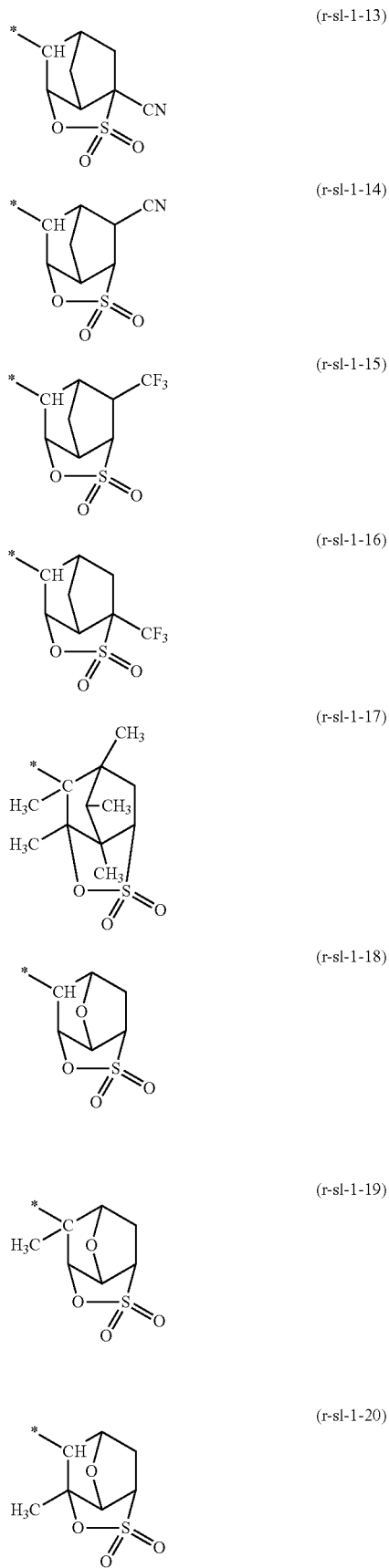

[Chemical Formula 59]
(r-sl-1-21) 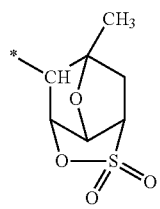
(r-sl-1-22) 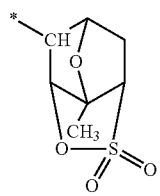
(r-sl-1-23) 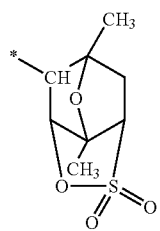
(r-sl-1-24) 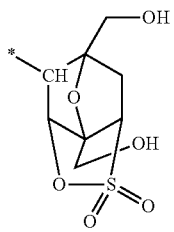
(r-sl-1-25) 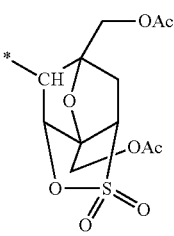
(r-sl-1-26) 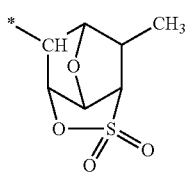
(r-sl-1-27) 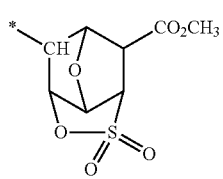
(r-sl-1-28) 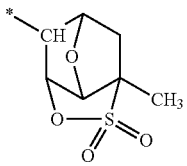
(r-sl-1-29) 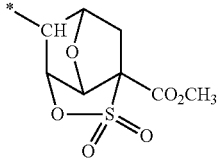
(r-sl-1-30) 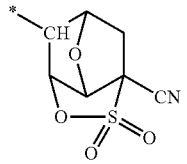
(r-sl-1-31) 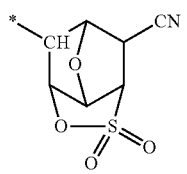
(r-sl-1-32) 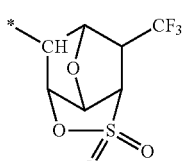
(r-sl-1-33) 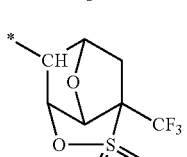
[Chemical Formula 60]
(r-sl-2-1) 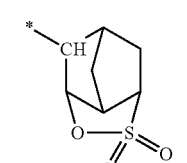
(r-sl-2-2) 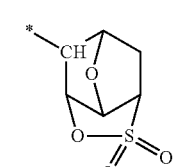
(r-sl-3-1) 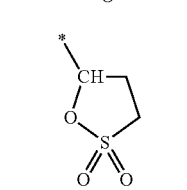

(r-sl-4-1)

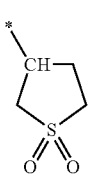

The term "carbonate-containing cyclic group" refers to a cyclic group including a ring containing a —O—C(=O)—O— structure (carbonate ring) in the ring skeleton thereof. The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 61]

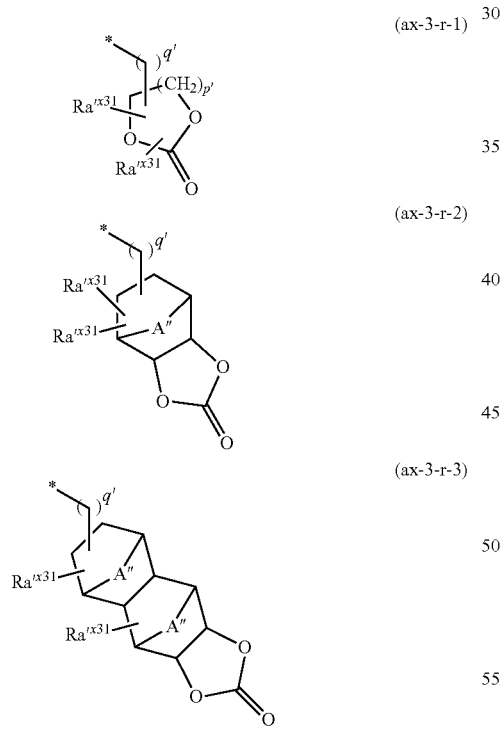

In the formulae, each $Ra'^{x31}$ independently represents a hydrogen atom, an alkyl group, an alkoxy group, a halogen atom, a halogenated alkyl group, a hydroxy group, —COOR'', —OC(=O)R'', a hydroxyalkyl group or a cyano group; R'' represents a hydrogen atom or an alkyl group; A'' represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-1) to (ax3-r-3), A'' is the same as defined for A'' in general formulae (a2-r-2), (a2-r-3) and (a2-r-5).

Examples of the alkyl group, alkoxy group, halogen atom, halogenated alkyl group, —COOR'', —OC(=O)R'' and hydroxyalkyl group for $Ra'^{31}$ include the same groups as those described above in the explanation of $Ra'^{21}$ in the general formulae (a2-r-1) to (a2-r-7).

Specific examples of the group represented by the aforementioned general formulae (ax3-r-1) to (ax3-r-3) are shown below.

[Chemical Formula 62]

(r-cr-1-1)

(r-cr-1-2)

(r-cr-1-3)

(r-cr-1-4)

(r-cr-1-5)

(r-cr-1-6)

(r-cr-1-6)
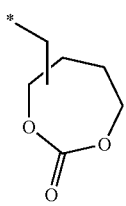
(r-cr-2-1)
(r-cr-2-2)
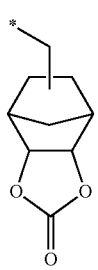
(r-cr-2-3)
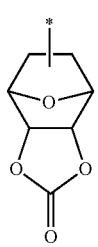
(r-cr-2-4)
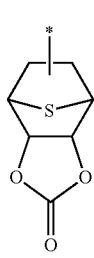
(r-cr-3-1)
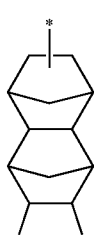
(r-cr-3-2)
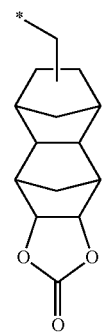
(r-cr-3-3)
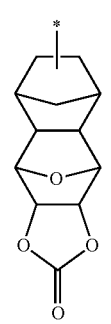
(r-cr-3-4)
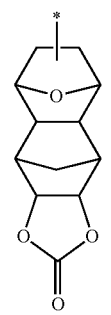
(r-cr-3-5)
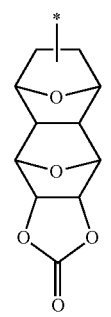
The structural unit (a2) is preferably a structural unit represented by general formula (a2-1) shown below.
[Chemical Formula 63]
(a2-1)
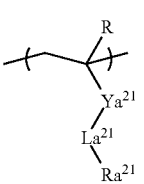

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —COO—, —CONHCO— or —CONHCS—; R' represents a hydrogen atom or a methyl group, provided that when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

In the formula (a2-1), R is the same as defined above.

The divalent linking group for $Ya^{21}$ is not particularly limited, and preferable examples thereof include a divalent hydrocarbon group which may have a substituent and a divalent linking group containing a hetero atom.

(Divalent Hydrocarbon Group which May have a Substituent)

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Specific examples of the linear or branched aliphatic hydrocarbon group include the same group as exemplified above for $Va^1$ in the aforementioned formula (a1-1).

The linear or branched aliphatic hydrocarbon group may or may not have a substituent. Examples of the substituent include a fluorine atom, a fluorinated alkyl group of 1 to 5 carbon atoms, and a carbonyl group.

As examples of the hydrocarbon group containing a ring in the structure thereof, a cyclic aliphatic hydrocarbon group which may have a substituent containing a hetero atom in the ring structure thereof (a group in which two hydrogen atoms have been removed from an aliphatic hydrocarbon ring), a group in which the cyclic aliphatic hydrocarbon group is bonded to the terminal of a linear or branched aliphatic hydrocarbon group, and a group in which the cyclic aliphatic group is interposed within a linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

Specific examples of the cyclic aliphatic hydrocarbon group include the same group as exemplified above for $Va^1$ in the aforementioned formula (a1-1).

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

In the cyclic aliphatic hydrocarbon group, part of the carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—

Specific examples of the aromatic hydrocarbon group as a divalent hydrocarbon group include the same group as exemplified above for $Va^1$ in the aforementioned formula (a1-1).

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is most desirable.

As the alkoxy group, the halogen atom and the halogenated alkyl group for the substituent, the same groups as the aforementioned substituent groups for substituting a hydrogen atom within the cyclic aliphatic hydrocarbon group can be used.

(Divalent Linking Group Containing a Hetero Atom)

With respect to a divalent linking group containing a hetero atom, a hetero atom is an atom other than carbon and hydrogen, and examples thereof include an oxygen atom, a nitrogen atom, a sulfur atom and a halogen atom.

In the case where $Ya^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (wherein H may be substituted with a substituent such as an alkyl group or an acyl group), —S—, —S(=O)$_2$—, —S(=O)$_2$—O— and a group represented by general formula —$Y^{21}$—O—$Y^{22}$—, $Y^{21}$—O—, —$Y^{21}$—C(=O)—O—, —[$Y^{21}$—C(=O)—O]$_{m''}$—$Y^{22}$— or —$Y^{21}$—O—C(=O)—$Y^{22}$— [in the formulae, each of $Y^{21}$ and $Y^{22}$ independently represents a divalent hydrocarbon group which may have a substituent, O represents an oxygen atom, and m" represents an integer of 0 to 3].

When the divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In formula —$Y^{21}$—O—$Y^{22}$—, —$Y^{21}$—O—, —$Y^{21}$—C(=O)—O—, —[$Y^{21}$—C(=O)—O]$_{m''}$—$Y^{22}$— or —$Y^{21}$—O—C(=O)—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula $—[Y^{21}—C(=O)—O]_{m''}—Y^{22}—$, m″ represents an integer of 0 to 3, preferably an integer of 0 to 2, more preferably 0 or 1, and particularly preferably 1. Namely, it is particularly desirable that the group represented by the formula $—[Y^{21}—C(=O)—O]_{m''}—Y^{22}—$ is a group represented by the formula $—Y^{21}—C(=O)—O—Y^{22}—$. Among these, a group represented by the formula $—(CH_2)_{a'}—C(=O)—O—(CH_2)_{b'}—$ is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

$Ya^{21}$ preferably represents an ester bond [—C(=O)—O—], an ether bond (—O—), a linear or branched alkylene group, a combination of these, or a single bond.

In the formula (a2-1), $Ra^{21}$ represents a lactone-containing cyclic group, an —SO$_2$-containing cyclic group or a carbonate-containing cyclic group.

Preferable examples of the lactone-containing cyclic group, the —SO$_2$— containing cyclic group and the carbonate-containing cyclic group for $Ra^{21}$ include groups represented by the aforementioned formulae (a2-r-1) to (a2-r-7), groups represented by general formulae (a5-r-1) to (a5-r-4) and groups represented by general formulae (ax3-r-1) to (ax3-r-3).

Among the examples shown above, a lactone-containing cyclic group or —SO$_2$-containing cyclic group is preferable, a group represented by the general formula (a2-r-1), (a2-r-2) or (a5-r-1) is more preferable, and a group represented by any one of the chemical structures (r-1c-1-1) to (r-1c-1-7), (r-1c-2-1) to (r-1c-2-13), (r-s1-1-1) and (r-s1-1-18) is still more preferable.

As the structural unit (a2) contained in the component (A1), 1 type of structural unit may be used, or 2 or more types may be used.

When the component (A1) contains the structural unit (a2), the amount of the structural unit (a2) based on the combined total of all structural units constituting the component (A1) is preferably 1 to 80 mol %, more preferably 10 to 70 mol %, still more preferably 10 to 65 mol %, and particularly preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties such as DOF and CDU and pattern shape can be improved.

Structural Unit (a3):

The structural unit (a3) is a structural unit containing a polar group-containing aliphatic hydrocarbon group (provided that the structural units that fall under the definition of structural units (a1) and (a2) are excluded).

When the component (A1) includes the structural unit (a3), it is presumed that the hydrophilicity of the component (A1) is enhanced, thereby contributing to improvement in resolution.

Examples of the polar group include a hydroxyl group, a cyano group, a carboxyl group, or a hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups may be monocyclic or polycyclic, and can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that includes an aliphatic polycyclic group that contains a hydroxyl group, a cyano group, a carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulae (a3-1), (a3-2) and (a3-3) shown below are preferable.

[Chemical Formula 64]

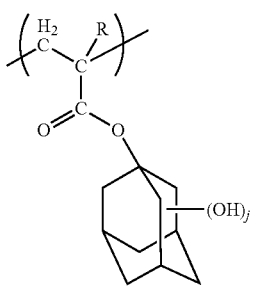

(a3-1)

-continued

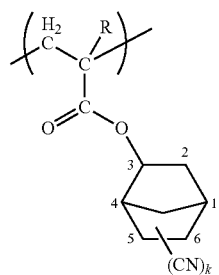

(a3-2)

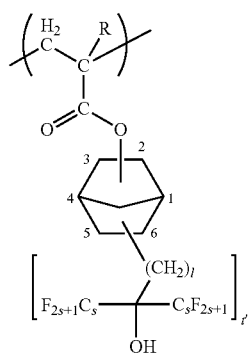

(a3-3)

In the formulae, R is as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. 1 is preferably 1. s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 type of structural unit may be used, or 2 or more types may be used.

When the component (A1) contains the structural unit (a3), the amount of the structural unit (a3) within the component (A1) based on the combined total of all structural units constituting the component (A1) is preferably 5 to 50 mol %, more preferably 5 to 40 mol %, and still more preferably 5 to 25 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

Structural Unit (a4):

The structural unit (a4) is a structural unit containing an acid non-dissociable, aliphatic cyclic group.

When the component (A1) includes the structural unit (a4), dry etching resistance of the resist pattern to be formed is improved. Further, the hydrophobicity of the component (A1) is further improved. Increase in the hydrophobicity contributes to improvement in terms of resolution, shape of the resist pattern and the like, particularly in an organic solvent developing process.

An "acid non-dissociable, aliphatic cyclic group" in the structural unit (a4) refers to a cyclic group which is not dissociated by the action of the acid (e.g., acid generated from the components (A) or a component (B) described later) generated upon exposure, and remains in the structural unit.

As the structural unit (a4), a structural unit which contains a non-acid-dissociable aliphatic cyclic group, and is also derived from an acrylate ester is preferable. Examples of this cyclic group include the same groups as those described above in relation to the aforementioned structural unit (a1), and any of the multitude of conventional groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include structural units represented by general formulae (a4-1) to (a4-7) shown below.

[Chemical Formula 65]

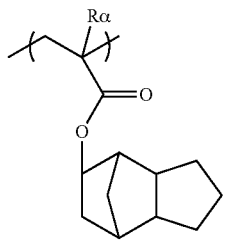

(a4-1)

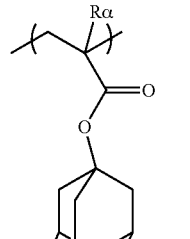

(a4-2)

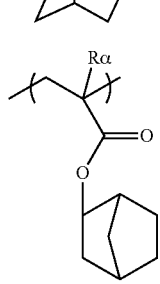

(a4-3)

-continued

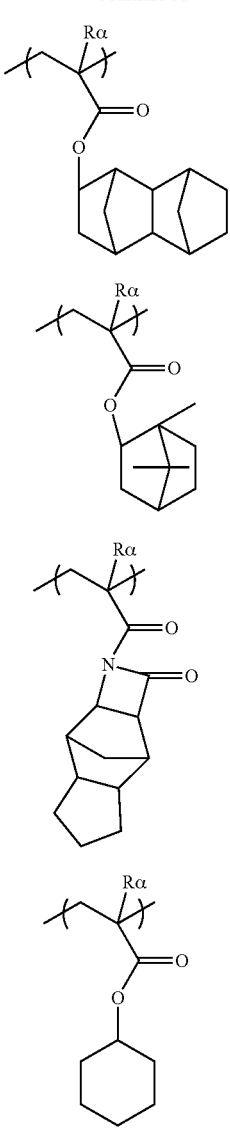

In the formulae, $R^\alpha$ is the same as defined above.

As the structural unit (a4) contained in the component (A1), 1 type of structural unit may be used, or 2 or more types may be used.

When the component (A1) includes the structural unit (a4), the amount of the structural unit (a4) based on the combined total of all structural units constituting the component (A1) is preferably 1 to 30 mol %, and more preferably 3 to 20 mol %. When the amount of the structural unit (a4) is at least as large as the lower limit of the above-mentioned range, the effect of using the structural unit (a4) can be satisfactorily achieved. On the other hand, when the amount of the structural unit (a4) is no more than the upper limit of the above-mentioned range, a good balance can be achieved with the other structural units.

Structural Unit (a6):

The structural unit (a6) is a structural unit derived from the compound of the third aspect of the present invention and has a polymerizable group (i.e., compound (m)).

The compound (m) and structural unit (a6) are the same as defined above.

As the structural unit (a6) contained in the component (A1), 1 type of structural unit may be used, or 2 or more types may be used.

When the component (A1) contains the structural unit (a6), the amount of the structural unit (a6) based on the combined total of all structural units constituting the component (A1) is preferably 1 to 40 mol %, more preferably 1.5 to 35 mol %, still more preferably 2 to 30 mol %, and particularly preferably 3 to 20 mol %.

When the amount of the structural unit (a6) is at least as large as the lower limit of the above-mentioned range, when the component (A1) is used as a base resin for a resist composition, a resist pattern can be easily obtained and lithography properties can be improved. On the other hand, when the amount of the structural unit (a6) is no more than the upper limit of the above-mentioned range, a good balance can be reliably achieved with the other structural units.

The component (A1) is a polymer containing at least the structural unit (a1), and preferably a copolymer having the one or more structural units selected from structural units (a2) to (a4), as well as the structural unit (a1).

Specific examples of the component (A1) include a copolymer consisting of a repeating structure of a structural unit (a1) and a structural unit (a2); a copolymer consisting of a repeating structure of a structural unit (a1)) and a structural unit (a3); a copolymer consisting of a repeating structure of a structural unit (a1), a structural unit (a2) and a structural unit (a3); and a copolymer consisting of a repeating structure of a structural unit (a1), a structural unit (a2), a structural unit (a3) and a structural unit (a4).

In the case where the component (A1) is a polymeric compound which generates acid upon exposure and exhibits changed solubility in a developing solution under action of acid, it is preferable that the polymeric compound is the aforementioned polymeric compound of the fourth aspect of the present invention, and is a copolymer containing a structural unit (a6) and a structural unit (a1).

Specific examples of the component (A1) include a copolymer consisting of a repeating structure of a structural unit (a6) and a structural unit (a1); a copolymer consisting of a repeating structure of a structural unit (a6), a structural unit (a1) and a structural unit (a2); a copolymer consisting of a repeating structure of a structural unit (a6), a structural unit (a1), a structural unit (a2) and a structural unit (a3); and a copolymer consisting of a repeating structure of a structural unit (a6), a structural unit (a1), a structural unit (a2), a structural unit (a3) and a structural unit (a4).

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) is not particularly limited, but is preferably 1.0 to 5.0, more preferably 1.0 to 3.0, and most preferably 1.0 to 2.5. Here, Mn is the number average molecular weight.

The component (A1) can be obtained, for example, by a conventional radical polymerization or the like of the monomers corresponding with each of the structural units, using a radical polymerization initiator such as azobisisobutyronitrile (AIBN) or dimethyl 2,2'-azobis(isobutyrate).

Furthermore, in the component (A1), by using a chain transfer agent such as HS—$CH_2$—$CH_2$-$CH_2$—$C(CF_3)_2$—

OH, a —C(CF$_3$)$_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomers for deriving the corresponding structural units, commercially available monomers may be used, or the monomers may be synthesized by a conventional method.

As the component (A1), one type may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved, such as improvement in MEF and circularity, and reduction of roughness.

In the resist composition of the present invention, the component (A-1) may contain "a base component which exhibits increased polarity under action of acid" other than the component (A1) (hereafter, referred to as "component (A2)").

The component (A2) is not particularly limited, and any of the multitude of conventional base components used within chemically amplified resist compositions (e.g., base resins used within chemically amplified resist compositions for ArF excimer lasers or KrF excimer lasers, preferably ArF excimer lasers) can be used. As the component (A2), one type of base component may be used, or two or more types of base components may be used in combination.

In the resist composition of the present invention, as the component (A), one type may be used, or two or more types may be used in combination.

In the resist composition of the present invention, the amount of the component (A) can be appropriately adjusted depending on the thickness of the resist film to be formed, and the like.

<Component (B)>

When the resist composition of the present invention includes the component (B), as the component (B), the acid generator of the fifth aspect of the present invention is used. By virtue of using the component (B), lithography properties are improved.

As the component (B), one type may be used alone, or two or more types may be used in combination.

When the resist composition of the present invention contains the component (B), the amount of the component (B) relative to 100 parts by weight of the component (A) is preferably within a range from 0.5 to 60 parts by weight, more preferably from 1 to 50 parts by weight, and still more preferably from 1 to 40 parts by weight.

When the amount of the component (B) is within the above-mentioned range, formation of a resist pattern can be satisfactorily performed. Further, by virtue of the above-mentioned range, when each of the components are dissolved in an organic solvent, a uniform solution can be obtained and the storage stability becomes satisfactory.

<Other Components>

The resist composition of the present invention may contain a component other than the component (A) and the component (B).

Moreover, the resist composition of the present invention may include an acid diffusion control agent component (hereafter, frequently referred to as "component (D)"), in addition to the component (A), or in addition to the component (A) and the component (B).

[Component (D)]

The component (D) functions as an acid diffusion control agent, i.e., a quencher which traps the acid generated from the component (B) and the like upon exposure.

The component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

Component (D1)

When a resist pattern is formed using a resist composition containing the component (D1), the contrast between exposed portions and unexposed portions is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) function as a quencher.

[Chemical Formula 66]

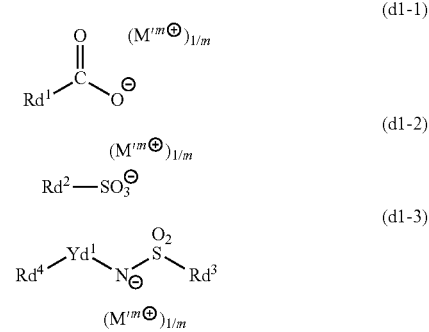

In the formulae, Rd$^1$ to Rd$^4$ represents a cyclic group which may have a substituent, a chain-like alkyl group which may have a substituent or a chain-like alkenyl group which may have a substituent; provided that, in the formula (d1-2), the carbon atom within the Rd$^2$ adjacent to the sulfur atom has no fluorine atom bonded thereto; Yd$^1$ represents a single bond or a divalent linking group; m represents an integer of 1 or more; and M$^{m+}$ each independently represents an organic cation having a valency of m.

{Component (d1-1)}

Anion Moiety

In formula (d1-1), Rd$^1$ represents a cyclic group which may have a substituent, a chain-like alkyl group which may have a substituent or a chain-like alkenyl group which may have a substituent, and is the same groups as those defined above for R$^{101}$ in the formula (an1-1).

Among these, as the group for Rd$^1$, an aromatic hydrocarbon group which may have a substituent, an aliphatic cyclic group which may have a substituent and a chain-like alkyl group which may have a substituent are preferable. As the substituents which these groups may have, a hydroxyl group, a fluorine atom or a fluorinated alkyl group is preferable.

The aromatic hydrocarbon group is more preferably a phenyl group or a naphthyl group.

Examples of the aliphatic cyclic group include groups in which one or more hydrogen atoms have been removed from a polycycloalkane such as adamantane, norbornane, isobornane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group; and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

When the chain-like alkyl group is a fluorinated alkyl group containing a fluorine atom or a fluorinated alkyl group as a substituent, the fluorinated alkyl group preferably has 1 to 11 carbon atoms, more preferably 1 to 8, and still more preferably 1 to 4. The fluorinated alkyl group may contain an atom other than fluorine. Examples of the atom other than fluorine include an oxygen atom, a carbon atom, a hydrogen atom, a sulfur atom and a nitrogen atom.

As for $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is more preferable.

Specific examples of preferable anion moieties for the component (d1-1) include the same anion moieties as those represented by the formula (an1-4).

Cation Moiety

In formula (d1-1), $M'^{m+}$ represents an organic cation having a valency of m.

The organic cation for $M'^{m+}$ is not particularly limited, and examples thereof include the same cation moieties as those represented by the aforementioned formulae (ca-1) to (ca-4), and cation moieties represented by the aforementioned formulae (ca-1-1) to (ca-1-63) are preferable.

As the component (d1-1), one type of compound may be used, or two or more types of compounds may be used in combination.

{(Component (d1-2)}
Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$ in the formula (an1-1), provided that, the carbon atom within $Rd^2$ group adjacent to the sulfur atom has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, an aliphatic cyclic group which may have a substituent is preferable, and a group in which one or more hydrogen atoms have been removed from adamantane, norbornane, isobornane, tricyclodecane or tetracyclododecane (which may have a substituent); or a group in which one or more hydrogen atoms have been removed from camphor is more preferable.

The hydrocarbon group for $Rd^2$ may have a substituent. As the substituent, the same groups as those described above for substituting the hydrocarbon group (e.g., aromatic hydrocarbon group, aliphatic hydrocarbon group) for $Rd^1$ in the formula (d1-1) can be mentioned.

Specific examples of preferable anion moieties for the component (d1-2) include the same anion moieties as those represented by the formula (an1-1) in which $m_1$ represents 0.

Cation Moiety

In formula (d1-2), $M'^{m+}$ is an organic cation having a valency of m, and is the same as defined for $M'^{m+}$ in the aforementioned formula (d1-1).

As the component (d1-2), one type of compound may be used, or two or more types of compounds may be used in combination.

{(Component (d1-3)}
Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$ in the formula (an1-1), and a cyclic group containing a fluorine atom, a chain-like alkyl group containing a fluorine atom or a chain-like alkenyl group containing a fluorine atom is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$ in the formula (an1-1).

Among these, an alkyl group which may have substituent, an alkoxy group which may have substituent, an alkylene group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are desirable.

As the alkenyl group for $Rd^4$, the same groups as those described above for $R^{101}$ in the formula (an1-1) can be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ in the formula (an1-1) can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits an excellent photoabsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. As such groups, the same divalent linking groups as those described above for $Ya^{21}$ in the formula (a2-1) can be mentioned.

As $Yd^1$, a carbonyl group, an ester bond, an amide bond, an alkylene group or a combination of these groups is preferable. As the alkylene group, a linear or branched alkylene group is more preferable, and a methylene group or an ethylene group is still more preferable.

Specific examples of preferable anion moieties for the component (d1-3) include the same anion moieties as those represented by the formula (an1-2) in which $L^{m1}$ represents a single bond.

Cation Moiety

In formula (d1-3), $M'^{m+}$ is an organic cation having a valency of m, and is the same as defined for $M'^{m+}$ in the aforementioned formula (d1-1).

As the component (d1-3), one type of compound may be used, or two or more types of compounds may be used in combination.

As the component (D1), one type of compound may be used, or two or more types of compounds may be used in combination.

As the component (D1), among the compound of the third aspect of the present invention (or among the acid generator of the fifth aspect of the present invention), it is preferable a compound containing a carboxylate anion, an amide anion (a carbonylamide anion, a carbonylimide anion, a sulfonylamide anion) or a sulfonate anion (provided that, the carbon atom adjacent to the sulfur atom has no fluorine atom bonded thereto) as an anion moiety.

The amount of the component (D1) relative to 100 parts by weight of the component (A) is preferably within a range from 0.5 to 20 parts by weight, more preferably from 0.5 to 10 parts by weight, and still more preferably from 1 to 8 parts by weight.

When the amount of the component (D1) is at least as large as the lower limit of the above-mentioned range, excellent lithography properties and excellent resist pattern shape can be obtained. On the other hand, when the amount of the component (D1) is no more than the upper limit of the above-mentioned range, sensitivity can be maintained at a satisfactory level, and through-put becomes excellent.

Component (D2)

The component (D) may contain a nitrogen-containing organic compound (D2) (hereafter, referred to as "component (D2)") which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkyl amines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkylalcoholamines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxy)ethyl} amine, tris {2-(2-methoxyethoxymethoxy)ethyl} amine, tris {2-(1-methoxyethoxy)ethyl} amine, tris {2-(1-ethoxyethoxy)ethyl} amine, tris {2-(1-ethoxypropoxy)ethyl} amine, tris [2-{2-(2-hydroxyethoxy)ethoxy}ethyl]amine and triethanol amine tri acetate, and triethanolamine triacetate is preferable.

Further, as the component (D2), an aromatic amine may be used.

Examples of aromatic amines include 4-dimethylaminopyridine, pyrrole, indole, pyrazole, imidazole and derivatives thereof, as well as tribenzylamine, 2,6-diisopropyl aniline and N-tert-butoxycarbonylpyrrolidine.

As the component (D2), one type of compound may be used alone, or two or more types may be used in combination.

The component (D2) is typically used in an amount within a range from 0.01 to 5 parts by weight, relative to 100 parts by weight of the component (A). When the amount of the component (D2) is within the above-mentioned range, the shape of the resist pattern and the post exposure stability of the latent image formed by the pattern-wise exposure of the resist layer are improved.

As the component (D), one type of compound may be used, or two or more types of compounds may be used in combination.

When the resist composition of the present invention contains the component (D), the amount of the component (D) relative to 100 parts by weight of the component (A) is preferably within a range from 0.1 to 15 parts by weight, more preferably from 0.3 to 12 parts by weight, and still more preferably from 0.5 to 12 parts by weight.

When the amount of the component (D) is at least as large as the lower limit of the above-mentioned range, various lithography properties (such as roughness) of the resist composition are improved. Further, a resist pattern having an excellent shape can be obtained. On the other hand, when the amount of the component (D) is no more than the upper limit of the above-mentioned range, sensitivity can be maintained at a satisfactory level, and through-put becomes excellent.

[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as "component (E)") selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of phosphorous oxo acid derivatives include esters in which a hydrogen atom within the above-mentioned phosphorous oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phenylphosphinic acid and phosphinic acid esters.

As the component (E), one type may be used alone, or two or more types may be used in combination.

The component (E) is typically used in an amount within a range from 0.01 to 5 parts by weight, relative to 100 parts by weight of the component (A).

[Component (F)]

In the present invention, the resist composition may further include a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of a structural unit (f1) and the aforementioned structural unit (a1); and a copolymer of a structural unit (f1), a structural unit derived from acrylic acid or methacrylic acid and the aforementioned structural unit (a1) are preferable. As the structural unit (a1) to be copolymerized with a structural unit (f1), a structural unit derived from 1-ethyl-1-cyclooctyl(meth)acrylate or a structural unit is preferable.

[Chemical Formula 67]

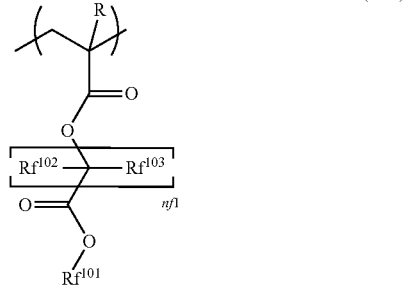

(f1-1)

In the formula, R is the same as defined above; $Rf^{102}$ and $Rf^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R bonded to the carbon atom on the α-position is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $Rf^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ and $Rf^{103}$ include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly desirable. Among these, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 5 carbon atoms is preferable, and a trifluoromethyl group, —$CH_2$—$CF_3$, —$CH_2$—$CF_2$—$CF_3$, —$CH(CF_3)_2$, —$CH_2$—$CH_2$—$CF_3$ and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

The component (F) is typically used in an amount within a range from 0.5 to 10 parts by weight, relative to 100 parts by weight of the component (A).

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

[Component (S)]

The resist composition according to the present invention can be prepared by dissolving the resist materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, PGMEA, PGME, γ-butyrolactone and EL are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL weight ratio or PGMEA:cyclohexanone weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate. In general, the organic solvent is used in an amount such that the solid content of the resist composition becomes within the range from 1 to 20% by weight, and preferably from 2 to 15% by weight.

<<Method of Forming a Resist Pattern>>

The method of forming a resist pattern of the seventh aspect of the present invention includes: forming a resist film on a substrate using a resist composition of the sixth aspect of the present invention; conducting exposure of the resist film; and developing the resist film to form a resist pattern.

The method for forming a resist pattern according to the present invention can be performed, for example, as follows.

Firstly, a resist composition of the present invention is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing. In this manner, a resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic anti-reflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (triple-layer resist method).

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV, and particularly effective to ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which preferably have a boiling point within a range from 70 to 180° C. and more preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used, which are capable of dissolving the component (A) (prior to exposure). Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group within the structure thereof, and an "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterizes the aforementioned solvents within the structure thereof. In such a case, the organic solvent can be classified as any type of the solvent having the characteristic functional group. For example, diethyleneglycol monomethylether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents and nitrile solvents are preferable.

Specific examples of ketone solvents include 1-octanone, 2-octanone, 1-nonanone, 2-nonanone, acetone, 4-heptanone, 1-hexanone, 2-hexanone, diisobutyl ketone, cyclohexanone, methyl cyclohexanone, phenyl acetone, methyl ethyl ketone, methyl isobutyl ketone, acetylacetone, acetonylacetone, ionone, di acetonyl alcohol, acetyl carbinol, acetophenone, methyl naphthyl ketone, isophorone, propylenecarbonate, γ-butyrolactone and methyl amyl ketone (2-heptanone).

As a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate.

As an ester solvent, butyl acetate is preferable.

Examples of nitrile solvents include acetonitrile, propionitrile, valeronitrile, butyronitrile and the like.

If desired, the organic developing solution may have a conventional additive blended. Examples of the additive include surfactants. The surfactant is not particularly limited, and for example, an ionic or non-ionic fluorine and/or silicon surfactant can be used. As the surfactant, a non-ionic surfactant is preferable, and a fluorine surfactant or a silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1 hexanol and 2-hexanol are more preferable.

These organic solvents can be used individually, or at least 2 solvents may be mixed together. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. As the surfactant, the same surfactants as those described above can be mentioned, and a non-ionic surfactant is preferable, and a fluorine surfactant or a silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

EXAMPLES

As follows is a description of examples of the present invention, although the scope of the present invention is by no way limited by these examples.

In the following examples, a compound represented by a chemical formula (1) is designated as "compound (1)", and the same applies for compounds represented by other chemical formulae.

In the NMR analysis, the internal standard for $^{13}$C-NMR was tetramethylsilane (TMS).

<Production Example of Compound>

Example 1

Step of Obtaining Compound 4 from Compound 1:

8.70 g (43.9 mmol) of a compound 1, 10.02 g (52.7 mmol) of a compound 2 and 174 g of toluene were added to a three-necked flask equipped with a thermometer, a reflux tube and a nitrogen inlet tube, and reacted in the presence of a catalytic amount of p-toluenesulfonic acid at 110° C. for 24 hours. Next, the reaction solution was cooled to 25° C., followed by filtration, thereby obtaining 13.8 g of a compound 4.

[Chemical Formula 68]

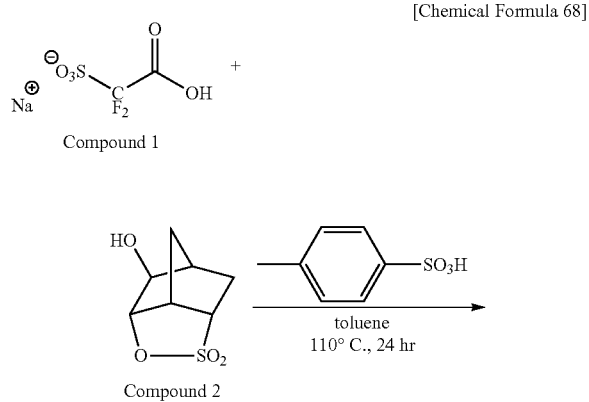

precipitate a compound. Then, the precipitated white solid was separated by filtration, followed by drying, thereby obtaining 19.6 g of a compound 6.

[Chemical Formula 69]

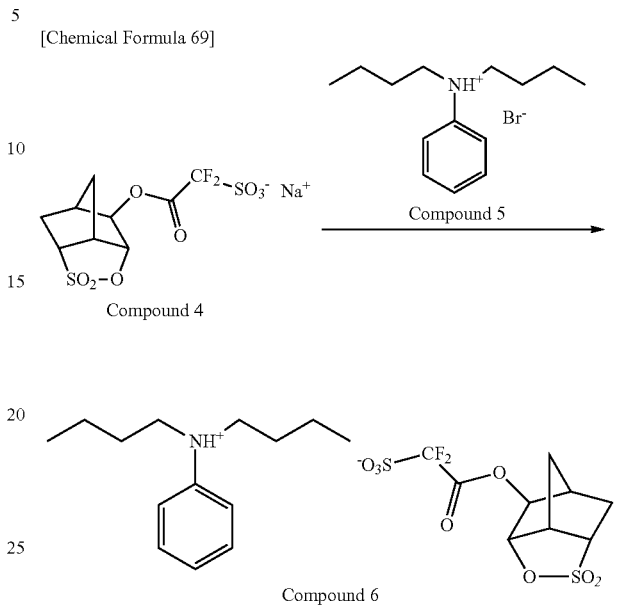

Step of Obtaining Compound 6 from Compound 4:

13.8 g (37.3 mmol) of a compound 4 was added to an eggplant flask, and 12.8 g (44.8 mmol) of a compound 5, 69.1 g of propionitrile and 69.1 g of water were added thereto, followed by stirring for 30 minutes and then extracting the organic layer. The extracted organic layer was washed with an excess amount of water, and added to an excess amount of tert-butyl methyl ether (TBME) in a dropwise manner to Step of Obtaining Compound 8 from Compound 6:

19.6 g (30.5 mmol) of a compound 6 was added to a eggplant flask, and 4.73 g (36.6 mmol) of a compound 7, 84.5 g of acetonitrile and 84.5 g of n-hexane were added thereto, followed by stirring for 30 minutes and then extracting the acetonitrile layer. The extracted acetonitrile layer was washed with n-hexane, and the solvent was distilled off, thereby obtaining a compound 8.

[Chemical Formula 70]

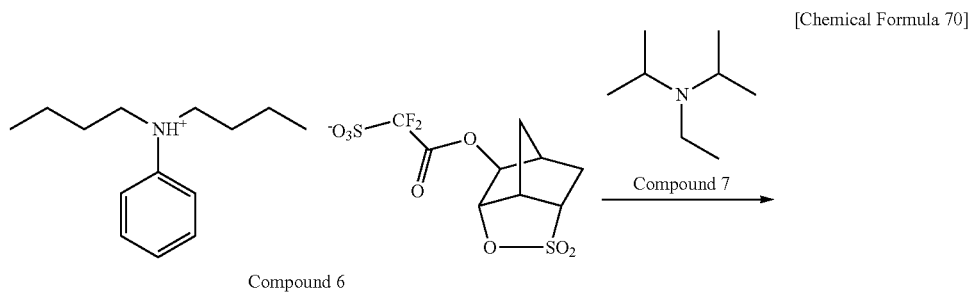

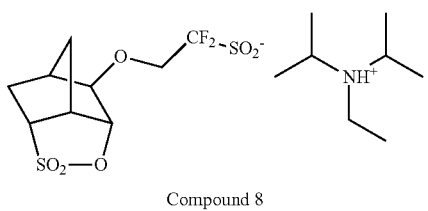

Step of Obtaining Compound 10 from Compound 8:

12.6 g (36.6 mmol) of a compound 9, 84.5g of dichloromethane and 84.5g of water were added to the obtained compound 8, followed by stirring for 30 minutes and then extracting the organic layer. The extracted organic layer was washed with water, and added to an excess amount of TBME in a dropwise manner to precipitate a compound. Then, the precipitated white solid was separated by filtration, followed by drying, thereby obtaining 16.8 g of a compound 10.

[Chemical Formula 71]

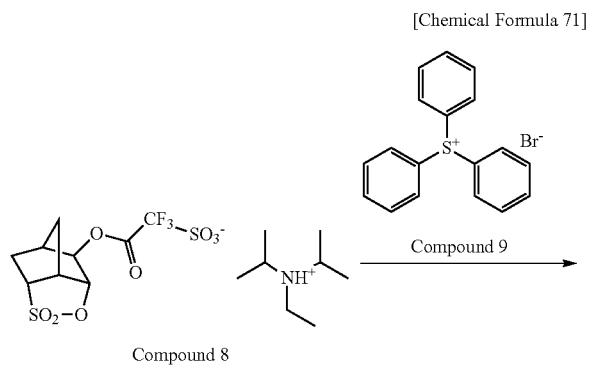

Compound 8

Compound 9

Compound 10

Comparative Example 1

Step of Obtaining Compound 4 from Compound 1:

5.00 g (25.2 mmol) of a compound 1, 5.76 g (30.3 mmol) of a compound 2 and 100 g of toluene were added to a three-necked flask equipped with a thermometer, a reflux tube and a nitrogen inlet tube, and reacted in the presence of a catalytic amount of p-toluenesulfonic acid at 110° C. for 24 hours. Next, the reaction solution was cooled to 25° C., followed by filtration, thereby obtaining 7.85 g of a compound 4.

[Chemical Formula 72]

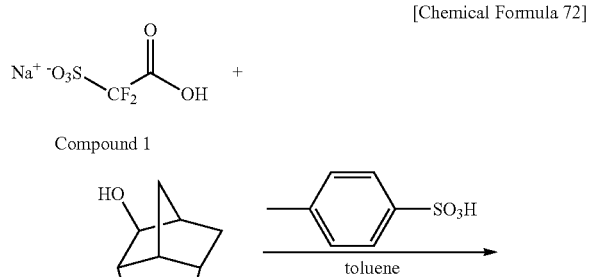

Compound 1

Compound 2

-continued

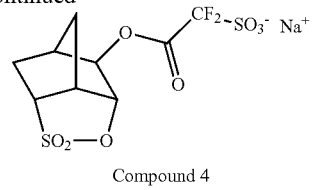

Compound 4

[Compound 4]

The compound 4 as an intermediate has a high hydrophilicity, and therefore, it becomes difficult to conduct washing treatment with water, and to remove impurities satisfactorily.

Step of Obtaining Compound 10 from Compound 4:

7.85 g (21.2 mmol) of a compound 4 was added to a eggplant flask, and 8.73 g (25.4 mmol) of a compound 9, 39.3 g of dichloromethane and 39.3 g of water were added thereto, followed by stirring for 30 minutes and then extracting the organic layer. The extracted organic layer was washed with a small amount of water, and then added to an excess amount of TBME in a dropwise manner to precipitate a compound. Then, the precipitated white solid was separated by filtration, followed by drying, thereby obtaining 11.0 g of a compound 10.

[Chemical Formula 73]

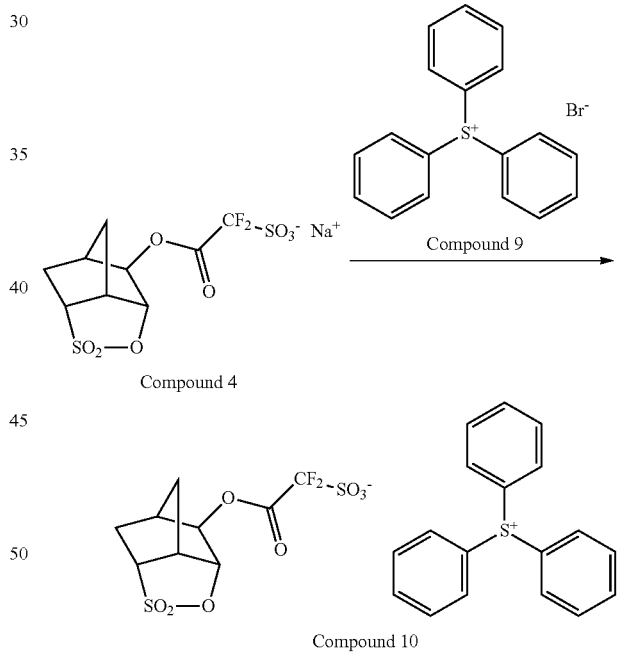

Compound 9

Compound 4

Compound 10

Comparative Example 2

Step of Obtaining Compound 12 from Compound 11:

5.00 g (22.0 mmol) of a compound 11, 5.02 g (26.4 mmol) of a compound 2 and 100 g of toluene were added to a three-necked flask equipped with a thermometer, a reflux tube and a nitrogen inlet tube, and reacted in the presence of a catalytic amount of p-toluenesulfonic acid at 110° C. for 24 hours. Next, the reaction solution was cooled to 25° C., followed by filtration, thereby obtaining a white solid. The obtained white solid was dissolved in dichloromethane, followed by washing with a small amount of water and then extracting the organic layer. The extracted organic layer was added to TBME in a dropwise manner to precipitate a solid. Then, the precipitated solid was separated by filtration, followed by drying, thereby obtaining 8.31 g of a compound 12.

[Chemical Formula 74]

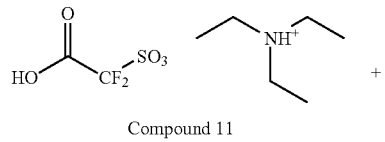

Compound 11

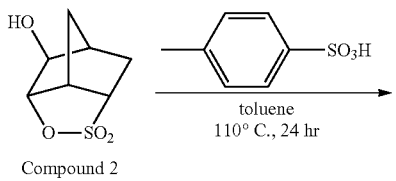

Compound 2

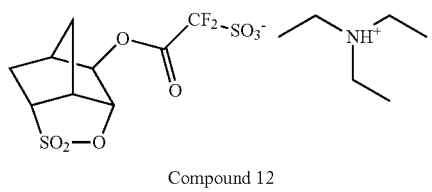

Compound 12

[Compound 12]

The compound 12 as an intermediate can be subjected to washing treatment However, because part of the compound 12 is eluted in water, the yield of the compound 12 is reduced.

Step of Obtaining Compound 10 from Compound 12:

4.15 g (9.24 mmol) of a compound 12 was added to a eggplant flask, and 3.81 g (11.1 mmol) of a compound 9, 20.8 g of dichloromethane and 20.8 g of water were added thereto, followed by stirring for 30 minutes and then extracting the organic layer. The extracted organic layer was washed with a small amount of water, and added to an excess amount of TBME in a dropwise manner to precipitate a compound. Then, the precipitated white solid was separated by filtration, followed by drying, thereby obtaining 6.43 g of a compound 10.

[Chemical Formula 75]

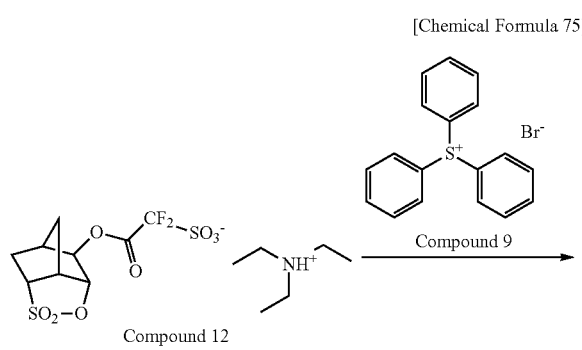

Compound 12 → Compound 9

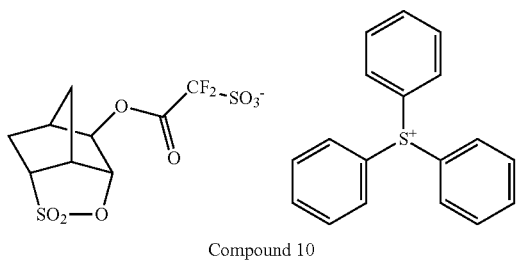

Compound 10

Example 2

Step of Obtaining Compound 15 from Compound 13:

10.0 g (54 3 mmol) of a compound 14 and 6.60 g (65.2 mmol) of triethylamine were added to an eggplant flask, and 50 g of dichioroethane was added thereto. Next, 6.24 g (59.7 mmol) of a compound 13 was added to the eggplant flask in a dropwise manner while cooling with ice, followed by stirring for 1 hour at a room temperature, thereby obtaining a reaction solution containing a compound 15.

[Chemical Formula 76]

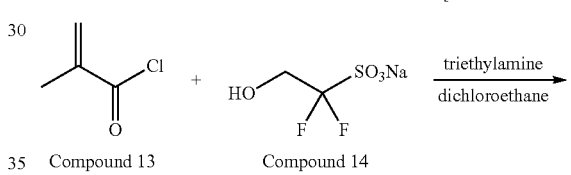

Compound 13    Compound 14

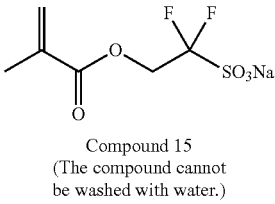

Compound 15
(The compound cannot be washed with water.)

Step of Obtaining Compound 16 from Compound 15: 50 g of water and 23.3 g (81.5 mmol) of a compound 5 were added to the reaction solution containing a compound 15, followed by extracting the organic layer. The organic layer was washed with a diluted hydrochloric acid and then washed with an excess amount of water, and the solvent was distilled off, thereby obtaining 22.5 g of a compound 16.

[Chemical Formula 77]

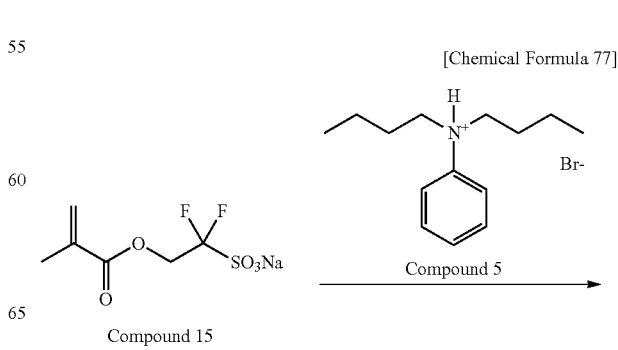

Compound 15 → Compound 5

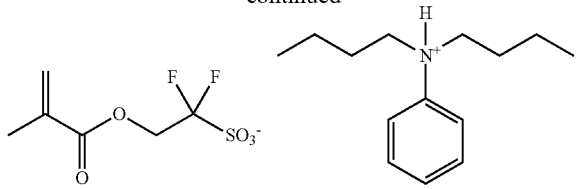

Compound 16
(The compound can be washed with water without elution in water.)

[Compound 16]

The compound 16 is insoluble in water, whereas the compound 51 by-produced as an impurity is soluble in water. Therefore, after conducting salt exchange reaction between the compound 15 and the compound 5, washing treatment with an excess amount of water can be conducted. By this operation, the impurity (i.e., compound 51) can be effectively removed. After this operation, by conducting an operation for introducing a cation moiety (conjugated acid of compound 7) having a low hydrophobicity, a sulfonium cation having a lower hydrophobicity than that of the cation moiety of compound 16 can be introduced.

[Chemical Formula 78]

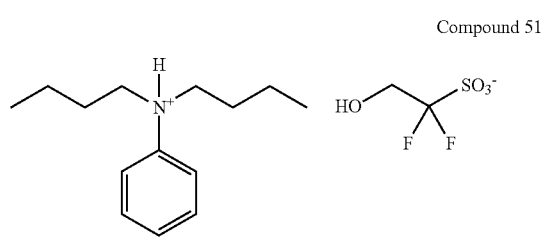

Compound 51

Step of Obtaining Compound 17 from Compound 16:

22.5 g (51 6 mmol) of a compound 16 was dissolved in 90 g of acetonitrile, and 8.00 g (61.9 mmol) of a compound 7 and 90 g of n-heptane were added thereto, followed by extracting the acetonitrile layer. The acetonitrile layer was washed with n-heptane, and the solvent was distilled off, thereby obtaining 18.18 g of a compound 17.

Step of Obtaining Compound 18 from Compound 17:

18.8 g (50.6 mmol) of a compound 17 was dissolved in 94 g of dichloromethane, and 20.8 g (60.7 mmol) of a compound 9 and 94 g of water were added thereto, followed by extracting the dichloromethane layer. The dichloromethane layer was washed with water, and then added to an excess amount of TBME in a dropwise manner to precipitate a solid. Then, the precipitated solid was separated by filtration, followed by drying, thereby obtaining 24.5 g of a compound 18.

[Chemical Formula 80]

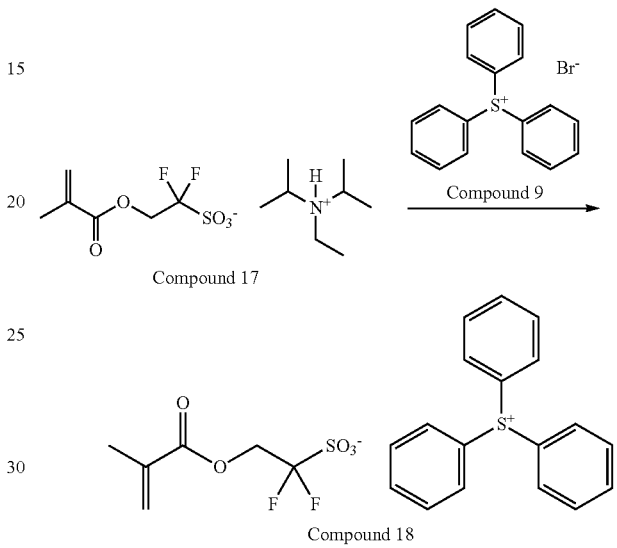

Comparative Example 3

Step of Obtaining Compound 15 from Compound 13:

5.00 g (27.2 mmol) of a compound 14 and 3.30 g (32.6 mmol) of triethylamine were added to an eggplant flask, and then 25 g of dichloroethane was added thereto, and then 3.12 g (29.9 mmol) of a compound 13 was added thereto in a dropwise manner while cooling with ice, followed by stirring for 1 hour at a room temperature, thereby obtaining a reaction solution containing a compound 15.

[Chemical Formula 79]

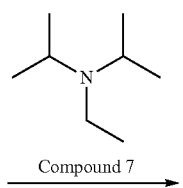

Compound 7

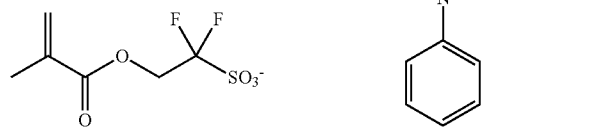

Compound 17

[Chemical Formula 81]

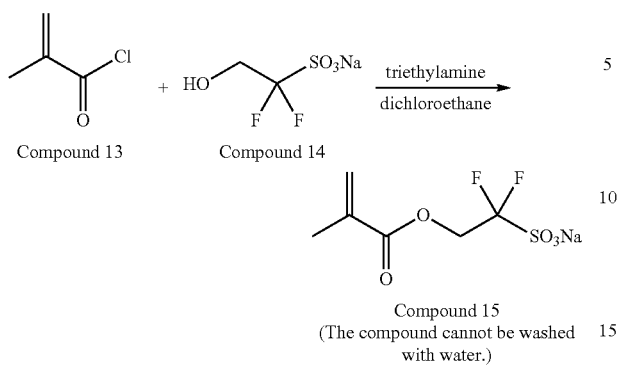

Compound 15
(The compound cannot be washed with water.)

[Compound 15]

The compound 15 cannot be extracted with an organic phase, and therefore, washing treatment with water cannot be conducted.

Step of Obtaining Compound 18 from Compound 15:

25 g of water and 11.2 g (32.6 mmol) of a compound 9 were added to the reaction solution containing a compound 15, followed by extracting the organic layer. The organic layer was washed with a small amount of water, and then added to an excess amount of TBME in a dropwise manner to precipitate a solid. Then, the precipitated solid was separated by filtration, followed by drying, thereby obtaining 11.8 g of a compound 18.

[Chemical Formula 82]

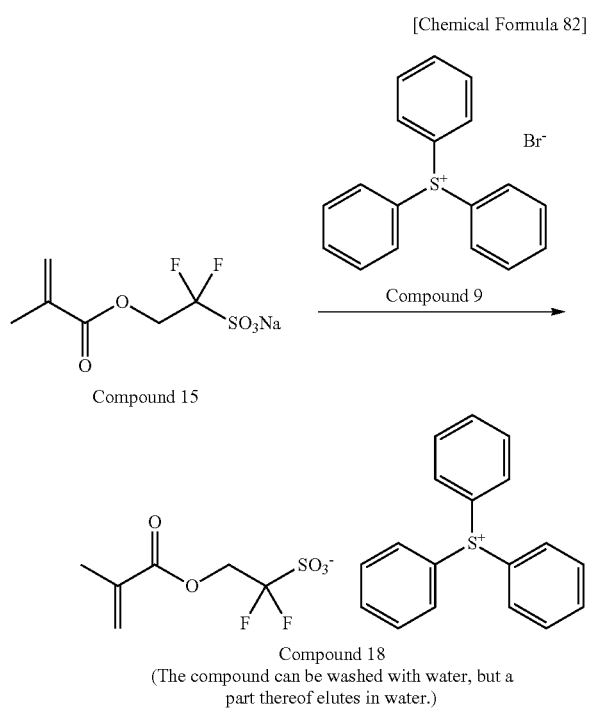

Compound 18
(The compound can be washed with water, but a part thereof elutes in water.)

[Compound 18]

The compound 18 obtained by conducting salt exchange reaction between the compound 15 and the compound 9 exhibits water solubility, and therefore, washing treatment with an excess amount of water cannot be conducted, such that impurities cannot be satisfactorily removed.

Further, because the compound 14 as an unreacted material is converted into the compound 52 having a relatively low water solubility, the compound 52 cannot be satisfactorily removed by washing treatment with a small amount of water.

[Chemical Formula 83]

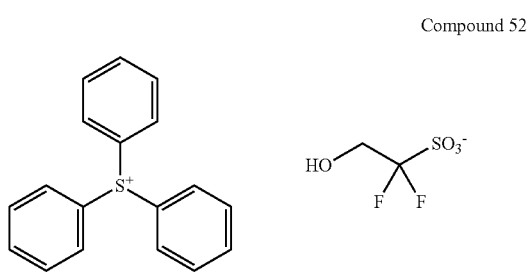

Comparative Example 4

Step of Obtaining Compound 20 from Compound 13:

5.00 g (19.0 mmol) of a compound 19 and 2.31 g (22.8 mmol) of triethylamine were added to a eggplant flask, and 25 g of dichloroethane was added thereto.

2.18 g (20.9 mmol) of a compound 13 was added to the eggplant flask in a dropwise manner while cooling with ice, followed by stirring for 1 hour at a room temperature. Next, the reaction solution was washed with a diluted hydrochloric acid and then washed with a small amount of water, and the solvent was distilled off, thereby obtaining 3.84 g (11.6 mmol) of a compound 20.

[Chemical Formula 84]

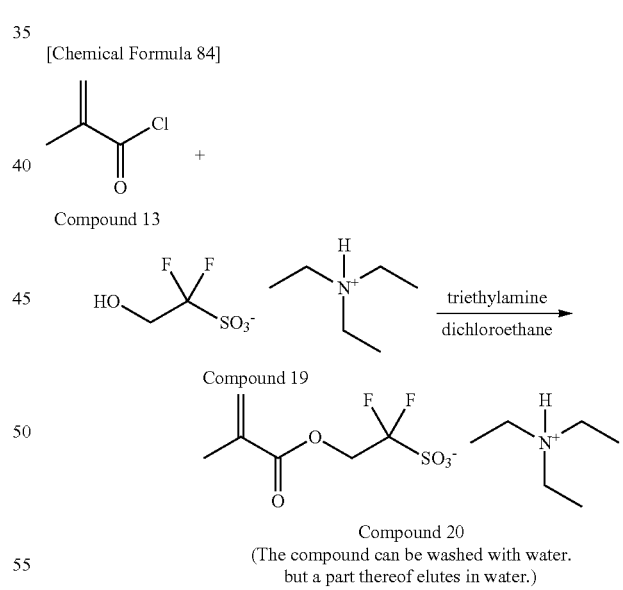

Compound 20
(The compound can be washed with water. but a part thereof elutes in water.)

Step of Obtaining Compound 18 from Compound 20:

3.84 g (11.6 mmol) of a compound 20 was dissolved in 19.2 g of dichloromethane, and 4.77 g (13.9 mmol) of a compound 9 and 19.2 g of water were added thereto, followed by stirring. Next, the organic layer was extracted, and was washed with a diluted hydrochloric acid and then washed with water, and then added to an excess amount of TBME in a dropwise manner to precipitate a solid. Then, the precipitated solid was separated by filtration, followed by drying, thereby obtaining 5 23 g of a compound 18.

[Chemical Formula 85]

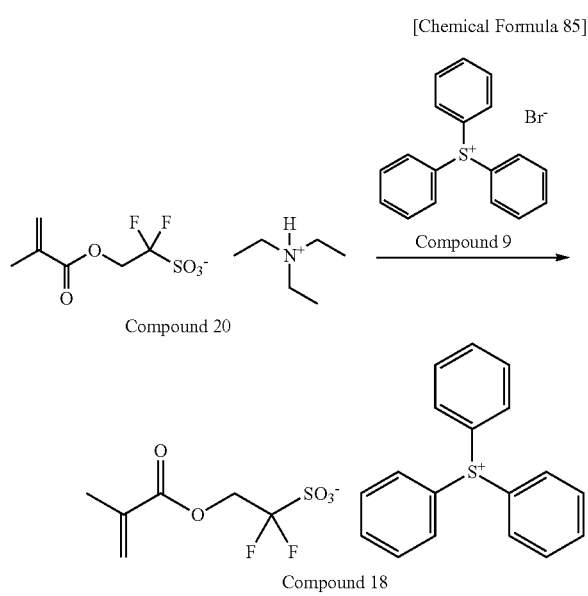

Compound 20

[Compound 20]
The compound 20 can be extracted with an organic phase, and the compound 53 has a high water solubility, and therefore, the compound 53 can be efficiently removed by washing treatment with water. However, the compound 20 also has a water solubility, part of the compound 20 is eluted into water together with the compound 53 by washing treatment with water.

[Chemical Formula 86]

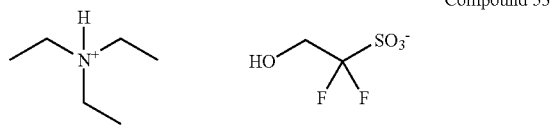

Compound 53

Example 3

Step of Obtaining Compound 18 from Compound 13:
10.0 g (23.6 mmol) of a compound 21 and 2.86 g (28.3 mmol) of triethylamine were added to an eggplant flask, and then 50 g of dichloroethane was added thereto, and then 2.71 g (25.9 mmol) of a compound 13 was added thereto in a dropwise manner while cooling with ice, followed by stirring for 1 hour at a room temperature. Then the organic solvent was extracted, and the organic solvent was distilled off, thereby obtaining 9.98 g of a compound 18.

[Chemical Formula 87]

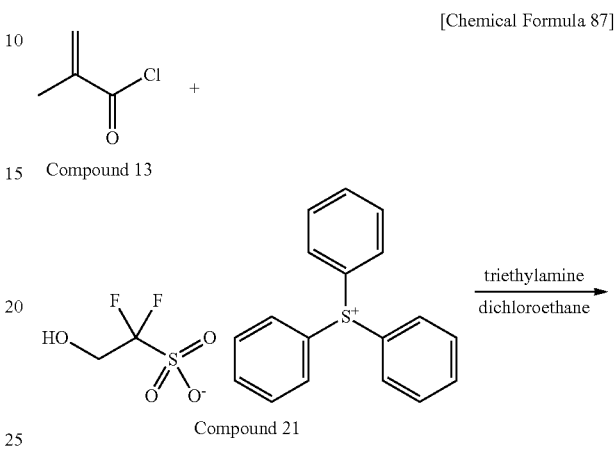

Compound 13

Compound 21

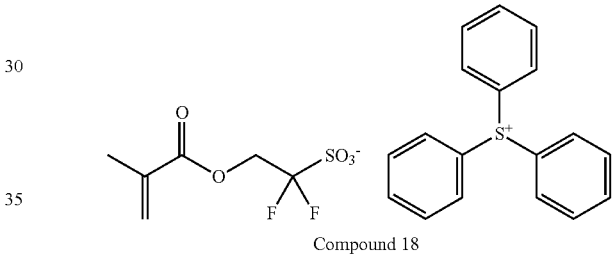

Compound 18

Step of Obtaining Compound 16 from Compound 18:
9.98 g (20.2 mmol) of a compound 18 was dissolved in 50 g of dichloromethane, and 8.70 g (30.4 mmol) of a compound 5 and 50 g of water were added thereto, followed by extracting the organic layer. Next, the organic layer was washed with a diluted hydrochloric acid and then washed with an excess amount of water, and the solvent was distilled off, thereby obtaining 8.29 g of a compound 16.

[Chemical Formula 88]

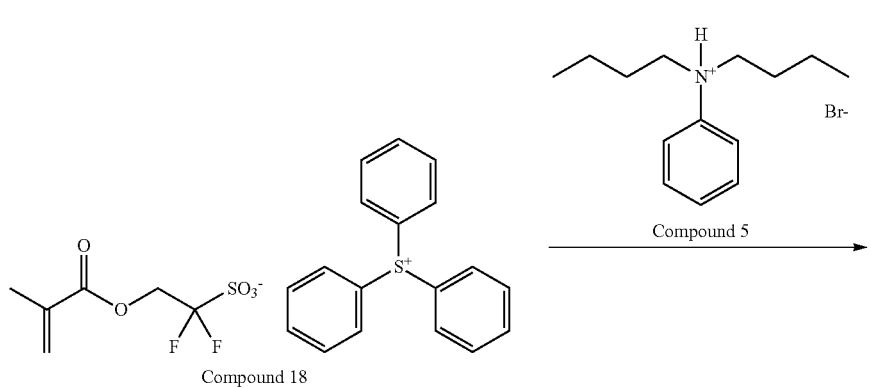

Compound 18

Compound 5

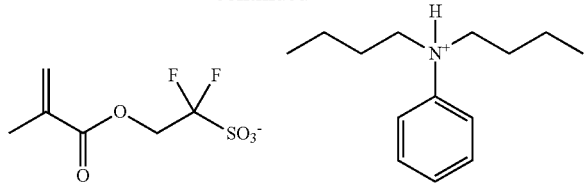

Compound 16
(The compound can be washed with
water without elution in water.)

Although the compound 18 can be subjected to washing treatment with a small amount of water, by virtue of obtaining the compound 16 by conducting salt exchange of the compound 18, washing treatment with an excess amount of water can be conducted, and therefore, impurities can be efficiently removed.

Step of obtaining compound 17 from compound 16:

8.29 g (19.0 mmol) of a compound 16 was dissolved in 33 g of acetonitrile, and 2.95 g (22.9 mmol) of a compound 7 and 33 g of n-heptane were added thereto, followed by extracting the acetonitrile layer. Next, the acetonitrile layer was washed with n-heptane, and the solvent was distilled off, thereby obtaining 6.71 g of a compound 17.

-continued

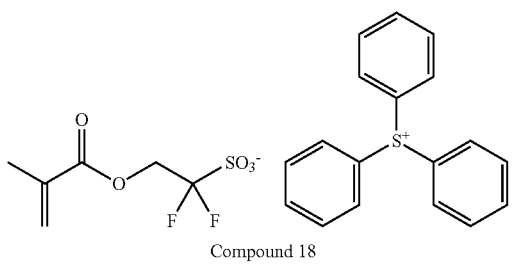

Compound 18

[Chemical Formula 89]

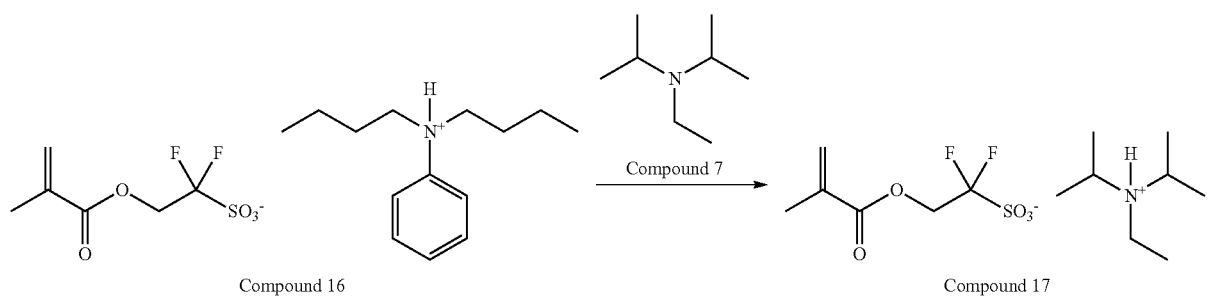

Compound 16 → Compound 17

Step of Obtaining Compound 18 from Compound 17:

6.71 g (18.7 mmol) of a compound 17 was dissolved in 34 g of dichloromethane, and 7.69 g (22.4 mmol) of a compound 9 and 34 g of water were added thereto, followed by extracting the dichloromethane layer. The dichloromethane layer was washed with water, and then added to an excess amount of TBME in a dropwise manner to precipitate a solid. Then, the precipitated solid was separated by filtration, followed by drying, thereby obtaining 8.92 g of a compound 18.

[Chemical Formula 90]

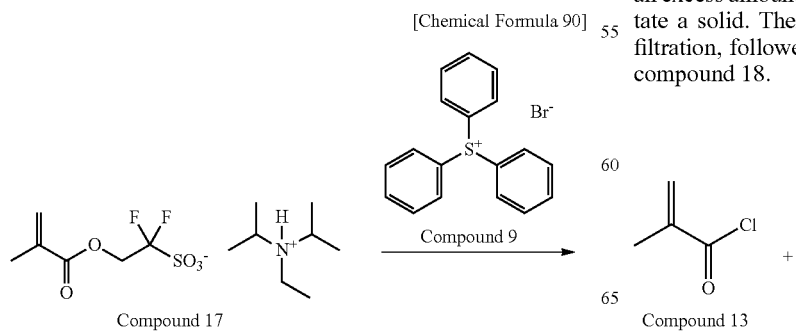

Compound 17 → (Compound 9)

Comparative Example 5

Step of Obtaining Compound 18 from Compound 13:

10.0 g (23.6 mmol) of a compound 21 and 2.86 g (28.3 mmol) of triethylamine were added to an eggplant flask, and then 50 g of dichloroethane was added thereto, and then 2.71 g (25 9 mmol) of a compound 13 was added thereto in a dropwise manner while cooling with ice, followed by stirring for 1 hour at a room temperature. Next, the organic layer was extracted, and washed with a diluted hydrochloric acid and then washed with a small amount of water, and then added to an excess amount of TBME in a dropwise manner to precipitate a solid. Then, the precipitated solid was separated by filtration, followed by drying, thereby obtaining 9.86 g of a compound 18.

[Chemical Formula 91]

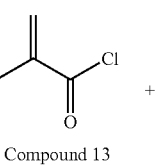

Compound 13

+

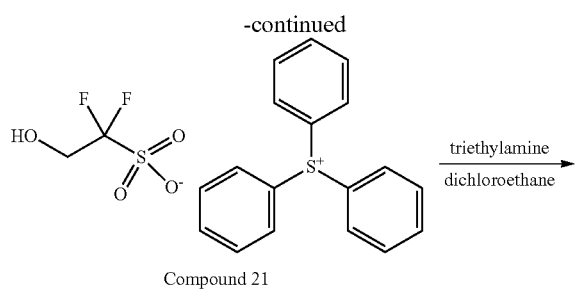

Compound 21

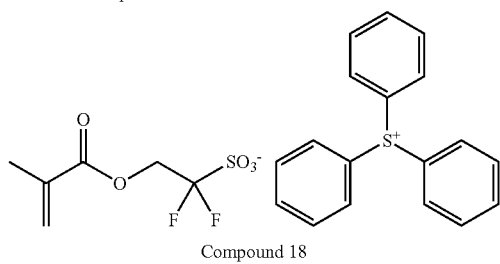

Compound 18
(The compound can be washed with water,
but a part thereof elutes in water.)

[Compound 18]

The compound 18 can be extracted with an organic phase, but has water solubility. Therefore, washing treatment with an excess amount of water cannot be conducted, and hence, the compound 21 as an unreacted material cannot be efficiently removed.

Example 4

The same procedure as in Example 2 was performed, that is, the similar procedure as in the production method in which the compound 15, compound 16 and compound 17 as intermediates were synthesized from the compound 13 as a starting material, and then the compound 18 was obtained as a final product was performed, thereby obtaining a compound 26. Specifically, from the compound 22 as a starting material, a compound 23, compound 24 and compound 25 were synthesized as intermediates, and then a compound 26 was obtained as a final product. The synthetic route is shown below.

[Chemical Formula 92]

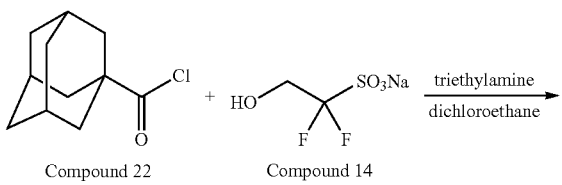

Compound 22     Compound 14

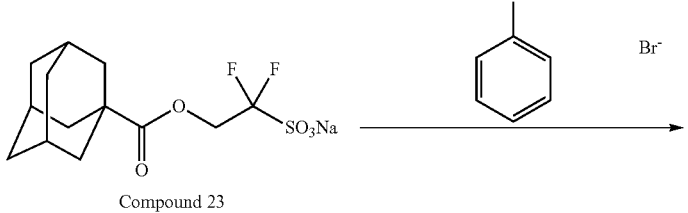

Compound 23

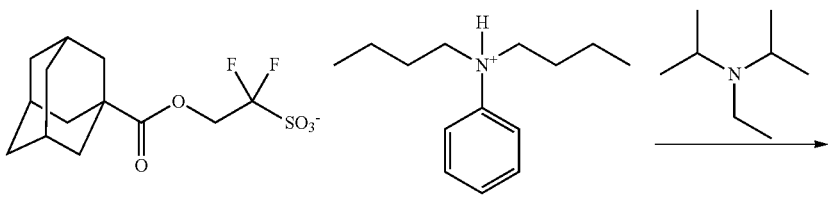

Compound 24
(The compound can be washed with water without
elution in water.)

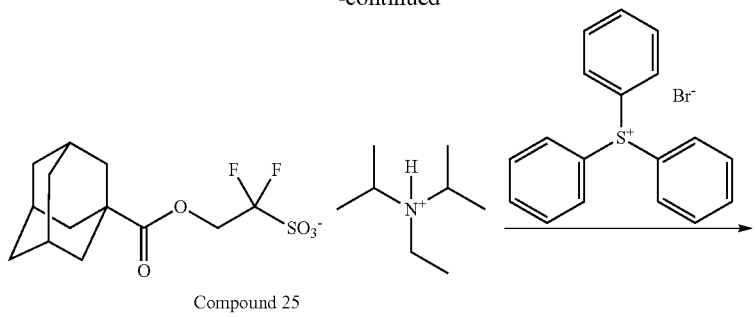

Compound 25

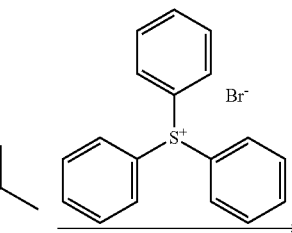

Compound 26

Comparative Example 6

The same procedure as in Comparative Example 3 was performed, that is, the similar procedure as in the production method in which the compound 15 as an intermediate was synthesized from the compound 13 as a starting material, and then the compound 18 was obtained by conducting salt exchange between the compound 15 and a sulfonium cation was performed, thereby obtaining a compound 26. Specifically, from the compound 22 as a starting material, a compound 23 was synthesized as an intermediate, and then the compound 23 was subjected to salt exchange with a sulfonium cation, thereby obtaining a compound 26 as a final product. The synthetic route is shown below.

[Chemical Formula 93]

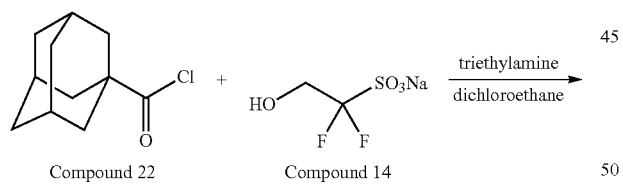

Compound 22    Compound 14

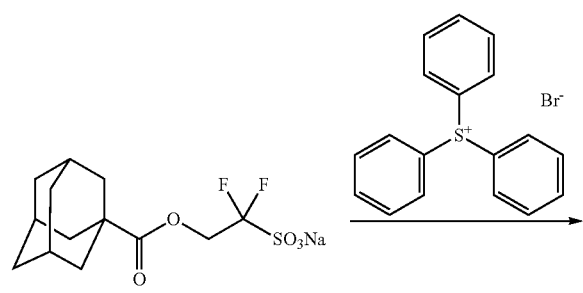

Compound 23
(The compound cannot be washed with water.)

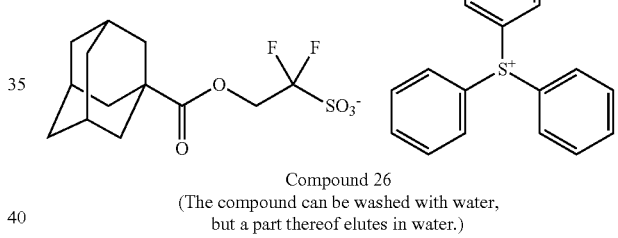

Compound 26
(The compound can be washed with water, but a part thereof elutes in water.)

Comparative Example 7

The same procedure as in Comparative Example 4 was performed, that is, the similar procedure as in the production method in which the compound 20 as an intermediate was synthesized from the compound 13 as a starting material, and then the compound 18 was obtained by conducting salt exchange between the compound 20 and a sulfonium cation was performed, thereby obtaining a compound 26. Specifically, from the compound 22 as a starting material, a compound 23 was synthesized as an intermediate, and then the compound 23 was subjected to salt exchange with a sulfonium cation, thereby obtaining a compound 26 as a final product. The synthetic route is shown below.

[Chemical Formula 94]

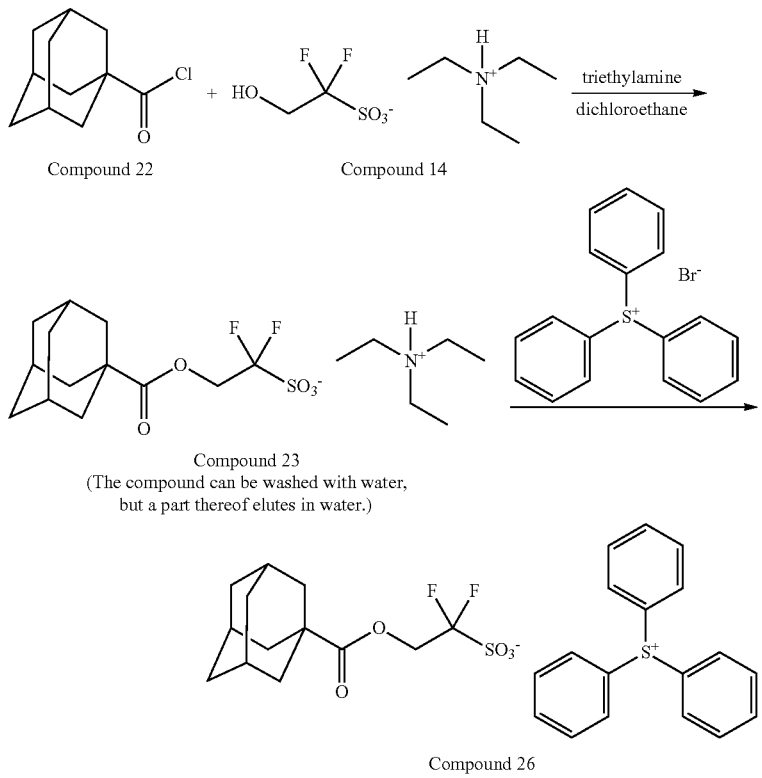

<Yield and Quantitative Determination of Impurity in Production Example of Compound>

With respect to production method of each compound, the yield of each compound and the quantitative determination of impurity were measured. The results are shown in Table 1.

The yield (%) was calculated by following formula; Actual yield of final product (g) (in the case of Example 4, compound 26)÷Theoretical yield (g)×100.

The quantitative determination of impurity was measured by using a detector Corona CAD (manufactured by ESA Biosciences, Inc).

In the table, as impurities, "Na" indicates sodium cation, "anion 1", "anion2" and "cation1" are respective ions represented by following formulae.

"-" indicates that there was no need for quantitative determination of impurities, because the final product was obtained through a synthetic route in which Na, cation1 and the like are not included.

[Chemical Formula 95]

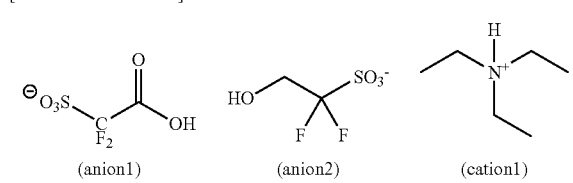

TABLE 1

| | | | Quantitative Determination of Impurity | | | |
|---|---|---|---|---|---|---|
| | Final Product | Yield (%) | Impurity | Quantitative Value | Impurity | Quantitative Value |
| Example 1 | Compound 10 | 73 | anion1 | <10 ppm | Na | <10 ppb |
| Comparative Example 1 | Compound 10 | 71 | anion1 | 80 ppm | Na | 90 ppb |
| Comparative Example 2 | Compound 10 | 33 | anion1 | <10 ppm | cation1 | <10 ppm |
| Example 2 | Compound 18 | 92 | anion2 | <10 ppm | Na | <10 ppb |
| Comparative Example 3 | Compound 18 | 88 | anion2 | 130 ppm | Na | 180 ppb |
| Comparative Example 4 | Compound 18 | 56 | anion2 | <10 ppm | cation1 | <10 ppm |

TABLE 1-continued

| | Final Product | Yield (%) | Impurity | Quantitative Value | Impurity | Quantitative Value |
|---|---|---|---|---|---|---|
| Example 3 | Compound 18 | 77 | anion2 | <10 ppm | — | — |
| Comparative Example 5 | Compound 18 | 85 | anion2 | 80 ppm | — | — |
| Example 4 | Compound 26 | 82 | anion2 | <10 ppm | Na | <10 ppb |
| Comparative Example 6 | Compound 26 | 80 | anion2 | 65 ppm | Na | 80 ppb |
| Comparative Example 7 | Compound 26 | 42 | anion2 | <10 ppm | cation1 | <10 ppm |

From the results shown in Table, by applying the production method of the present invention, it was confirmed that the final product can be obtained in high yield with hardly any impurities.

<Production Example of Polymeric Compound>

Example 5

By using the compound 18 obtained in Example 2 as a compound (a61), a polymeric compound having an acid generator group which generates acid upon exposure was produced as follows.

In a separable flask equipped with a thermometer, a reflux tube and a nitrogen inlet tube, 20.00 g (117.5 mmol) of a compound (a21), 29.14 g (148.5 mmol) of a compound (a11) and 21.33 g (43.30 mmol) of a compound (a61) were dissolved in 90.55 g of methyl ethyl ketone (MEK). Then, 21.6 mmol of dimethyl 2,2'-azobis(isobutyrate) (product name: V-601) as a polymerization initiator was added and dissolved in the resulting solution.

The solution was added to 49.12 g of MEK in a dropwise manner under a nitrogen atmosphere over 4 hours. After the dropwise addition, the resulting reaction solution was heated while stirring for 1 hour, and then cooled to a room temperature.

The obtained reaction polymer solution was added to an excess amount of n-heptane in a dropwise manner to precipitate a polymer. Thereafter, the precipitated white powder was separated by filtration, followed by washing with methanol and drying, thereby obtaining 45.81 g of a polymeric compound 1.

[Chemical Formula 96]

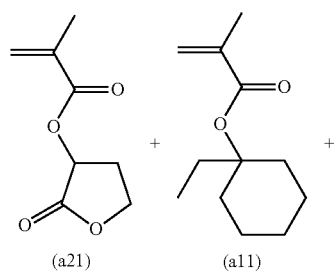

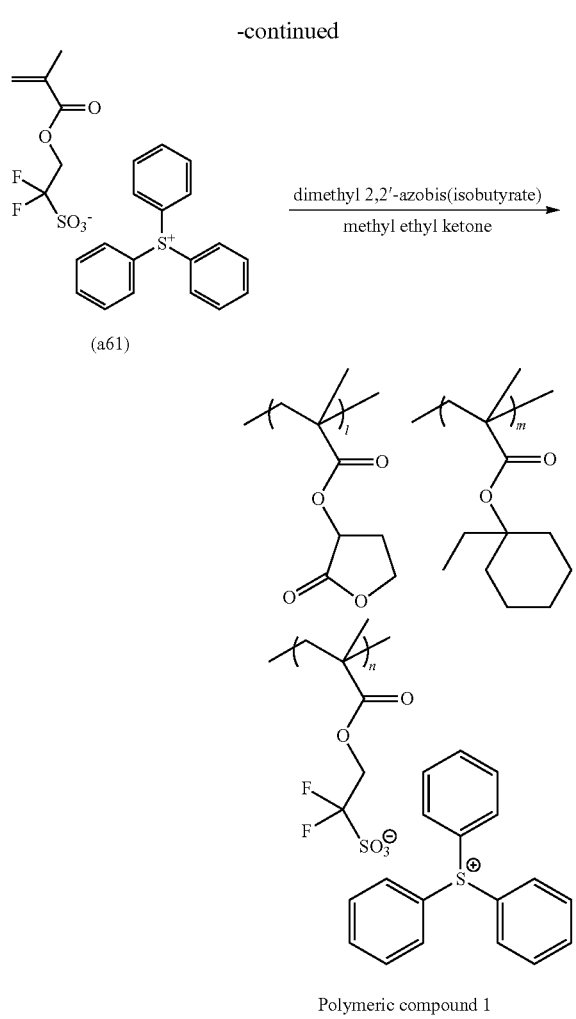

Comparative Example 8, Comparative Example 9

The same procedure as in Example 5 was performed, except that in Comparative Example 8, the compound 18 obtained in Comparative Example 3 was used as a compound (a61), and except that in Comparative Example 9, the compound 18 obtained in Comparative Example 4 was used as a compound (a61), thereby obtaining polymeric compounds 2 and 3 having an acid generator group which generates acid upon exposure.

<Yield and Quantitative Determination of Impurity in Production Example of Polymeric Compound>

With respect to production method of each polymeric compound, the results of the weight average molecular weight (Mw), the dispersity (Mw/Mn), the copolymer compositional ratio, the yield and the quantitative determination of impurity are shown in Table 2.

The Mw and Mw/Mn of the polymeric compound were determined by the polystyrene equivalent value as measured by gel permeation chromatography (GPC).

The copolymer compositional ratio (l/m/n; the molar ratio of the respective structural units constituting the polymeric compound) was determined by 13 nuclear magnetic resonance spectroscopy (600 MHz $^{13}$C-NMR).

The yield (%) was calculated by following formula; Actual yield of polymerization product (g)÷Theoretical yield (i.e., total amount of monomer used in the production of polymeric compound) (g)×100.

The quantitative determination of impurity was measured by using a detector Corona CAD (manufactured by ESA Biosciences, Inc).

TABLE 2

| | Final Product | Mw | Mw/Mn | Copolymer Compositional Ratio l/m/n | Yield (%) | Quantitative Determination of Impurity | | | |
|---|---|---|---|---|---|---|---|---|---|
| | | | | | | Impurity | Quantitative Value | Impurity | Quantitative Value |
| Example 5 | Polymeric Compound 1 | 11800 | 1.71 | 40.7/45.3/14.0 | 68 | anion2 | <10 ppm | Na | <10 ppb |
| Comparative Example 8 | Polymeric Compound 2 | 11300 | 1.78 | 39.7/45.1/15.2 | 65 | anion2 | 40 ppm | Na | 20 ppb |
| Comparative Example 9 | Polymeric Compound 3 | 11400 | 1.80 | 40.0/44.6/15.4 | 65 | anion2 | <10 ppm | Na | <10 ppb |

From the comparison between Example 5 and Comparative Example 8, it was confirmed that a final product having hardly any impurities can be produced in high yield, by polymerization of a monomer (i.e., compound 18) having hardly any impurities.

With respect to Comparative Example 9, the amount of impurities produced in polymerization is the same level as that of Example 5. However, the yield of the compound 18 (obtained in Comparative Example 4) as a monomer is low, which is disadvantageous in terms of mass productivity and cost.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method of producing an ammonium salt compound, comprising reacting a first ammonium salt compound containing a first ammonium cation which is a primary, secondary or tertiary ammonium cation with a nitrogen-containing compound having a lone pair to obtain a second ammonium salt compound which contains a conjugated acid of the nitrogen-containing compound, the conjugated acid of the nitrogen-containing compound having a larger pKa than the pKa of the first ammonium cation.

2. The method of producing an ammonium salt compound according to claim 1, wherein the conjugated acid of the nitrogen-containing compound has a lower hydrophobicity than the hydrophobicity of the first ammonium cation.

3. The method of producing an ammonium salt compound according to claim 1, wherein the first ammonium salt compound is obtainable by conducting salt exchange between the first ammonium cation and a compound (P) containing a cation which has a lower hydrophobicity than the hydrophobicity of the first ammonium cation.

4. The method of producing an ammonium salt compound according to claim 3, wherein the first ammonium salt compound is obtainable by conducting salt exchange between the first ammonium cation and the compound (P), and conducting washing treatment.

5. The method of producing an ammonium salt compound according to claim 3, wherein the compound (P) is a salt containing an organic anion and the cation which has a lower hydrophobicity than the hydrophobicity of the first ammonium cation.

6. The method of producing an ammonium salt compound according to claim 5, wherein the organic anion is a sulfonate anion, an amide anion, a methide anion or a carboxylate anion.

7. A method of producing a compound, comprising:
a step of reacting a first ammonium salt compound containing a first ammonium cation which is a primary, secondary or tertiary ammonium cation with a nitrogen-containing compound having a lone pair to obtain a second ammonium salt compound which contains a conjugated acid of the nitrogen-containing compound, the conjugated acid of the nitrogen-containing compound having a larger pKa than the pKa of the first ammonium cation; and
a step of conducting salt exchange between the second ammonium salt compound and a sulfonium cation or iodonium cation which has a higher hydrophobicity than the hydrophobicity of the conjugated acid of the nitrogen-containing compound.

8. The method of producing a compound according to claim 7, wherein the conjugated acid of the nitrogen-containing compound has a lower hydrophobicity than the hydrophobicity of the first ammonium cation.

9. The method of producing a compound according to claim 7, wherein the first ammonium salt compound is obtainable by conducting salt exchange between the first ammonium cation and a compound (P) containing a cation which has a lower hydrophobicity than the hydrophobicity of the first ammonium cation.

10. The method of producing a compound according to claim 9, wherein the first ammonium salt compound is obtainable by conducting salt exchange between the first ammonium cation and the compound (P), and conducting washing treatment.

11. The method of producing a compound according to claim 9, wherein the compound (P) is a salt containing an organic anion and a cation which has a lower hydrophobicity than the hydrophobicity of the first ammonium cation.

12. The method of producing a compound according to claim 11, wherein the organic anion is a sulfonate anion, an amide anion, a methide anion or a carboxylate anion.

13. A compound produced by the method of producing a compound of claim 7.

14. The compound according to claim 13, which contains a polymerizable group.

15. A polymeric compound comprising a structural unit derived from the compound of claim 14.

16. An acid generator comprising the compound of claim 13.

17. A resist composition comprising the acid generator of claim 16.

18. A resist composition comprising the polymeric compound of claim 15.

19. A method of forming a resist pattern, comprising: forming a resist film on a substrate using a resist composition of claim 17; conducting exposure of the resist film; and developing the resist film to form a resist pattern.

* * * * *